US011633359B2

(12) United States Patent
Enomura et al.

(10) Patent No.: US 11,633,359 B2
(45) Date of Patent: Apr. 25, 2023

(54) METHOD FOR PRODUCING ORGANIC MATERIAL MICROPARTICLES, AND METHOD FOR MODIFYING ORGANIC MATERIAL MICROPARTICLES

(71) Applicant: M. TECHNIQUE CO., LTD., Izumi (JP)

(72) Inventors: Masakazu Enomura, Izumi (JP); Kaeko Araki, Izumi (JP); Daisuke Honda, Izumi (JP)

(73) Assignee: M. TECHNIQUE CO., LTD., Izumi (JP)

( * ) Notice: Subject to any disclaimer, the term of this patent is extended or adjusted under 35 U.S.C. 154(b) by 178 days.

(21) Appl. No.: 15/535,980

(22) PCT Filed: Dec. 15, 2015

(86) PCT No.: PCT/JP2015/085124
§ 371 (c)(1),
(2) Date: Jun. 14, 2017

(87) PCT Pub. No.: WO2016/098785
PCT Pub. Date: Jun. 23, 2016

(65) Prior Publication Data
US 2017/0340564 A1   Nov. 30, 2017

(30) Foreign Application Priority Data

Dec. 15, 2014 (JP) .................................. 2014-253490
Feb. 5, 2015 (JP) .............................. JP2015-021639
Apr. 8, 2015 (JP) .............................. JP2015-079626
Dec. 7, 2015 (JP) .............................. JP2015-238452

(51) Int. Cl.
A61K 9/14        (2006.01)
A61K 31/12       (2006.01)
A61K 31/405      (2006.01)
A61K 31/5383     (2006.01)
C08J 3/12        (2006.01)
B01J 19/18       (2006.01)
B01J 19/00       (2006.01)
C09B 67/00       (2006.01)

(52) U.S. Cl.
CPC ............. *A61K 9/146* (2013.01); *A61K 31/12* (2013.01); *A61K 31/405* (2013.01); *A61K 31/5383* (2013.01); *B01J 19/0093* (2013.01); *B01J 19/1887* (2013.01); *C08J 3/12* (2013.01); *C09B 68/20* (2013.01); *B01J 2219/00889* (2013.01)

(58) Field of Classification Search
None
See application file for complete search history.

(56) References Cited

U.S. PATENT DOCUMENTS

| 6,485,658 | B1 * | 11/2002 | Horiuchi ............ C09B 67/0016 |
|           |      |         | 252/501.1 |
| 8,623,415 | B2   | 1/2014  | Enomura |
| 8,911,545 | B2   | 12/2014 | Enomura |
| 8,992,981 | B2   | 3/2015  | Enomura |
| 9,211,510 | B2   | 12/2015 | Enomura |
| 9,427,891 | B2   | 8/2016  | Enomura |
| 9,539,642 | B2   | 1/2017  | Maekawa et al. |
| 2004/0260083 | A1 * | 12/2004 | Shiromaru .......... C09B 67/0016 |
|              |      |         | 540/130 |
| 2009/0068576 | A1 * | 3/2009  | Hongo .................... C09B 47/10 |
|              |      |         | 430/57.1 |
| 2009/0269250 | A1   | 10/2009 | Panagiotou et al. |
| 2010/0009214 | A1   | 1/2010  | Sato et al. |
| 2010/0155310 | A1 * | 6/2010  | Enomura ................ B01F 23/53 |
|              |      |         | 977/840 |
| 2010/0215958 | A1   | 8/2010  | Enomura |
| 2010/0322997 | A1 * | 12/2010 | Enomura ............. A61K 9/0048 |
|              |      |         | 424/444 |

(Continued)

FOREIGN PATENT DOCUMENTS

CN    101784258 A    7/2010
CN    101796143 A    8/2010

(Continued)

OTHER PUBLICATIONS

JP4300279B2 Translation, accessed from: https://patents.google.com/patent/JP4300279B2/en?oq=JP4300279B2, accessed on Apr. 1, 2019, pp. 1-21 (Year: 2019).*

Ghani, F., et al., "Solubility Properties of Unsubstituted Metal Phthalocyanines in Different Types of Solvents" J. Chem. Eng. Data, pp. 439-449 (Year: 2012).*

Extended European Search Report, dated May 11, 2018, for European Application No. 15869990.0.

(Continued)

*Primary Examiner* — Michael G. Hartley
*Assistant Examiner* — Lance W Rider
(74) *Attorney, Agent, or Firm* — Birch, Stewart, Kolasch & Birch, LLP

(57) ABSTRACT

Provided are a method for producing organic material microparticles and a method for modifying organic material microparticles, whereby it becomes possible to improve the crystallinity of organic material microparticles or achieve the crystal transformation of the organic material microparticles while preventing the growth of the organic material microparticles in a solvent. A surfactant is added to a solvent that is capable of partially dissolving organic material microparticles, and then the organic material microparticles are reacted with the solvent. In this manner, it becomes possible to improve the degree of crystallization of the organic material microparticles or achieve the crystal transformation of the organic material microparticles without substantially altering the particle diameters of the organic material microparticles.

16 Claims, 37 Drawing Sheets

(56) References Cited

U.S. PATENT DOCUMENTS

| | | |
|---|---|---|
| 2010/0326321 A1 | 12/2010 | Enomura |
| 2011/0177337 A1* | 7/2011 | Enomura ............ B01F 7/00775 428/402 |
| 2012/0006230 A1 | 1/2012 | Enomura |
| 2013/0071664 A1* | 3/2013 | Maekawa ........... C09B 67/0019 428/402 |
| 2013/0274462 A1 | 10/2013 | Maekawa et al. |
| 2014/0048948 A1 | 2/2014 | Lee |
| 2014/0048984 A1 | 2/2014 | Enomura |
| 2014/0069326 A1 | 3/2014 | Yamanaka et al. |
| 2014/0110336 A1 | 4/2014 | Araki et al. |
| 2014/0110884 A1 | 4/2014 | Araki et al. |
| 2014/0121336 A1 | 5/2014 | Maekawa et al. |
| 2014/0155247 A1 | 6/2014 | Aoyagi et al. |
| 2014/0308158 A1 | 10/2014 | Maekawa et al. |
| 2015/0010456 A1 | 1/2015 | Kuraki et al. |
| 2015/0030760 A1 | 1/2015 | Enomura |
| 2015/0114179 A1 | 4/2015 | Enomura |
| 2015/0283616 A1 | 10/2015 | Maekawa et al. |
| 2017/0369969 A1 | 12/2017 | Maekawa et al. |

FOREIGN PATENT DOCUMENTS

| | | | |
|---|---|---|---|
| CN | 101801520 | A | 8/2010 |
| CN | 102516809 | A | 6/2012 |
| CN | 103492063 | A | 1/2014 |
| CN | 103561856 | A | 2/2014 |
| CN | 103561857 | A | 2/2014 |
| EP | 2703075 | A1 | 3/2014 |
| EP | 2716355 | A1 | 4/2014 |
| EP | 2719433 | A1 | 4/2014 |
| EP | 2781282 | A1 | 9/2014 |
| EP | 2821133 | A1 | 1/2015 |
| EP | 2896476 | A1 | 7/2015 |
| JP | 8-501073 | A | 2/1996 |
| JP | 2002-538199 | A | 11/2002 |
| JP | 2004-244563 | A | 9/2004 |
| JP | 2006-193681 | A | 7/2006 |
| JP | 2007-291168 | A | 11/2007 |
| JP | 2009-82902 | A | 4/2009 |
| JP | 4300279 | B2 * | 7/2009 |
| JP | 2010-242104 | A | 10/2010 |
| JP | 2014-23997 | A | 2/2014 |
| JP | 2014-50843 | A | 3/2014 |
| JP | 2015-61724 | A | 4/2015 |
| KR | 10-2010-0022093 | A | 2/2010 |
| WO | WO 93/25190 | A1 | 12/1993 |
| WO | WO 00/53164 | A1 | 9/2000 |
| WO | WO 2007/013599 | A1 | 2/2007 |
| WO | WO 2008/044519 | A1 | 4/2008 |
| WO | WO 2009/008388 | A1 | 1/2009 |
| WO | WO 2009/008391 | A1 | 1/2009 |
| WO | WO 2009/132171 | A1 | 10/2009 |
| WO | WO 2012/121180 | A1 | 9/2012 |
| WO | WO 2013/164886 | A1 | 11/2013 |

OTHER PUBLICATIONS

EP-2703075-A1 corresponds to US-2014/0048984-A1.
EP-2716355-A1 corresponds to US-2014/0121336-A1.
EP-2896476-A1 corresponds to US-2015/0283616-A1.
EP-2781282-A1 corresponds to US-2014/0308158-A1 and US-2017/0369969-A1.
EP-2719433-A1 corresponds to US-2014/0110336-A1.
EP-2821133-A1 corresponds to US-2015/0030760-A1.
International Search Report, issued in PCT/JP2015/085124, PCT/ISA/210, dated Feb. 2, 2016.

* cited by examiner

METHOD FOR PRODUCING ORGANIC MATERIAL MICROPARTICLES, AND METHOD FOR MODIFYING ORGANIC MATERIAL MICROPARTICLES

TECHNICAL FIELD

The present invention relates to a method for producing an organic material microparticle and a method for modifying an organic material microparticle.

BACKGROUND ART

When conventional organic materials are made to microparticles, especially to nanoparticles, a new function can be expressed synergistically with the physical properties thereof and thus, the technology to make the organic materials to nanoparticles has been an important theme in the entire industry.

Because the organic material nanoparticle has an extremely high specific surface area as compared with those materials in a solid state with the size of more than several micrometers, they have not only improved functions such as high reactivity and activity but also dramatically enhanced characteristics added to their inherent characteristics. Therefore, they are the materials expected to be used in a wide technical field.

In order to express the characteristics that are expected as the organic material nanoparticle, the particle diameter thereof needs to be controlled. However, in general, because the solubility of the organic material nanoparticle increases in a solvent, there are problems that growth and coarsening of the particle as well as necking are prone to take place due to recrystallization thereof.

Therefore, as described in Patent Document 1, the production method of a biologically ingestible substance is proposed wherein the substance is subjected to the crushing treatment in a poor solvent containing a surface modifying agent so as to keep the particle size thereof. In Patent Document 9, the production method of an organic pigment is proposed wherein a blue organic pigment such as a copper phthalocyanine is subjected to a dry crushing treatment added with an organic solvent.

However, when mechanical crushing treatments such as those described in these Patent Documents are carried out, crystallinity of the particle is prone to decrease, so that the problems that the particles after the crushing treatment aggregate in a solvent thereby causing coarsening of the particle can occur. In addition, in many cases, these mechanical crushing methods are conducted by means of a medium-using crushing method such as those using a ball mill, a sand mill, and a bead mill; and therefore, there have been such problems that contamination with impurities derived from these equipment cannot be readily avoided and that enormous time and energy are required to obtain an intended particle diameter.

Alternatively, Patent Document 2 discloses the methods in which a co-precipitation method or a crushing treatment method that is added with a surface-stabilizing agent in order to produce a nanoparticle composition showing stable particle diameter and minimum crystal growth after a long storage and/or an exposure to a high temperature. However, with regard to the crystallinity thereof, Patent Document 2 describes only that the particle is present as a crystal phase or an amorphous phase; and thus, there is no description with regard to control of the crystallinity such as the degree of crystallinity and crystal type thereof. Also the organic material nanoparticle produced by the method wherein an organic pigment solution in which an organic pigment is dissolved in a good solvent capable of dissolving the said organic pigment is mixed with a poor solvent having a lower solubility to the same than the good solvent so as to separate the organic pigment microparticle, such as those disclosed in Patent Document 10, often contains an amorphous portion; and thus, this method has a problem that the particle is prone to undergo coarsening in an organic solvent.

In order to express the characteristics expected as the organic material nanoparticle, not only control of the particle diameter but also control of the properties of the particle such as crystallinity and crystal type thereof is important. For example, in polymer compounds such as a resin, it is known that the characteristics of causing secondary aggregate and of sliding property are strongly influenced by the resin's degree of crystallinity. Therefore, in Patent Document 3, the method is disclosed wherein crystallinity of the resin microparticle is controlled by heat-treating the resin microparticle in the temperature range between equal to or higher than the glass transition temperature thereof and equal to or lower than the melting point thereof so as to obtain the heat-treated resin microparticle. In this method, however, the heat-treatment for a long period of time is necessary, so that the method with which the crystallinity can be controlled more conveniently has been wanted.

Accordingly, in Patent Documents 4 and 8, which are proposed by the present applicant, a biologically ingestible microparticle (Patent Document 4) or an organic pigment microparticle (Patent Document 8) is separated in a thin film fluid formed between processing surfaces which are disposed in a position they are faced with each other so as to be able to approach to and separate from each other, at least one of which rotates relative to the other. With these methods, not only fine and uniform organic material nanoparticle can be readily produced but also crystal diameter and crystal type of the separated organic material nanoparticle can be controlled.

However, the organic material nanoparticle is so fine that the specific surface area thereof is increased to cause an increase in its solubility; as a result, owing to the action of an amorphous portion of the particles, growth to a coarse particle in a solvent and necking of the particle can take place after separation of the particle.

Further, the technology has been known wherein, after the microparticle is separated, the crystallite's diameter of the separated microparticle is changed without changing the particle diameter of the separated microparticle, such as the one disclosed in Patent Document 5. In this technology, a uniform and homogeneous particle is obtained by growing the nucleus or the crystallite of the particle that is separated in a thin film fluid formed between at least two processing surfaces which are disposed in a position they are faced with each other so as to be able to approach to and separate from each other, at least one of which rotates relative to the other. Specifically, after a fluid having the particle separated is discharged from between the processing surfaces, the crystallite's diameter of the particle is controlled by controlling the residence time and the temperature during the said fluid is passing through a tubular vessel.

However, in Patent Document 5, although the crystallite's diameter of the particle is controlled by the residence time and temperature, problems of coarsening in a solvent and necking of the particle after the above-mentioned treatment remain yet to be solved.

In Patent Document 6, in order to prepare the sample for measurement, a copper phthalocyanine powder is introduced into a solution having a dispersant dissolved in an organic solvent so as to conduct a dispersion treatment. However, the copper phthalocyanine microparticle used therein has an extremely high crystallinity from the beginning, and the action of the solvent or the dispersant to the organic material microparticle is completely different from those of the present invention. Moreover, this dispersion treatment is conducted for the purpose of measurement. Therefore, this cannot be regarded as the method for modification of the microparticle or for control of the properties of the microparticle.

In organic materials, especially in the case of the organic pigment, the color characteristics of the organic pigment are dependent on the particle's properties such as the particle diameter and crystallinity. Therefore, as the use of the organic pigment expands, precise control of the properties of the organic pigment and the organic pigment microparticle is wanted. However, there is no decisively effective method to suppress the crystal growth. The often used method in which the organic pigment is made to nanoparticle together with a derivative thereof (Patent Document 7) has a problem that development to a required color is difficult because the color that is characteristic to the derivative can affect the color development of the actually used organic pigment.

As discussed above, organic material microparticles of various materials such as a biologically ingestible substance, a resin, and a pigment are used in various fields and applications, wherein in any of these applications, properties of the particle such as the particle diameter and the degree of crystallinity can significantly affect the performance thereof. Therefore, not only precise control of the properties of the organic material microparticle but also a method to suppress the change in the particle properties until actual use of the organic material microparticle is wanted.

CITATION LIST

Patent Documents

Patent Document 1: Japanese Patent Application Publication No. H08-501073
Patent Document 2: Japanese Patent Application Publication No. 2002-538199
Patent Document 3: Japanese Patent Laid-Open Publication No. 2007-291168
Patent Document 4: Japanese Patent Application Re-Publication No. 2009-8391
Patent Document 5: Japanese Patent Laid-Open Publication No. 2014-23997
Patent Document 6: Japanese Patent Laid-Open Publication No. 2010-242104
Patent Document 7: International Patent Laid-Open Publication No. 2008/044519
Patent Document 8: Japanese Patent Laid-Open Publication No. 2009-82902
Patent Document 9: Japanese Patent Laid-Open Publication No. 2004-244563
Patent Document 10: Japanese Patent Laid-Open Publication No. 2006-193681

SUMMARY OF THE INVENTION

Problem to be Solved by the Invention

As discussed above, in order to utilize the characteristics inherently owned by the organic material microparticle, the problem to be solved by the present invention is to provide a method for producing the organic material microparticle wherein the crystallinity thereof can be enhanced or the crystal transition thereof can be effected with suppressing the growth of the organic material microparticle in a solvent. To solve the problem mentioned above, inventors of the present invention carried out trial and error, and as a result, they found that when a particle property control solution having a surfactant dissolved in a solvent, the surfactant being capable of protecting an organic material microparticle from receiving the action of the said solvent, which has a partial dissolvability to the organic material microparticle at least part of which is composed of an amorphous portion, was made to act to the organic material microparticle, the degree of crystallinity of the organic material microparticle could be enhanced or the crystal transition of the organic material microparticle could be effected, without substantially changing the particle diameter of the organic material microparticle. On the basis of this finding, the present invention could be achieved.

Means for Solving the Problem

That is to say, the present invention relates to a method for producing an organic material microparticle, wherein a surfactant is added into a solvent which has a partial dissolvability to the organic material microparticle, at least part of which is composed of an amorphous portion, and the said solvent is made to act to the organic material microparticle, thereby enhancing a degree of crystallinity of the organic material microparticle without substantially changing a particle diameter of the organic material microparticle.

Also, the present invention relates to a method for producing an organic material microparticle, wherein a surfactant is added into a solvent which has a partial dissolvability to the organic material microparticle, at least part of which is composed of an amorphous portion, and the said solvent is made to act to the organic material microparticle, thereby effecting a crystal transition of the organic material microparticle without substantially changing a particle diameter of the organic material microparticle.

Also, the present invention relates to the method for producing the organic material microparticle, wherein a rate of change in the particle diameter of the organic material microparticle measured before and after the solvent having the surfactant added therein is made to act to the organic material microparticle (after surfactant treatment (A)/before surfactant treatment (B)) is in a range of 1 to 4.

Also, the present invention relates to a method for producing an organic material microparticle, wherein the method comprises: a step 1 in which a raw material solution of the organic material microparticle is mixed with a separating solvent L for separating at least one kind of the organic material microparticles from the raw material solution of the organic material microparticle thereby effecting separation of the organic material microparticle (P1); and a step 2 in which a particle property control solution having a surfactant, which is capable of suppressing growth of the organic material microparticle, added into a solvent which has a partial dissolvability to the organic material microparticle is prepared thereby making the organic material microparticle (P1) act to the said particle property control solution, wherein the step 2 is made to act so as to control particle properties of the organic material microparticle (P1).

Also, the present invention relates to the method for producing the organic material microparticle, wherein the step 2 is made to act so as to change at least any one of degree of crystallinity, crystal type, and crystal diameter of the organic material microparticle (P1).

Also, the present invention relates to the method for producing the organic material microparticle, wherein the method comprises a step c in which the organic material microparticle (P1) obtained in the step 1 is subjected to washing and/or solvent substitution, and an organic material microparticle (P2) obtained in the step c is made to act to the particle property control solution.

Also, the present invention relates to the method for producing the organic material microparticle, wherein the organic material microparticle contains an amorphous portion at least in part thereof.

Also, the present invention relates to the method for producing the organic material microparticle, wherein at a time when the organic material microparticle is made to act to the solvent or at a time when the organic material microparticle is made to act to the particle property control solution, a stirring treatment is conducted so as to control properties of the organic material microparticle, or properties of the organic material microparticle (P1), or properties of the organic material microparticle (P2), by means of a stirring energy.

Also, the present invention relates to the method for producing the organic material microparticle, wherein the organic material microparticle is a biologically ingestible substance.

Also, the present invention relates to the method for producing the organic material microparticle, wherein the organic material microparticle is a resin.

Also, the present invention relates to the method for producing the organic material microparticle, wherein the organic material microparticle is an organic pigment such as a red organic pigment and a blue organic pigment.

Also, the present invention relates to the method for producing the organic material microparticle, wherein the step 1 is conducted in a microreactor in which at least two fluids to be processed, comprising the raw material solution of the organic material microparticle and the separating solvent L, are introduced into between a first processing surface and a second processing surface which are disposed in a position they are faced with each other so as to be able to approach to and separate from each other, at least one of which rotates relative to the other; a separating force which acts in a direction to separate the first processing surface and the second processing surface from each other is generated by an introduction pressure imparted to between the first processing surface and the second processing surface; with keeping a minute distance between the first processing surface and the second processing surface by the separating force, the at least two fluids to be processed are caused to converge with each other between the first processing surface and the second processing surface that are kept at the minute distance thereby causing to pass the fluids to be processed through between the first processing surface and the second processing surface so as to form a thin film fluid; and the fluids to be processed are made to react with each other in the thin film fluid. The said stirring can be conducted by using a stirrer equipped with a rotating and stirring blade.

In execution of the present invention, the particle diameter of the organic material microparticle obtained by the production method mentioned above may be variously changed in accordance with the applied use and so forth; for example, the particle diameter may be in the range of 100 nm or less, or 30 nm or less. For example, the particle diameters of the organic material microparticles measured before and after the organic material microparticle is made to act to the solvent having a partial dissolvability to the organic material microparticle and having the surfactant added therein may be in the range of 100 nm or less, or the particle diameter of the organic material microparticle (P1) may be in the range of 30 nm or less.

Also, the present invention relates to the method for producing the organic material microparticle, wherein the solvent does not substantially contain a pigment derivative.

Also, the present invention relates to a method for modifying an organic material microparticle, wherein the method is to modify an organic material microparticle without substantially changing a particle diameter of the organic material microparticle; the method comprises a step in which a particle property control solution having a surfactant dissolved in a solvent which has a partial dissolvability to the organic material microparticle is made to act to the organic material microparticle; by conducting this step, a degree of crystallinity of the organic material microparticle is enhanced so as to modify the organic material microparticle such that the degree of crystallinity thereof may be matched with a prescribed intended condition.

Also, the present invention relates to the method for modifying the organic material microparticle, wherein the method is to modify an organic material microparticle without substantially changing a particle diameter of the organic material microparticle; the method comprises a step in which a particle property control solution having a surfactant dissolved in a solvent which has a partial dissolvability to the organic material microparticle is made to act to the organic material microparticle; and by conducting this step, a crystal type of the organic material microparticle is changed so as to modify the organic material microparticle in such a way that the crystal type thereof may be matched with a prescribed intended condition.

Also, the present invention relates to the method for modifying the organic material microparticle, wherein a rate of change in the particle diameter of the organic material microparticle measured before and after the treatment in the step (after the treatment in the step (A)/before the treatment in the step (B)) is in a range of 1 to 4.

Also, the present invention relates to the method for modifying the organic material microparticle, wherein the organic material microparticle before the treatment in the step contains an amorphous portion at least in part thereof.

Advantageous Effects of the Invention

By using the production method of the present invention, not only the particle growth of the organic material microparticle can be suppressed but also the crystal type and crystallinity thereof can be controlled; and thus, the organic material microparticle capable of fully expressing the performance inherently owned by the organic material microparticle can be produced. In addition, by precisely controlling the properties of the organic material microparticle, the method for producing the organic material microparticle capable of satisfying various industrial requirements can be provided. Further, because properties of the particle can be conveniently controlled in the organic solvent which has a partial dissolvability to the organic material microparticle, various kinds of the organic material microparticle having the characteristics matched with respective intended purposes can be produced from one kind of the organic material microparticles, so that the production cost thereof can be drastically reduced.

Especially, when the method for producing the organic material microparticle of the present invention is used in a microreactor with the type of a forced thin film, which is capable of controlling crystallinity of the particle to be separated, properties of the microparticle can be further controlled after the organic material microparticle containing an amorphous portion is separated from the microreactor, so that the organic material microparticle having a very wide range of characteristics can be readily produced.

BRIEF DESCRIPTION OF THE DRAWINGS

FIG. 2 (B) shows a rough cross-sectional view of the microreactor with the type of a forced thin film according to other embodiments of the present invention.

DESCRIPTION OF THE EMBODIMENTS

Figure 1:
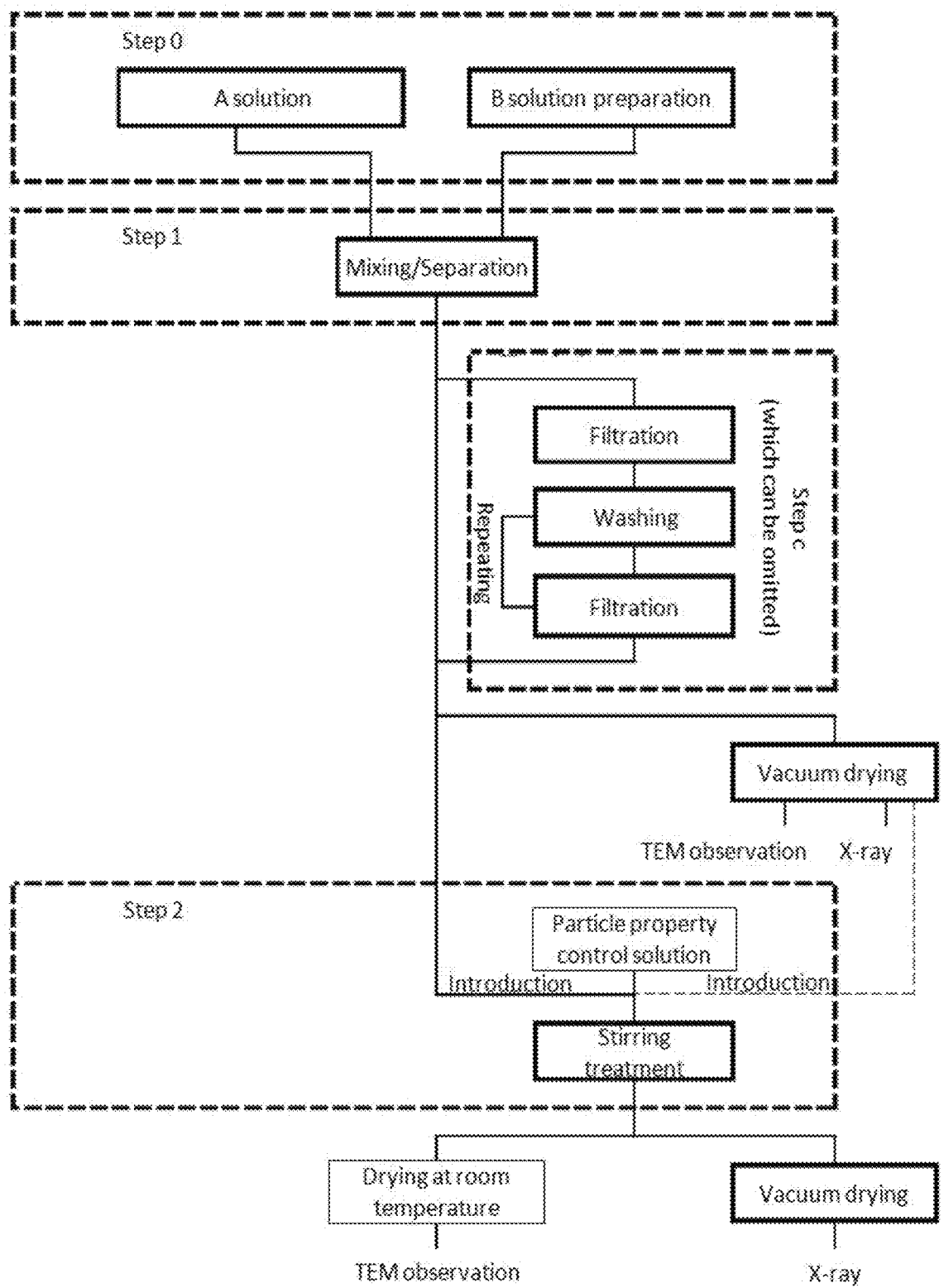
FIG. 1 This shows one example of the treatment processes according to embodiments of the present invention.

Hereinafter, the embodiments of the present invention will be explained in detail. Meanwhile, the embodiments of the present invention are not limited only to the embodiments described below.

In the present invention, the term "organic material" is a compound containing a carbon atom, and comprised of mainly carbons and oxygens. Therefore, they are not particularly restricted so that it does not matter whether they are artificially synthesized or extracted from natural substances. Illustrative example thereof includes biologically ingestible substances such as drug compositions, foods, food additives, and health foods; polymers such as synthetic resins, synthetic fibers, and rubbers; coloring compounds such as dyes, pigments, and paints; and fragrances and agricultural chemicals. In the present invention, the organic material microparticle means the microparticles of the above-described organic materials.

The biologically ingestible substance is not particularly restricted so far as the purpose thereof is to be ingested into a biological body. Illustrative example thereof includes those absorbed into a living body so as to express the effect thereof in the living body such as a drug in a pharmaceutical product, those passing through a living body and then discharged therefrom, those transporting a drug component in a drug delivery system, those applied to a skin of a living body such as cosmetics, as well as foods and intermediate bodies of these materials. Specifically, they are organic materials used in drugs, quasi-drugs, cosmetics, foods, food additives, health foods, etc. The biologically ingestible substances of the present invention may be commercially available or newly synthesized.

Illustrative example of the ingestible substance includes: drug compositions such as analgesic agents, anti-inflammatory agents, anthelmintic agents, antiarrhythmic agents, antibiotics, anticoagulants, antihypertensive drugs, antidiabetic agents, antiepileptic drugs, antihistaminic agents, anti-malignant tumor agents, anorectic drugs, anti-obesity drugs, antimuscarinic drugs, antimycobacterial agents, antineoplastic agents, immunosuppressive agents, antithyroid agents, antibacterial agents, antiviral agents, anti-anxiety drugs, astringents, beta-adrenoceptor blockers, blood derivatives, plasma substitutes, myocardial inotropic agents, contrast media, corticosteroids, cough suppressants, diagnostic agents, diagnostic image-forming agents, diuretic agents, dopaminergic agents, hemostatic drugs, immunological agents, lipid regulatory agents, muscle relaxants, parasympathomimetic agents, parathyroid calcitonin, bisphosphonates, prostaglandins, radioactive agents, sex hormones, antiallergic agents, stimulants, anorexigenic agents, sympathomimetics, thyroid agents, vasodilators, xanthines, cataract remedies, adrenal corticosteroids, and allergic rhinitis drugs; food nutrient supplements such as nutritiously effective substances, vitamins, minerals, and herbs; foods or food additives such as folic acid, aliphatic acids, extracts of fruits and vegetables, vitamin supplements, mineral supplements, phosphatidyl serine, lipoic acid, melatonin, glucosamine/chondroitin, Aloe vera, guggle, glutamine, amino acids, green tea, and lycopene; and beauty-assisting foods such as herbs, plant nutrients, antioxidants, fruit flavonoids, collagens, hyaluronic acid, amino acids, vitamin C derivatives, and hydroquinones, though not limited to them. Included as the preferable properties thereof are a low solubility and a capacity of being administered orally or by injection.

Illustrative example of the drug includes danazol, tacrolimus hydrate, progesterone, indomethacin, curcumin, tranilast, benzbromarone, naproxen, phenytoin, carotene, piposaru pham, piposarufan, camptothecin, acetaminophen, acetylsalicylic acid, amiodarone, colestyhumin, colestipol, cromolyn sodium, albuterol, sucralfate, sulfasalazine, minoxidil, temazepam, alprazolam, propoxyphene, auranofin, erythromycin, cyclosporine, aciclovir, ganciclovir, etoposide, mephalan, methotrexate, mitoxantrone, daunorubicin, doxorubicin, megestrol, tamoxifen, medroxyprogesterone, nystatin, terbutaline, amphotericin B, aspirin, ibuprofen, diclofenac, ketoprofen, flurbiprofen, diflumisal, diosgenin, cilostazol, tolbutamide, peptide, sodium cromoglicate, and pirenoxine.

Illustrative example of the quasi-drug includes teeth pastes, medicinal cosmetics, hair growth agents, mouth fresheners, and bad breath prevention agents.

Illustrative example of the cosmetic includes basic skincare cosmetics such as skin lotion, milky lotion, and toning lotion, as well as sunscreen cosmetics, make-up cosmetics, hair cosmetics, cleaning cosmetics, lip cosmetics, mouth cosmetics, nail cosmetics, eyeliner cosmetics, and bathing cosmetics.

Illustrative example of the food or the food additive includes vitamins such as vitamins A, B, C, E, etc., or derivatives thereof, as well as amino acids, carotenoids, and extracts from fruits and plants.

Illustrative example of the health food includes coenzyme Q 10, as well as vitamins such as vitamins A, B, C, E, etc., or derivatives thereof. These may be used singly or as a mixture of two or more of them.

In the present invention, there is no particular restriction in the resin. Illustrative example thereof includes thermoplastic resins (condensed thermoplastic resins such as polyester resins, polyamide resin, polyurethane resins, poly(thio) ether resins, polycarbonate resins, polysulfone resins, and polyimide resins; vinyl polymer thermoplastic resins such as polyolefin resins, (meth)acryl resins, styrene resins, and vinyl resins; thermoplastic elastomers; nature-originated resins such as cellulose derivatives; and thermoplastic silicone resins), as well as thermosetting resins (such as epoxy resins, unsaturated polyester resins, diallyl phthalate resins, and silicone resins (silicone rubber and silicone varnish)). These resins may be used singly or as a combination of two or more of them. Usually, thermoplastic resins and water-insoluble resins (or hydrophobic resins, water-insoluble thermoplastic resins, etc.) are preferably used.

As for the polyester resins, various resins using a dicarboxylic acid component, a diol component, an oxycarboxylic acid, and a lactone may be used. Illustrative example of the polyester includes polyC2-6alkylene-arylate resins such as polyethylene terephthalate, polytrimethylene terephthalate, polypropylene terephthalate, polybutylene terephthalate, poly1,4-cyclohexyldimethylene terephthalate, polyethylene naphthalate, and polybutylene naphthalate; copolyesters containing a C2-6 alkylene-arylate unit as a main component (for example, 50% or more by weight) (copolyesters having copolymer components of, for example, polyoxy C2-4alkylene glycols having an oxyalkylene unit, C6-12 aliphatic dicarboxylic acids, and asymmetric aromatic dicarboxylic acids such as isophthalic acid and phthalic acid); aromatic polyester resins such as polyarylate resins and liquid crystal polyesters; polyC2-6alkyleneglycol C2-10 aliphatic dicarboxylate esters such as polyC2-6alkylene oxalate, polyC2-6alkylene succinate, and polyC2-6alkylene adipate; polyoxycarboxylic acid resins (for example, polyglycolic acid, polylactic acid, and glycolic acid-lactic acid copolymer); polylactone resins (for example, polyC3-12 lactone resins such as polycaprolactone); and copolyetsers of them (for example, polycaprolacone-polybutylene succinate copolymer resin). These polyester resins may contain a urethane bond. In addition, theses polyester resins may be biologically degradable.

Illustrative example of the polyamide resin includes aliphatic polyamide resins, alicyclic polyamide resins, and aromatic polyamide resins, wherein aliphatic polyamide resins are usually used. These polyamide resins may be used singly or as a combination of two or more of them. Illustrative example of the aliphatic polyamide resin includes condensation products (for example, polyamide 46, polyamide 66, polyamide 610, polyamide 612, polyamide 1010, polyamide 1012, and polyamide 1212) formed of an aliphatic diamine component (C4-10 alkylene diamines such as tetramethylene diamine and hexamethylene diamine) and an aliphatic dicarboxylic acid component (C4-20 alkylene dicarboxylic acids such as adipic acid, sebacic acid, and dodecane dicarboxylic acid); homopolymers or copolymers (for example, polyamide 6, polyamide 11, polyamide 12, polyamide 6/11, and polyamide 6/12) formed of a lactam (C4-20 lactams such as ε-caprolactam and ω-laurolactam) or an amino carboxylic acid (C4-20 amino carboxylic acids such as ω-amino undecanoic acid); and copolyamides formed by copolymerization of these polyamide components (for example, polyamide 66/11 and polyamide 66/12). The dicarboxylic acid component in the polyamide resins may contain a dimer acid unit. Further, the polyamide resins may be biologically degradable.

As for the ether resins, especially poly(thio)ether resins, illustrative example thereof includes polyoxyalkylene resins (stabilized polyoxymethylene glycol or homo or copolyacetal resins, and polyoxy C2-4 alkylene glycols such as polyoxypropylene glycol, polyoxytetramethylene glycol, and polyoxyethylene-polyoxypropylene block copolymer), polyphenylene ether resins, polyphenylene ether ketone resins, polysulfide resins (polythioether resins such as polyphenylene sulfide or copolymers thereof), and polyether ketone resins (such as polyether ether ketone resins).

The polyolefin resins are exemplified by homopolymers or copolymers of α-C2-6 olefins, wherein illustrative example thereof includes homopolymers or copolymers of olefins such as polyethylene, polypropylene, ethylene-propylene copolymer, and polymethylpenetene-1; copolymers of an olefin and a copolymerizable monomer (such as ethylene-vinyl acetate copolymer, ethylene-(meth)acrylic acid copolymers and ethylene-(meth)acrylate ester copolymers). These polyolefin resins may be used singly or as a combination of two or more of them.

As for the vinyl resins, illustrative example of the halogen-containing vinyl resin includes polyvinyl chloride resins, vinyl chloride-vinyl acetate copolymer, vinylidene chloride resins, and fluorine-containing resins.

Illustrative example of the other vinyl resin or the derivative thereof includes homopolymers or copolymers of vinyl carboxylate esters (such as polyvinyl acetate and ethylene-vinyl acetate copolymer), saponification products thereof (polyvinyl alcohol resins such as polyvinyl alcohol and ethylene-vinyl alcohol copolymer), derivatives from the saponification products (vinyl alcohol resins) (for example, polyvinyl acetal resins such as polyvinyl formal and polyvinyl butyral). In the ethylene-vinyl alcohol copolymers, content of ethylene may be in the range of about 5 to 40% by weight.

The present invention may be applied to various pigments that can be provided and produced as the organic pigment.

For example, as for the red pigment of the present invention, commercially available pigments or newly synthesized pigments may be used. Illustrative example thereof includes pigments that are classified to C. I. Pigment Red in the color index, and part of the pigments that are classified to C. I. Pigment Violet and to C. I. Pigment Orange. More specific example thereof includes quinacridone pigments such as C. I. Pigment Red 122 and C. I. Pigment Violet 19; diketo pyrrolo pyrrole pigments such as C. I. Pigment Red 254 and C. I. Pigment Orange 73; naphthol pigments such as C. I. Pigment Red 150 and C. I. Pigment Red 170; perylene pigments such as C. I. Pigment Red 123; and azo pigments such as C. I. Pigment Red 144.

In addition, the present invention may be applied to blue organic pigments. These blue organic pigments include organic pigments having blueish colors such as blue, deep blue, and cyan.

As for the blue organic pigment of the present invention, commercially available pigments or newly synthesized pigments may be used. Illustrative example thereof includes pigments that are classified to C. I. Pigment Blue. More specific example thereof includes C. I. Pigment Blue-1, C. I. Pigment Blue-2, C. I. Pigment Blue-3, C. I. Pigment Blue-15, C. I. Pigment Blue-15:2, C. I. Pigment Blue-15:3, C. I. Pigment Blue-15:4, C. I. Pigment Blue-16, C. I. Pigment Blue-22, C. I. Pigment Blue-60, and C. I. Pigment Blue-75. These may be used singly or as a mixture of two or more of them.

As for the organic pigment of the present invention, a composite phthalocyanine microparticle may also be used. Many kinds of the composite phthalocyanine microparticle have been provided and sold until today, so that they may be used. Alternatively, they may also be newly synthesized.

Especially, the applicant of the present invention developed the composite phthalocyanine microparticles, such as a copper-titanyl phthalocyanine microparticle, a copper-cobalt phthalocyanine microparticle, and a copper-titanyl-cobalt phthalocyanine microparticle, these being optimal as coloring materials such as the pigment having the crystal growth thereof suppressed and satisfying the required characteristics with the size of nanometers, preferably 100 nm or less. Further, the present applicant also developed the method for producing the same. The composite phthalocyanine microparticles obtained by this method may also be used in the present invention.

Hereunder, this new composite phthalocyanine microparticle will be explained. The method for producing the composite phthalocyanine microparticle comprises: a step 0 in which as raw materials at least a copper phthalocyanine and a titanyl phthalocyanine and/or a cobalt phthalocyanine are dissolved in a first solvent to obtain a dissolved solution; a step 1 in which the dissolved solution obtained in the step 0 is mixed with a second solvent capable of being a poor solvent to the raw materials thereby effecting separation of the composite phthalocyanine; and a step 2 in which an organic solvent is made to act to the composite phthalocyanine obtained in the step 1.

The organic solvent is preferably a solvent based on an aromatic compound or a solvent based on a heterocyclic compound; and for example, the organic solvent is preferably at least one solvent selected from the group consisting of styrene, xylene, toluene, benzene, cresol, cumene, and tetrahydrofuran. When the solvent based on an aromatic compound or on an alicyclic compound that can induce or facilitate the crystal transition from an alpha-type copper phthalocyanine to a beta-type crystal structure or the like which is usually more stable than the alpha-type is used as the organic solvent, surprisingly the crystal transition to the more stable beta-type crystal structure or the like can be suppressed; and on top of it, the crystal growth can be suppressed.

Also, the present invention may be executed such that a mixing weight ratio of the raw materials (copper phthalocyanine/titanyl phthalocyanine and/or copper phthalocyanine/cobalt phthalocyanine) in the step 0 is in a range of 1 or more to less than 20. Further, the present invention may be executed such that the titanyl phthalocyanine and the cobalt phthalocyanine are simultaneously or successively dissolved in the step 0.

Similarly to the step 1 of the present invention mentioned before, the above-mentioned step 1 may be executed by using a microreactor in which at least two fluids to be processed are made to react with each other.

Also, the present invention may be executed such that both the composite phthalocyanine obtained in the step 1 and the composite phthalocyanine obtained in the step 2 are of the same crystal type. That is to say, even if the organic solvent is made to act to the composite phthalocyanine obtained in the step 1, the crystal transition does not take place in the step 2. Also, a surfactant or a dispersant is added in the organic solvent.

In the composite phthalocyanine microparticle, it is suitable that the aspect ratio thereof is in a range of 1.1 to 2.5 (both inclusive) and the particle diameter thereof is in a range of 5 to 100 nm (both inclusive). The above-mentioned aspect ratio is defined as the ratio of a long side to a short side in each composite phthalocyanine microparticle such as the copper-titanyl phthalocyanine microparticle. For example, if the shape thereof can be regarded as a cuboid shape or a quasi-cuboid shape, this is defined as the ratio of the longest side to the shortest side of the three sides thereof. If the shape thereof can be regarded as a sphere shape or a quasi-sphere shape, this is defined as the ratio of the longest diameter to the shortest diameter. Also, for example, the aspect ratio is defined as an average value of the long diameters to the short diameters of 100 particles measured with an observation by using a transmission electron microscopy (TEM).

The present invention may be executed such that a relative value ([Abs(a)]/[Abs(b)]) is 0.8 or more, wherein Abs (a) is defined as "Abs" at the peak top in the range of 655 to 700 nm of an absorption spectrum of the composite phthalocyanine microparticle in a UV-visible region and Abs (b) is defined as "Abs" at the peak top in the range of 550 to 640 nm of the same. The above-mentioned "Abs" is defined as the absorbance measured in the UV-visible absorption spectrum and calculated on the basis of the Lambert-Beer's law; and "Abs" at the peak top is defined as the maximum value among "Abs" in a specified wavelength range.

As for the surfactant of the present invention, various commercially available products shown below, or newly synthesized surfactants may be used. Although there is no particular restriction, illustrative example thereof includes anionic surfactants, cationic surfactants, nonionic surfactants, and amphoteric surfactants, as well as dispersants such as various polymers. Depending on the use thereof, the surfactant to be used can be restricted. For example, in the case of biologically ingestible substances, poisonous characters and the like to a living body need to be taken into consideration. Though not to limit to the following, illustrative example of the surfactant includes those based on dodecylbenzenesulfonic acid such as Neogen R-K (manufactured by Dai-Ichi Kogyo Seiyaku Co., Ltd.); Solsperse 20000, Solsperse 24000, Solsperse 26000, Solsperse 27000, Solsperse 28000, and Solsperse 41090 (all manufactured by Avecia Corp.); BYK 108, Disperbyk 160, Disperbyk 161, Disperbyk 162, Disperbyk 163, Disperbyk 166, Disperbyk 170, Disperbyk 180, Disperbyk 181, Disperbyk 182, Disperbyk 183, Disperbyk 184, Disperbyk 190, Disperbyk 191, Disperbyk 192, Disperbyk 2000, Disperbyk 2001, Disperbyk 2163, and Disperbyk 2164 (all manufactured by BYK-Chemie); Polymer 100, Polymer 120, Polymer 150, Polymer 400, Polymer 401, Polymer 402, Polymer 403, Polymer 450, Polymer 451, Polymer 452, Polymer 453, EFKA-46, EFKA-47, EFKA-48, EFKA-49, EFKA-1501, EFKA-1502, EFKA-4540, and EFKA-4550 (all manufactured by EFKA Chemical Corp.); Kaosera 2000, Pelex TG, and Pelex TR (all manufactured by Kao Corp.); Flowlen DOPA-158, Flowlen DOPA-22, Flowlen DOPA-17, Flowlen G-700, FlowlenTG-720W, Flowlen-730W, Flowlen-740W, and Flowlen-745W (all manufactured by Kyoeisha Chemical Co., Ltd.); Ajisper PA111, Ajisper PB711, Ajisper PB811, Ajisper PB821, and Ajisper PW911 (all manufactured by Ajinomoto Co., Inc.); Johncryl 678, Johncryl 679, and Johncryl 62 (all manufactured by Johnson Polymer B. V.); celluloses such as hydroxymethyl cellulose, hydroxyethyl cellulose, hydroxypropyl cellulose, hydroxypropylmethyl cellulose, carboxymethyl cellulose, sodium carboxymethyl cellulose, methyl cellulose, and ethyl cellulose; polymers such as polyvinyl alcohol; lipids such as polyvinyl pyrrolidone, lecithin, and cholesterol; sulfonium compounds; plant resins such as Arabic gum and Ghatti gum; gelatin, casein, phosphatide, dextran, glycerol, tragacanth, stearic acid, benzalkonium chloride, calcium stearate, glycerol monostearate, cetostearyl alcohol, and cetomarcrogol emulsified wax; sorbitan esters such as Span 80, Span 60, and Span 20; polyoxyethylene alkyl ethers and polyoxyethylene castor oil derivative; polyoxyethylene sorbitan fatty acid esters such as Tween 80, Tween 60, Tween 40, and Tween 20; polyethylene glycol, dodecyl trimethyl ammonium bromide, polyoxyethylene stearate, colloidal silicon dioxide, phosphates, sodium dodecylsulfate, and 4-(1,1,3,3-tetramethylbutyl)-phenol polymer with ethylene oxide and formaldehyde; poloxamers such as Lutrol F127, Lutrol F108, Futrol F87, and Futrol F68; poloxamines; charged lipids and dioctyl sulfosuccinate; dialkyl esters of sodium sulfosuccinic acid; sodium laurylsulfate, alkyl aryl polyether sulfonates, a mixture of sucrose stearate and sucrose distearate, p-isononyl phenoxy polyglycidol, decanoyl-N-methylgulcamide, n-decyl β-D-gulcopyranoside, n-decyl β-D-maltopyranoside, n-dodecyl β-D-gulcopyranoside, n-dodecyl β-D-maltoside, heptanoyl-N-methyl gulcamide, n-heptyl β-D-gulcopyranoside, n-heptyl β-D-thiogulcoside, n-hexyl β-D-gulcopyranoside, nonanoyl-N-methyl gulcamide, n-noyl β-D-gulcopyranoside, octanoyl-N-methyl gulcamide, n-octyl β-D-gulcopyranoside, octyl β-D-thiogulcopyranoside, lysozyme, PEG-lipids, PEG-cholesterol, PEG-cholesterol derivatives, PEG-vitamin A, random copolymer of vinyl acetate and vinyl pyrrolidone, quaternary ammonium compounds, benzyl-di(2-chloroethyl) ethyl ammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, C12-15 dimethyl hydroxyethyl ammonium chlorides, C12-15 dimethyl hydroxyethyl ammonium chloride bromides, coconut dimethyl hydroxyethyl ammonium chloride, coconut dimethyl hydroxyethyl ammonium bromide, myristyl trimethyl ammonium sulfate, lauryl dimethyl benzyl ammonium chloride, lauryl dimethyl benzyl ammonium bromide, lauryl dimethyl (ethenoxy) 4 ammonium chloride, lauryl dimethyl (ethenoxy) 4 ammonium bromide, N-alkyl (C12-18)dimethylbenzyl ammonium chlorides, N-alkyl (C14-18) dimethylbenzyl ammonium chlorides, N-tetradecyldimethylbenzyl ammonium chloride monohydrate, dimethyl didecyl ammonium chloride, N-alkyl and (C12-14) dimethyl 1-napthylmethyl ammonium chlorides, trimethylammonium halides, alkyltrimethylammonium salts, dialkyldimethylammonium salts, lauryl trimethyl ammonium chloride, ethoxylated alkylamido alkyldialky 1 ammonium salts, ethoxylated trialkyl ammonium salts, dialkylbenzene dialkylammonium chlorides, N-didecyldimethyl ammonium chloride, N-tetradecyldimethylbenzyl ammonium, chloride monohydrate, N-alkyl(C12-4) dimethyl 1-naphthylmethyl ammonium chlorides, dodecyldimethylbenzyl ammonium chloride, dialkyl benzenealkyl ammonium chlorides, lauryl trimethyl ammonium chloride, alkylbenzyl methyl ammonium chlorides, alkyl benzyl dimethyl ammonium bromides, C12 trimethyl ammonium bromides, C15 trimethyl ammonium bromides, C17 trimethyl ammonium bromides, dodecylbenzyl triethyl ammonium chloride, poly-diallyldimethylammonium chloride (DADMAC), dimethyl ammonium chloride, alkyldimethyl ammonium halides, tricetyl methyl ammonium chloride, decyltrimethyl ammonium bromide, dodecyltriethyl ammonium bromide, tetradecyltrimethyl ammonium bromide, methyl trioctyl ammonium chloride, POLYQUAT 10™, tetrabutyl ammonium bromide, benzyl trimethyl ammonium bromide, choline esters, stearalkonium chloride compounds, cetyl pyridinium bromide, cetyl pyridinium chloride, halide salts of quaternized polyoxyethylalkylamines, MIRAPOL™, ALKAQUAT™, alkyl pyridinium salts, amines, amine salts, amine oxides, imide azolinium salts, protonated quaternary acrylamides, and methylated quaternary polymers. These may be used singly, or two or more of them may be concurrently used.

In the cases that the organic material microparticles are of low-molecular weight organic materials shown in Examples A, such as, for example, indomethacin, curcumin, and pirenoxine, though not limited to these cases, it is preferable to use polymer surfactants such as water-soluble nitrogen-containing vinyl polymers and nonionic cellulose derivatives. More specific illustrative example thereof includes hydroxypropyl cellulose, hydroxyethyl cellulose, carboxymethyl cellulose, methyl cellulose, polyvinyl alcohol, and polyvinyl pyrrolidone. In addition, there are cases that nonionic surfactants such as Tween 80 and polyoxyethylene-hardened castor oil can be effective in view of dispersibility, so that it is also preferable to use them together with the polymer surfactant. In the cases that the organic material microparticles are of organic materials of the pigments shown in Examples B and C, it is preferable to use polymer surfactants such as an acryl polymer and a high-molecular weight block copolymer, surfactants such as a hydroxyl-group containing carboxylate ester, and anionic surfactants such as a sodium dialkylsulfo succinate and a sodium dodecylbenzenesulfonate.

In the organic material microparticle of the present invention, a polymer surfactant of a block copolymer may be used as well. In this case, illustrative example of the block copolymer includes acrylic or methacrylic block copolymers, block copolymers of polystyrene and other addition polymerization or condensation polymerization block, and block copolymers having the blocks of polyoxyethylene and polyoxyalkylene. Conventionally known block copolymers may also be used. The block copolymer to be used in the present invention is preferably amphiphilic. Specific preferable forms include diblock copolymers having a hydrophobic segment and a hydrophilic segment having an organic acid or its ionic salt unit. Also, triblock copolymers having a hydrophobic segment, a hydrophilic segment having an organic acid or its ionic salt unit, and another segment are preferably used. The triblock copolymers are used preferably in the form having a hydrophobic segment, a nonionic hydrophilic segment, and a hydrophilic segment having an organic acid or its ionic salt unit; and these are also preferably used for stabilization of their inclusion state. For example, when the triblock copolymer described above is used to prepare a dispersion solution using an organic material such as a pigment material and water as a solvent, the organic material such as the pigment can be included in micelles formed by the triblock copolymer. In addition, the particle diameter of the particles in the dispersion composition can be made very even and uniform. Further, the dispersed state thereof can be made highly stable, too.

As for the solvent to be used in the present invention, various solvents may be used in order to dissolve the raw materials of the organic material microparticle, to separate the organic material microparticle from the raw material solution of the organic material microparticle, and to control the properties of the organic material microparticle by adding the surfactant to be described later. Illustrative example of the solvent includes water (distilled water, purified water, etc.) and organic solvents (alcohol-based solvents, ketone-based solvents, ether-based solvents, aromatic-based solvents, aliphatic hydrocarbon-based solvents, nitrile-based solvents, sulfoxide-based solvents, halogen-based solvents, ester-based solvents, amine-based solvents, and ionic solutions). These solvents may be used by selecting one, or two or more solvents as a mixture thereof, in accordance with the aim of the embodiment. In addition, as the case may be, pH of the solution may be controlled by adding an acidic substance or a basic substance to these various solvents.

The above-mentioned solvents will be explained more specifically. Illustrative example of the alcohol-based solvent includes methanol, ethanol, isopropanol, n-propanol, 1-methoxy-2-propanol (PGME); linear alcohols such as n-butanol; branched alcohols such as 2-butanol and tert-butanol; and polyvalent alcohols such as ethylene glycol and diethylene glycol. Illustrative example of the ketone-based solvent includes acetone, methyl ethyl ketone, and cyclohexanone. Illustrative example of the ether-based solvent includes dimethyl ether, diethyl ether, and tetrahydrofuran. Illustrative example of the aromatic-based solvent includes styrene, toluene, xylene, phenol, nitrobenzene, chlorobenzene, dichlorobenzene, tetrahydrofuran, and pyridine. Illustrative example of the aliphatic-based solvent includes pentane, hexane heptane, octane, and cyclohexane. Illustrative example of the nitrile-based solvent includes acetonitrile. Illustrative example of the sulfoxide-based solvent includes dimethyl sulfoxide, diethyl sulfoxide, hexamethylene sulfoxide, and sulfolane. Illustrative example of the halogen-based solvent includes chloroform, dichloromethane, trichloroethylene, and iodoform. Illustrative example of the ester-based solvent includes ethyl acetate, butyl acetate, methyl lactate, ethyl lactate, and propylene glycol monomethyl ether acetate (PGMEA). Illustrative example of the ionic liquid includes benzyl trimethyl ammonium hydroxide (BTMA) and a salt of 1-butyl-3-methylimidazolium and PF6 (hexafluorophosphate ion). Illustrative example of the amine-based solvent includes dimethylamino ethanol, ethylenediamine, methylamine, dimethylamine, trimethylamine, ethylamine, diethylamine, and triethylamine. Illustrative example of the amide-based solvent includes N,N-dimethylformamide and N,N-dimethylacetamide.

"The solvent which has a partial dissolvability to the organic material microparticle" in the present invention does not indicate a strong dissolvability to completely dissolve all of the organic material microparticles from the time when the solvent is made to act to the organic material microparticles till completion of this treatment, but does indicate such degree of dissolvability so as to cause some "change" in the properties of the microparticles. Hereinafter, this solvent is also called as "the solvent having a partial dissolvability". The term "change" used here is not particularly restricted, while illustrative example thereof includes the phenomenon that when the solvent is made to act to the organic material microparticles, part of the organic material microparticles grows to cause coarsening thereof and the phenomenon that the organic material microparticles undergo necking with each other.

For example, solubility of the organic material microparticle to the solvent having a partial dissolvability is preferably in the range of 1 to 1000 μ/g both inclusive (in the range of 1 to 1000 ppm both inclusive), while more preferably in the range of 1 to 500 μ/g both inclusive (in the range of 1 to 500 ppm both inclusive), wherein the solubility is measured by using the organic material microparticles having an average particle diameter of 1000 nm. Even if the microparticles are not completely dissolved, if the solvent has too much solubility to the organic material microparticle, the particle growth and degree of coarsening of the particle become so high that application thereof to the present invention becomes difficult.

Meanwhile, the above-mentioned solubility is measured as follows. After the organic material microparticles having an average particle diameter of 1000 nm are made to act to the solvent, the microparticles are filtrated out through a filter having the pore diameter of about 0.1 to 0.2 μm, and then, the filtrate thereof is subjected to the UV-Vis measurement (visible-UV spectrophotometric measurement) so as to calculate concentration of the organic material dissolved in the solvent. Calculation of the concentration thereof may be made on the basis of measurements by means of other detection method such as measurement with fluorescence or refractive index of the filtrate.

In combination of the organic material microparticle and the solvent having a partial dissolvability, for example, when the organic material microparticle is of indomethacin, curcumin, or pirenoxine, solvents to be preferably used are linear alkanes such as pentane, hexane, heptane, octane, nonane, decane, and undecane, and cyclic alkanes such as cyclohexane, as well as water. For example, when the organic material microparticle is of polypropylene, solvents to be preferably used are alcohol-based solvents such as methyl alcohol and isopropyl alcohol, as well as aromatic-based solvents such as toluene and xylene.

Figure 8:
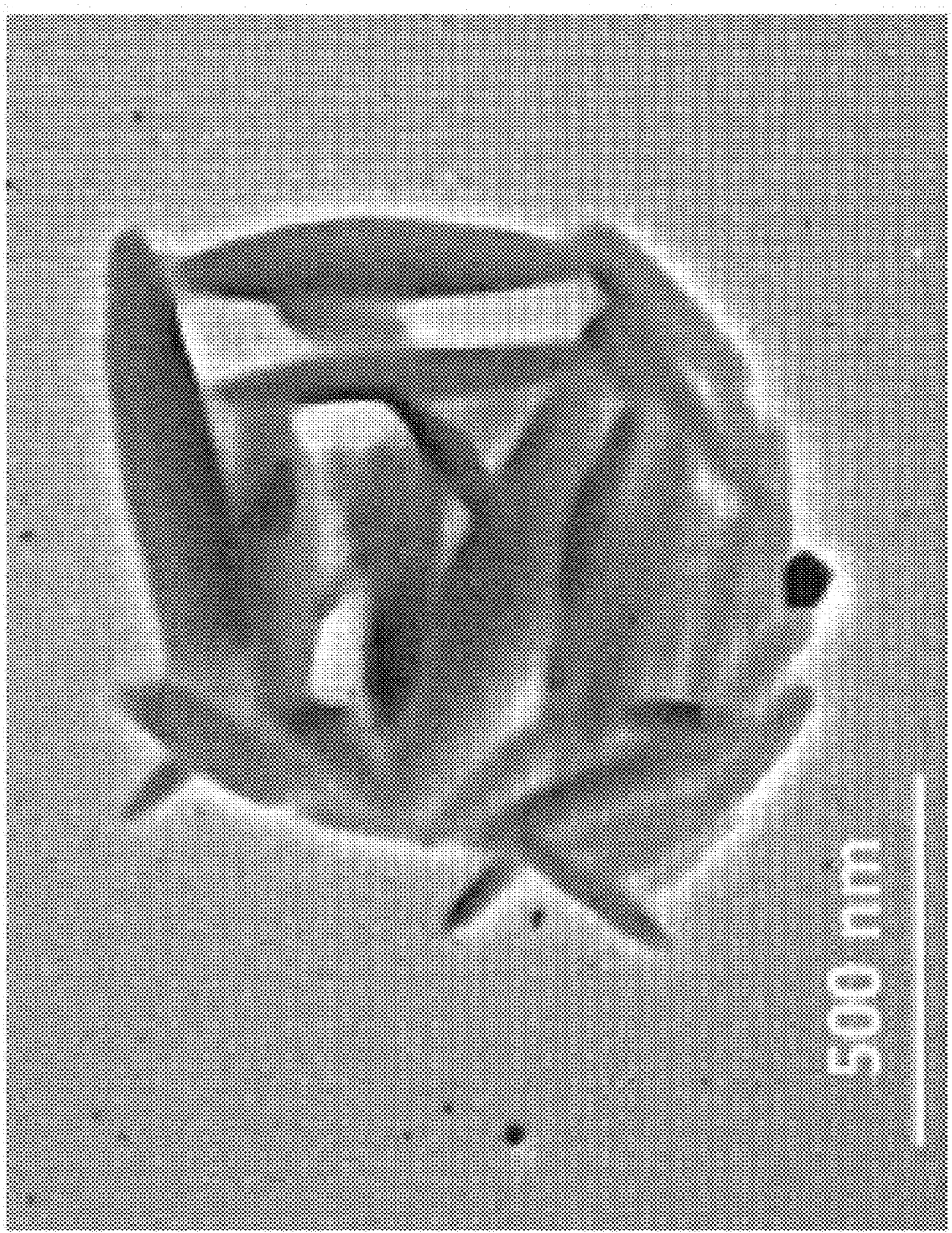
FIG. 8. This is the TEM picture of the indomethacin microparticles obtained in the step 2 in Comparative Example A1 of the present invention.
Figure 11:
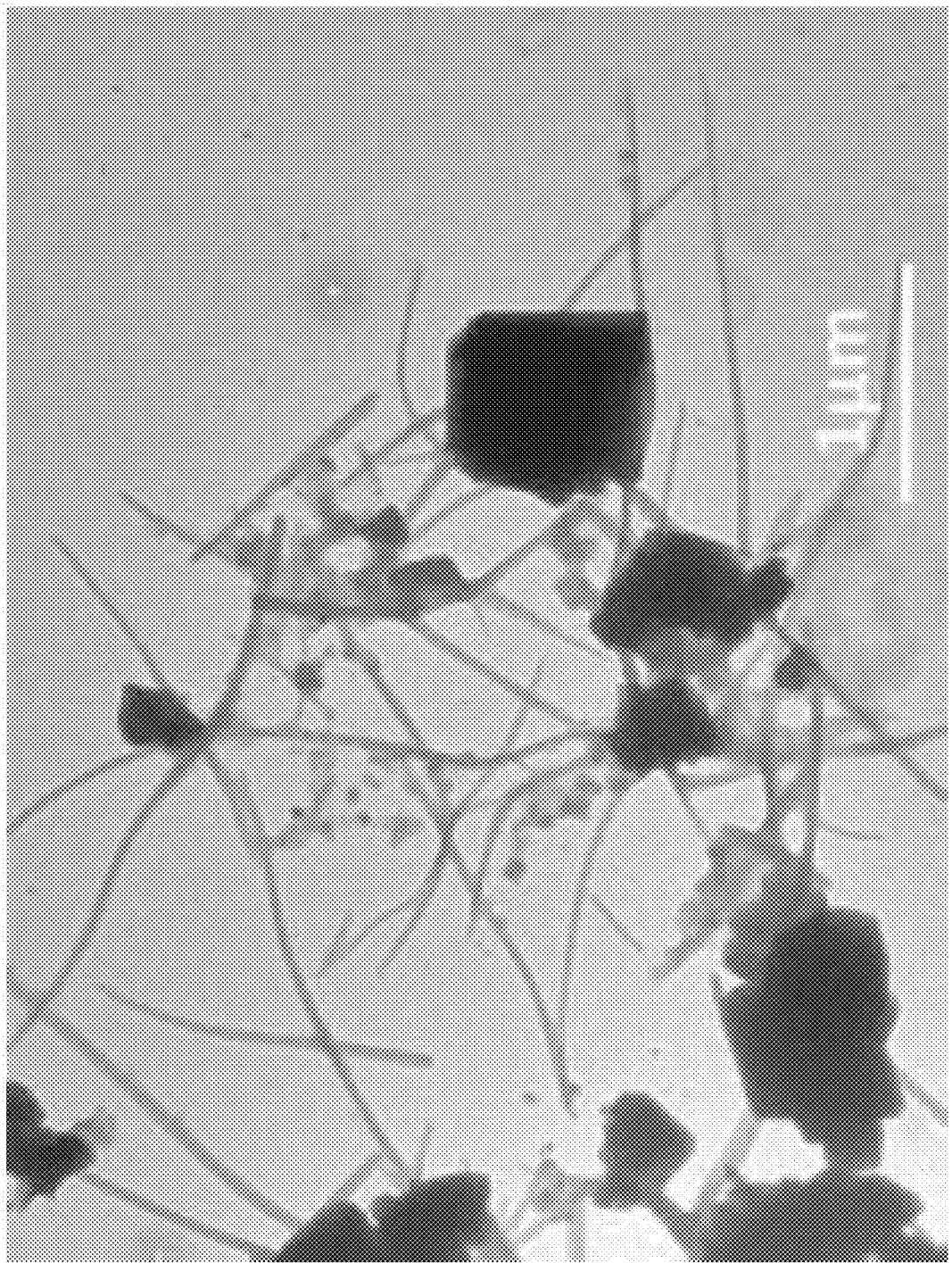
FIG. 11. This is the TEM picture of the indomethacin microparticles obtained in the step 2 in Comparative Example A2 of the present invention.

For example, in FIG. 8 and FIG. 11 showing the results of Comparative Examples A of the present invention, it was confirmed the way how the particles grow in the solvent and cause necking. Once the state like this is resulted, the particles cannot be dispersed even if the dispersion treatment is carried out thereafter; and thus, it is very difficult to express the characteristics to be obtained by making the organic material to microparticles (for example, change in physical properties such as improvement of solubility, change in the optical properties such as improvement of transparency, and change in chemical properties such as novel reaction, etc.).

Figure 29:
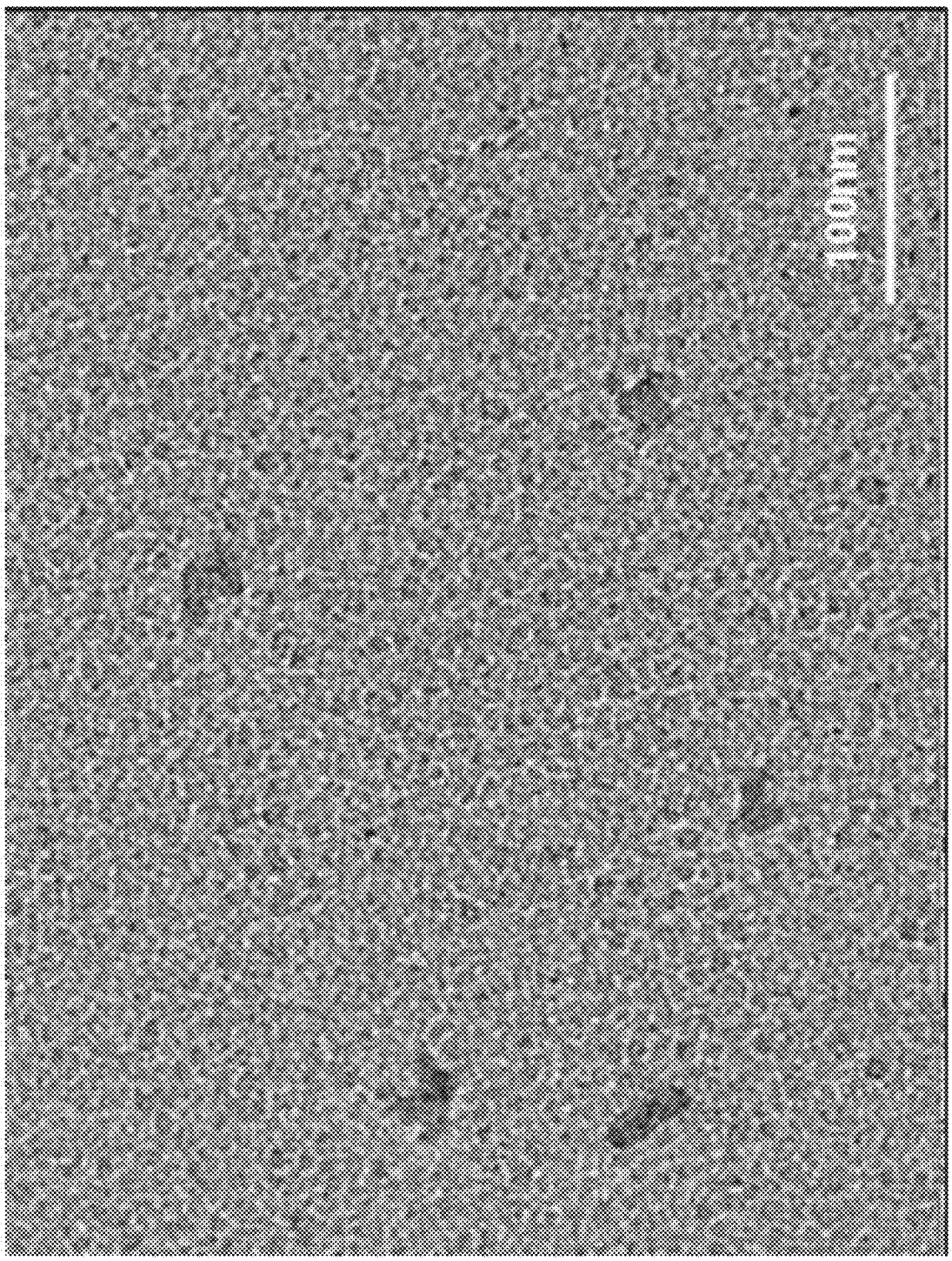
FIG. 29. This is the picture observed with the transmission electron microscope (TEM) of the red pigment nanoparticles of the present invention produced in the step 1 of Experiment No. 1-1 of Examples B.
Figure 31:
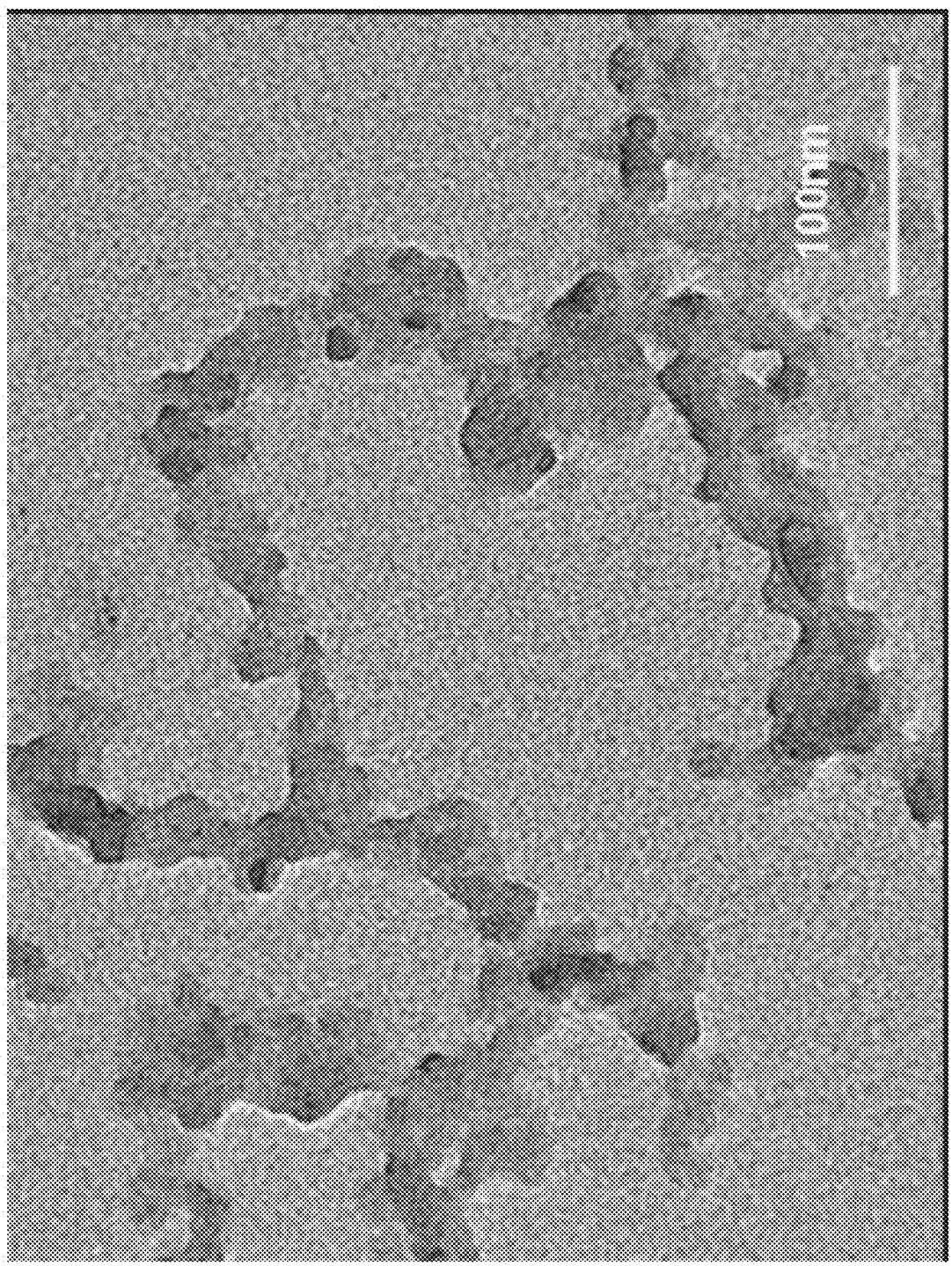
FIG. 31. This is the picture observed with the transmission electron microscope (TEM) of the red pigment nanoparticles of the present invention produced in the step 2 of Experiment No. 1-1 of Examples B.
Figure 32:
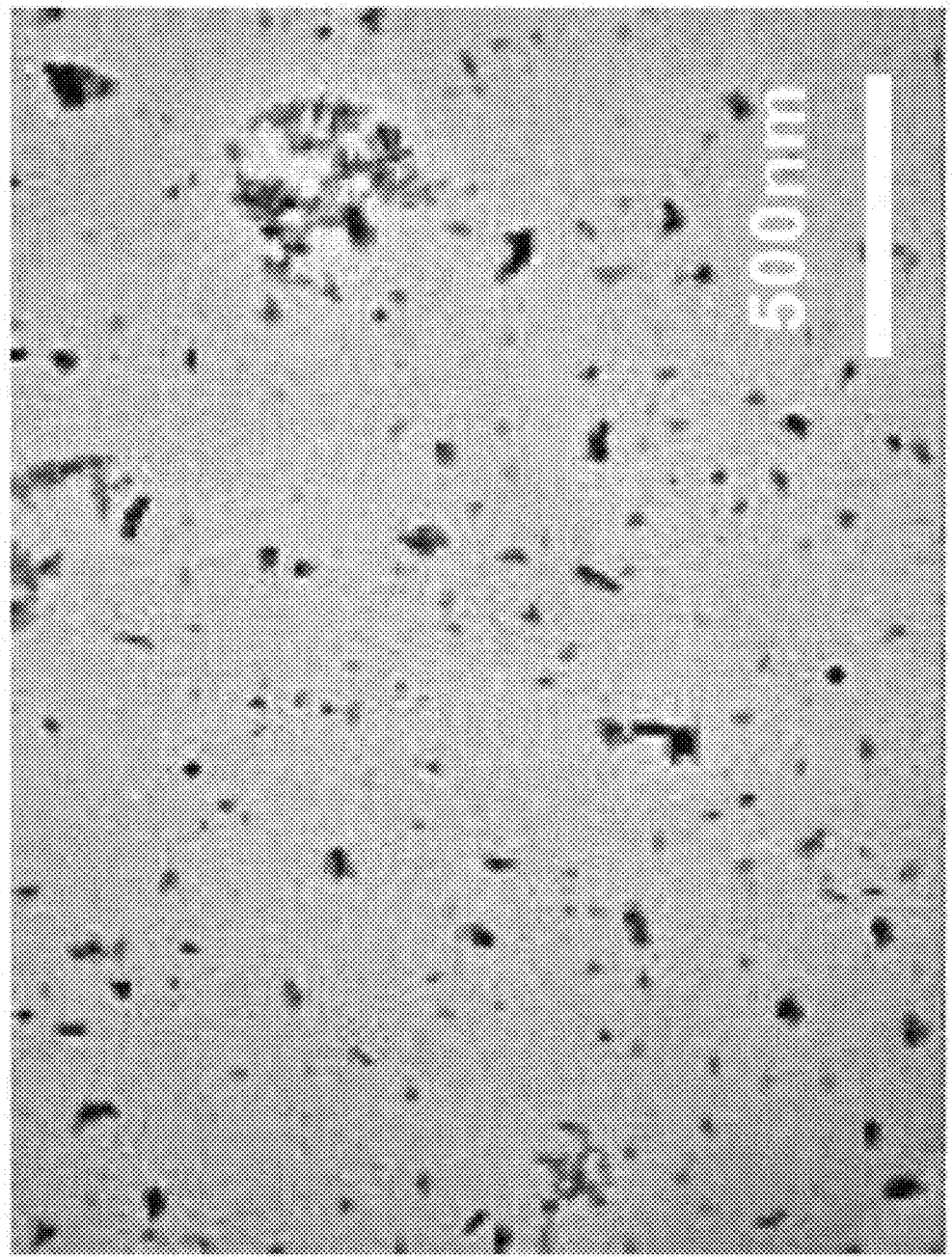
FIG. 32. This is the picture observed with the transmission electron microscope (TEM) of the blue organic pigment microparticles of the present invention obtained after the step 1 (washing) of Experiment No. 1-7 of Examples C.
Figure 33:
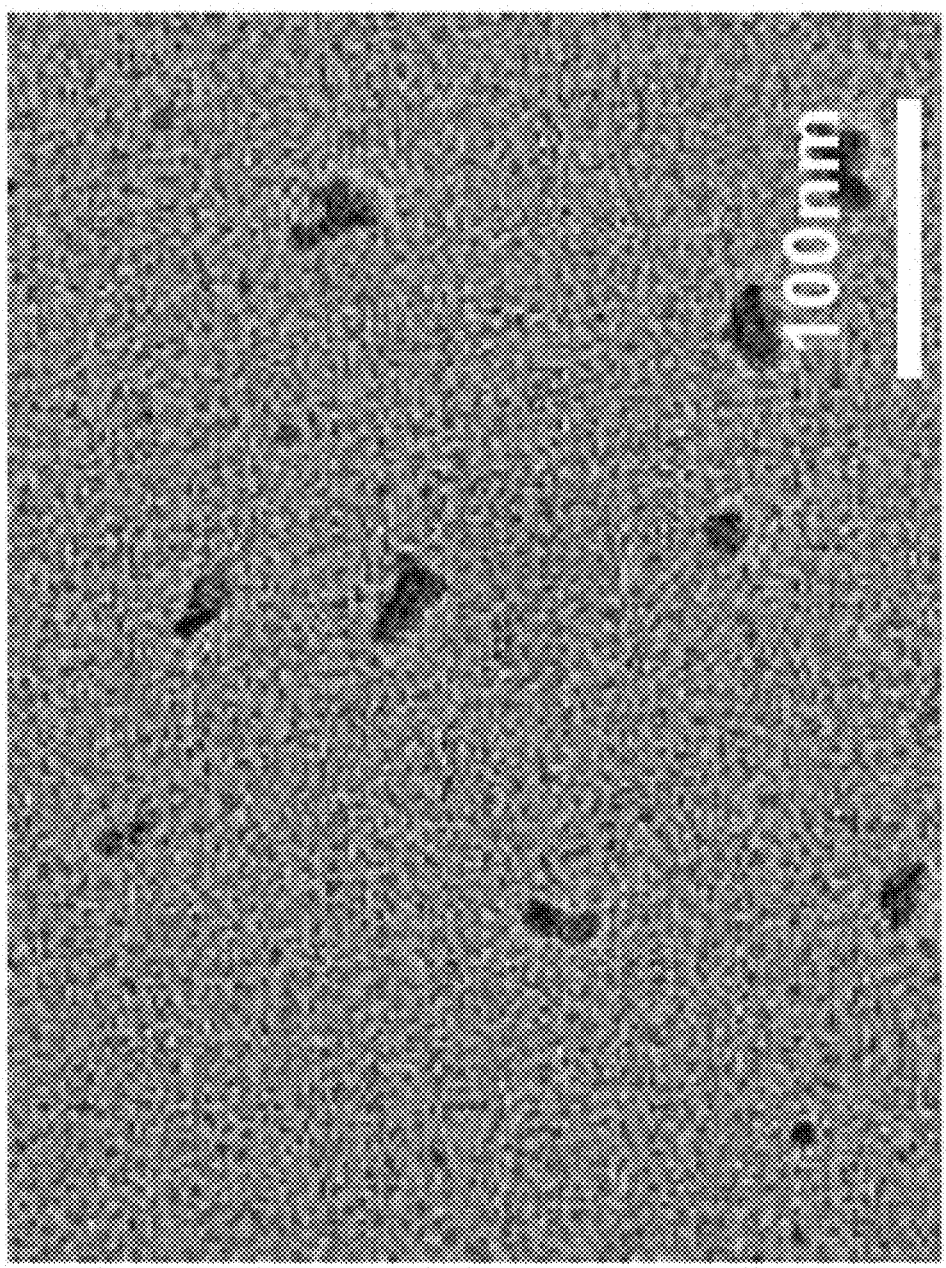
FIG. 33. This is the picture observed with the transmission electron microscope (TEM) of the blue organic pigment microparticles of the present invention obtained after the step 1 (washing) of Experiment No. 1-7 of Examples C.
Figure 34:
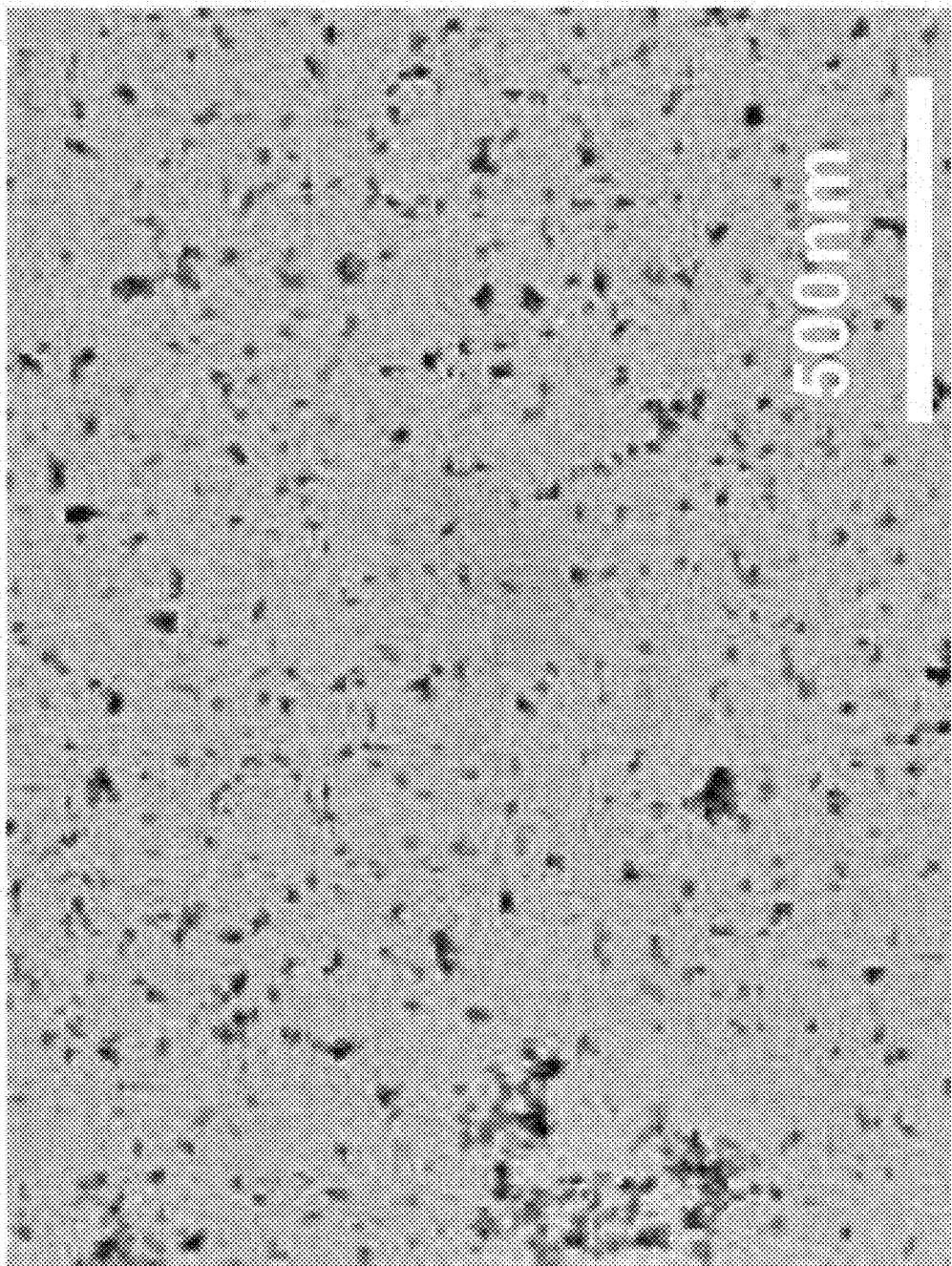
FIG. 34. This is the picture observed with the transmission electron microscope (TEM) of the blue organic pigment microparticles of the present invention obtained after the step 2 (action) of Experiment No. 1-7 of Examples C.
Figure 35:
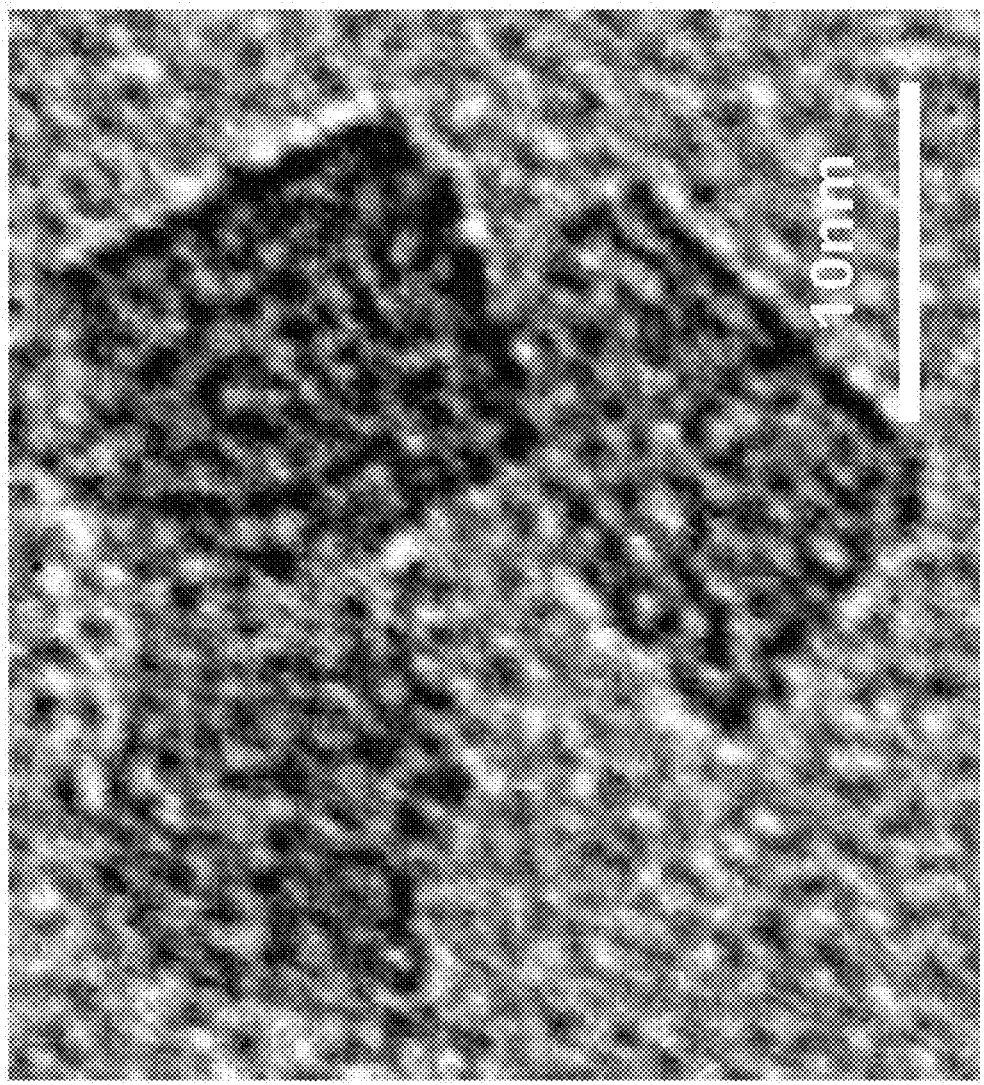
FIG. 35. This is the picture observed with the transmission electron microscope (TEM) of the blue organic pigment microparticles of the present invention obtained after the step 2 (action) of Experiment No. 1-7 of Examples C.

As one other example, the TEM observation result of the red pigment PR254 microparticles produced by Experiment No. 1-1 of Examples B of the present invention is shown in FIG. 31, the picture being taken when the said microparticles are introduced into propylene glycol monomethyl ether acetate (PGMEA). Also, the TEM observation result of the same before the said microparticles are introduced thereinto is shown in FIG. 29 (this is dispersed in the surfactant-containing aqueous solution). It can be confirmed that as compared with the PR254 nanoparticles shown in FIG. 29, the PR254 nanoparticles shown in FIG. 31 grow in PGMEA and cause necking. Once the state like this is resulted, the nanoparticles thereof cannot be dispersed even if the dispersion treatment is carried out thereafter; and thus, it is very difficult to express the fine characteristics of the red pigment.

Also, it can be confirmed that the copper-titanyl-cobalt phthalocyanine microparticle that is the blue pigment produced by Experiment No. 4-4 of Examples C of the present invention (FIG. 36) or the copper phthalocyanine microparticle that is the blue pigment produced by Experiment No. 3-1 (FIG. 37) grows in the above-mentioned solvent and causes necking, both microparticles being produced as further examples. Once the state like this is resulted, the particles thereof cannot be dispersed even if the dispersion treatment is carried out thereafter; and thus, it is very difficult to express the characteristics of the blue organic pigment microparticle.

In the present invention, it is important that the organic material microparticle before being subjected to the action of the particle property control solution have an amorphous portion at least in part thereof, and that the solvent which has a partial dissolvability to the organic material microparticle be daringly selected, and that the particle property control solution that is prepared by adding the before-mentioned surfactant to the said solvent, specifically, by mixing, dissolving, or molecular-dispersing them be made to act to the organic material microparticle. By so doing, properties of the organic material microparticle, such as particle diameter, crystal type, and crystallinity, can be controlled.

Although the controlling mechanism of the particle properties is not clear, molecules of the amorphous portion of the organic material microparticle are randomly distributed in the solid state, and therefore the molecules do not reside densely among them as compared with the crystalline portion, so that binding forces among the molecules are weak. Presumably because of this, the amorphous portion of the organic material microparticle is prone to dissolve by action of the solvent which has a partial dissolvability to the organic material microparticle, thereby readily generating starting points of growth and necking of the said microparticles.

Although the organic material microparticle is prone to cause necking and particle growth when part thereof is dissolved in the solvent by the effects of the solvent and heat, if it is kept under such conditions, both the crystal transition and increase in the degree of crystallinity can take place simultaneously. Such changes accompany the change of the primary particle diameter of the organic material microparticle with the magnification of several tens to several hundreds; and therefore, the organic material microparticle thus coarsened is resulted in loss of the characteristics expected as the organic material microparticle. One effect of the surfactant in the present invention is to suppress and control the growth of the organic material microparticle. The above-mentioned surfactant suppresses dissolution of the organic material microparticle (especially the amorphous portion thereof) due to the action of the solvent which has a partial dissolvability to the organic material microparticle, so that the actions to the organic material microparticle such as necking and particle growth can be suppressed and controlled. More specifically, presumably, in the presence of the surfactant, the amorphous portion of the organic material microparticle does not reach the state of complete dissolution by the solvent having a partial dissolvability, but the random molecular arrangement of the amorphous portion thereof does change to cause compaction, thereby resulting in crystal transition and increase in the degree of crystallinity.

Another effect of the surfactant is to increase in the dissolvability of the solvent to the organic material microparticle. More specifically, wettability of the entire particles after having been acted by the surfactant can be enhanced. That is to say, the surfactant has an effect to give different properties to the organic material microparticle in accordance with the kind thereof, combination thereof with the solvent, etc. Therefore, the particle property control solution may be prepared by adding the surfactant which can enhance the solubility of the said solvent to the organic material microparticle into the solvent which has a partial dissolvability to the organic material microparticle. Further effect of the surfactant resides in that it can serve as the template at the time of the change in the crystal type of the organic material microparticle, more specifically, the template of the particle diameter of the organic material microparticle.

The present invention can be considered that by multiplying the above-mentioned effects, especially the amorphous portion of the organic material microparticle is made compact with controlling the growth of the organic material microparticle, so that the crystallinity thereof is enhanced thereby achieving the control of the crystal type transition as well as the crystallinity thereof.

As described above, in the present invention, the particle properties such as particle diameter, crystallinity, and crystal type of the organic material microparticle is controlled by making the particle property control solution act to the organic material microparticle. Specifically, operation of the above-mentioned action includes mixing of the organic material microparticle with the particle property control solution and/or stirring them, and mere contacting or spraying of the said solution; with such operations, properties of the organic material microparticle can be controlled by changing the kind of the solvent and surfactant, the concentration of the solution, the treating temperature, the stirring method, etc. In addition, the solvent having a partial dissolvability can be prepared by containing an acidic substance, a basic substance, or a neutral substance to be described later in the solvent.

These substances are not particularly restricted, while illustrative example of the acidic substance includes inorganic acids such as aqua regia, hydrochloric acid, nitric acid, fuming nitric acid, sulfuric acid, and fuming sulfuric acid; and organic acids such as formic acid, citric acid, malic acid, acetic acid, chloroacetic acid, dichloroacetic acid, oxalic acid, trifluoroacetic acid, and trichloroacetic acid. Illustrative example of the basic substance includes metal oxides such as sodium hydroxide and potassium hydroxide; metal alkoxides such as sodium methoxide and sodium isopropoxide; and amine compounds such as triethylamine, diethylamino ethanol, and diethylamine. Further, neutral substances such as slats of the acidic substances and the basic substances that are exemplified above may be mixed therewith.

Especially in the case of organic pigments such as the red organic pigment and blue organic pigment, the present invention can be executed without including a pigment derivative that is generally used in order to suppress the crystal growth. Therefore, the merit that the color inherent to the derivative does not affect the color development of the actually used organic pigment can be realized. However, the execution with addition of such derivative is not excluded.

Meanwhile, the concentration of the organic material microparticle that is to be acted to the solvent which has a partial dissolvability to the organic material microparticle is not particularly restricted, while the concentration thereof is generally in the range of 0.001 to 90.00% by weight, preferably in the range of 0.001 to 50.00% by weight, while more preferably in the range of 0.01 to 40.00% by weight. The concentration of the surfactant relative to the organic material microparticle is generally in the range of 0.01 to 500% by weight, preferably in the range of 0.1 to 300% by weight, while more preferably in the range of 1.0 to 100% by weight.

In the present invention, there is no particular restriction in the particle diameter of the organic material microparticle, while the particle diameter of the organic material microparticle before control of the particle properties of the organic material microparticle is preferably in the range of 1000 nm or less, more preferably 500 nm or less, while still more preferably in the range of 200 nm or less.

In the organic pigments such as the blue organic pigment, the primary particle diameter of the fine particles is generally in the range of 500 nm or less, preferably in the range of 100 nm or less, while still more preferably 30 nm or less. The shape of the particle or the microparticle is not particularly restricted, while these may be particles or the aggregate having the shapes such as a quasi-cylindrical column, a quasi-sphere, a quasi-disk, a quasi-triangular prism, a quasi-square pillar, a quasi-polygonal, and an elliptical sphere.

Meanwhile, the particle diameters measured before and after the action of the present invention is defined as the particle diameters measured before and after the operation such as mixing the organic material microparticle with the particle property control solution and/or stirring them, and mere contacting or spraying of the said solution.

In the present invention, the range in which the particle diameter of the organic material microparticle does not substantially change is defined as the range in which the rate of change in the particle diameter of the organic material microparticles measured before and after the solvent having a partial dissolvability to the organic material microparticle and having the surfactant added therein is made to act to the organic material microparticle (after the surfactant treatment (A)/before the surfactant treatment (B)) is 1 to 4.

The present invention comprises the step 1 in which, in order to separate the organic material microparticle from the raw material solution of the organic material microparticle, a separating solvent L for separating at least one kind of the organic material particles is mixed with a raw material solution of the organic material microparticle, this solution having the raw material of the organic material microparticle dissolved or molecular-dispersed therein, thereby effecting separation of the organic material microparticle (P1). The raw material to be used for the organic material microparticle may be the organic materials as described above as well as newly synthesized materials. The above-mentioned mixing method may be, for example, the one using a microreactor with the type of a forced thin film as described in Patent Document 5, or the mixing may be conducted by appropriately using publicly known methods in organic material microparticles. The present invention may be executed in such a way that a good solvent capable of dissolving or molecular-dispersing the raw material of the organic material microparticle is mixed with the said raw material of the organic material microparticle so as to prepare the raw material solution, and a solvent having a lower solubility to the organic material than the good solvent is used as the separating solvent L of the organic material microparticle. Alternatively, the present invention may be executed by controlling a pH at the time of mixing of the raw material solution of the organic material microparticle with the separating solvent L of the organic material microparticle. As the case may be, by combining the solvent with an acidic substance or a basic substance, the pH may be controlled as well.

In addition, as the case may be, the present invention may comprise the step c in which washing and/or solvent substitution is conducted to the organic material microparticle (P1) obtained in the step 1. This step c in which washing and/or solvent substitution is conducted may be executed by using publicly known methods as appropriately. Though not particularly restricted, to the solution containing the organic material microparticle, washing and/or solvent substitution of the organic material microparticle can be conducted by the operation such as filtration, centrifugal separation, and ultrafiltration, with proper selection of the solvent in accordance with the purpose thereof.

The present invention is characterized by that properties of the organic material microparticle is controlled by including the step 2 in which the particle property control solution is made to act to the organic material microparticle (P1). With regard to the property control, increase of the particle diameter of the organic material microparticle and/or enhancement of the crystallinity of the organic material microparticle may be mentioned. With regard to the crystallinity of the organic material microparticle, the degree of crystallinity of the organic material microparticle may be mentioned. The property control of the particle referred herein is not limited to the above-mentioned content so far as growth of the particle in the solvent or necking can be suppressed; and thus, this control includes the case that the organic material microparticle undergoes the crystal transition. In addition, by separating the microparticles in such a way that the crystallinity thereof may be low so as to contain the amorphous portion, particle properties such as the crystal type and the degree of crystallinity can be controlled more precisely in the step 2. By so doing, the present invention can be made more effective.

Illustrative example of the action in the step 2 includes mixing, contacting, and spraying. In the step 2 of the present invention, the said action may be conducted once, or plural times (for example, twice, three times, four times, etc.).

In the step 2 of the present invention, if a stirring treatment is included (hereunder, this treatment is sometimes referred to as dispersion treatment by stirring, or dispersion treatment), properties of the organic material microparticle can be controlled by means of a stirring energy, wherein the stirring energy may be controlled with a method using publicly known stirring equipment and stirring means. Meanwhile, detailed description of the stirring energy can be found in the Japanese Patent Laid-Open Publication No. H04-114725 filed by the present applicant.

The stirring method of the present invention is not particularly restricted. The stirring may be conducted with a method using a magnetic stirrer and a stirring bar. The stirring may also be conducted by using a stirrer, a dissolver, an emulsifier, a disperser, a homogenizer, etc. with various shearing methods, a friction method, a high pressure jet method, an ultrasonic method, etc. Illustrative example thereof includes continuous emulsifiers such as Ultra Turrax (manufactured by IKA Corp.), Polytron (manufactured by KINEMATICA AG), TK Homomixer (manufactured by PRIMIX Corp.), Ebara Milder (manufactured by EBARA Corp.), TK Homomic Line Flow (manufactured by PRIMIX Corp.), Colloid Mill (manufactured by Shinko Pantech Co., Ltd.), Slusher (manufactured by Nippon Coke & Engineering Co., Ltd.), Trigonal Wet-Type Fine Grinding Mill (manufactured by Mitsui Miike Machinery Co., Ltd.), Cavitron (manufactured by Eurotech Co., Ltd.), and Fine Flow Mill (manufactured by Pacific Machinery & Engineering Co., Ltd.); and batch or continuous apparatuses such as Clearmix (manufactured by M. Technique Co., Ltd.), Clearmix Dissolver (manufactured by M. Technique Co., Ltd.), Clearmix Double Motion (manufactured by M. Technique Co., Ltd.), and Filmix (manufactured by PRIMIX Corp.). In addition, there is a case that a partial treatment with microwave before or after the stirring is effective.

The particle growth can take place via two ways. Namely, in one case, particles aggregate among themselves and dissolve at the crystal surface thereof, thereby leading to the growth and coarsening thereof, while in other case, coarsening of the particles takes place from a portion that is dissolved in the dispersion medium. Effect of the surfactant is to protect the particle surface so as to suppress the growth thereof; however, if the particles form aggregates, the surfactant cannot effectively express its function in a certain case. Because of this, the dispersion treatment by stirring can be effective. In this method, the surfactant is uniformly mixed for the reaction with the solvent which has a partial dissolvability to the organic material microparticle; and thus, it is preferable to carry out the stirring treatment. Further, at the time when the particle property control solution is made to act to the organic material microparticle, too, it is preferable to carry out the stirring treatment. In this occasion, by the stirring energy applied to the system, the surfactant as well as the solvent which has a partial dissolvability to the organic material microparticle can be made to act to the organic material microparticle effectively. In the case that the stirring treatment is included in the step 2, the properties of the organic material microparticle (degree of crystallinity, crystal type, and particle diameter) can be controlled by means of the stirring energy.

Hereinafter, as one example, the production process of the organic material microparticle according to a batch method (step 0 to 2) will be explained along FIG. 1.
(Step 0)

The separating solvent of the organic material microparticle (A solution: this corresponds to the separating solvent L of the organic material microparticle) and the raw material solution of the organic material microparticle (B solution) were prepared.
(Step 1)

Mixing of the A solution and B solution: the B solution was introduced into the A solution with stirring the A solution by means of a magnetic stirrer and a stirring bar so as to effect the separation of the organic material microparticles.
(Step 2)

The slurry of the organic material microparticles separated in the step 1, or the wet cake or the dried powder of the same was introduced into the particle property control solution, and then, the resulting mixture was subjected to the stirring treatment.

Alternatively, the embodiment may be employed wherein the slurry containing the organic material microparticles that are separated in the step 1 is filtrated, followed by washing the microparticles with a washing solution (step c), and thereafter, the wet cake of the organic material microparticles or the dried powder of the organic material microparticles obtained by a drying treatment such as by a vacuum drying method is produced, and then, the wet cake or the dried powder thus obtained is introduced into the particle property control solution in the step 2 whereby carrying out the stirring treatment.

Next, hereinafter, as another example, the production process (step 0 to 2) of the organic material microparticle by using a microreactor to be described later will be explained along FIG. 1.

(Step 0)

The separating solvent of the organic material microparticle (A solution) and the raw material solution of the organic material microparticle (B solution) were prepared.

(Step 1)

Figure 2:
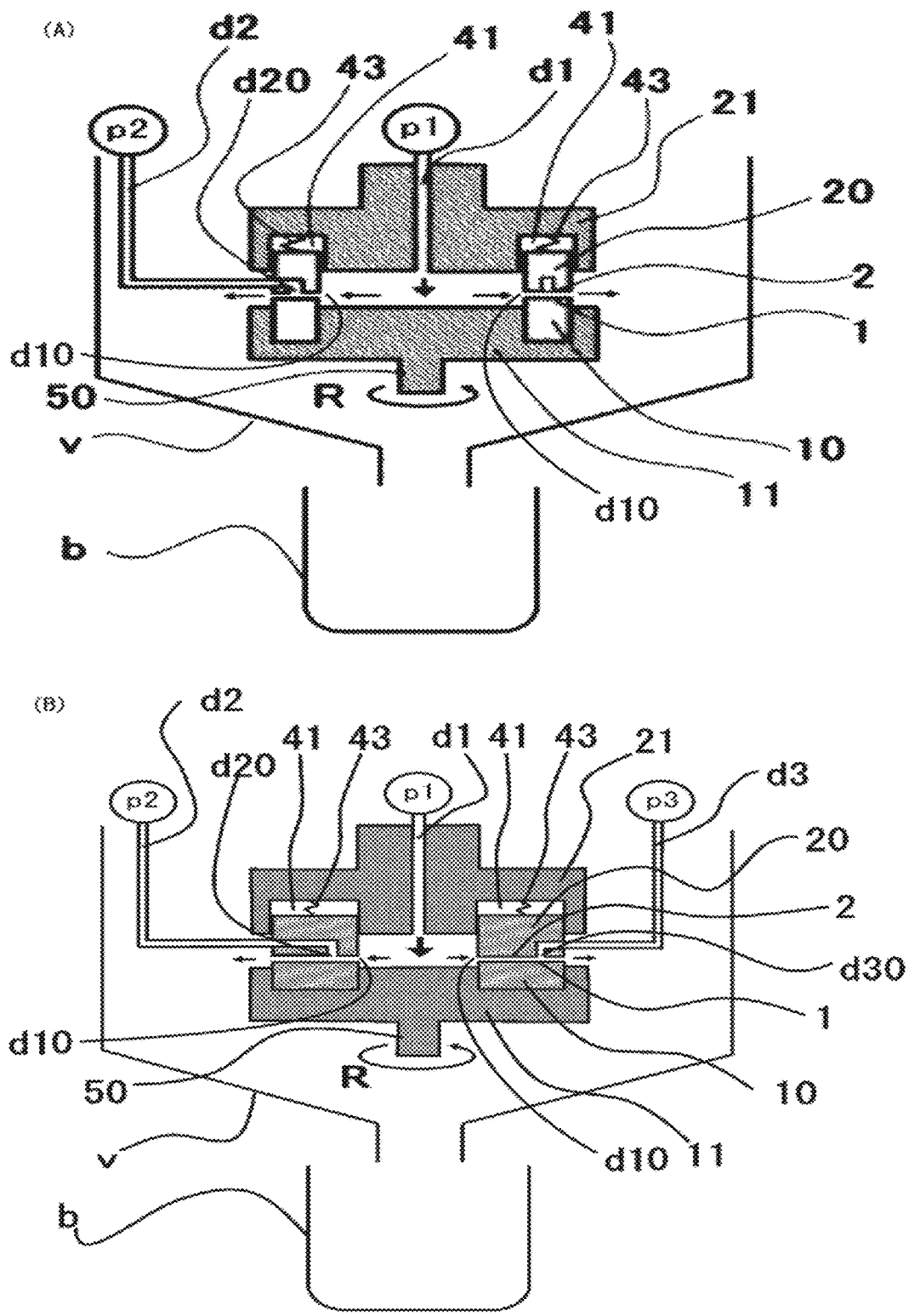
FIG. 2 (A) shows a rough cross-sectional view of the microreactor with the type of a forced thin film according to embodiments of the present invention.

By using the microreactor shown in FIG. 2 (A), the raw material solution of the organic material microparticle (B solution) and the separating solvent of the organic material microparticle (A solution: this corresponds to the separating solvent L to separate the organic material microparticle) were mixed so as to effect the separation of the organic material microparticle. Meanwhile, as for the A solution and B solution, besides those exemplified in EXAMPLES to be described later, those described in Patent Document 8, as well as publicly known examples of mixing and separation may be used.

(Step 2)

The slurry of the organic material microparticles separated in the step 1, or the wet cake or the dried powder of the same was introduced into the particle property control solution, and then, the resulting mixture was subjected to the stirring treatment.

Alternatively, the embodiment may be employed wherein the slurry containing the organic material microparticles that are separated in the step 1 is filtrated, followed by washing the microparticles with a washing solution (step c), and thereafter, the wet cake of the organic material microparticles or the dried powder of the organic material microparticles obtained by a drying treatment such as by a vacuum drying method is produced, and then, the wet cake or the dried powder thus obtained is introduced into the particle property control solution in the step 2 whereby carrying out the stirring treatment.

Meanwhile, as the microreactor, the one shown in FIG. 2, which is the same as the apparatuses described in Patent Document 4 to Patent Document 6, can be used. Hereunder, the microreactor will be described in detail. In FIG. 2 (A), FIG. 2 (B), and FIG. 3, the reference character R indicates a rotational direction.

The microreactor of the present embodiment is provided with two processing members of a first processing member 10 and a second processing member 20 arranged opposite to each other, wherein the first processing member 10 rotates. The surfaces arranged opposite to each other of the respective processing members 10 and 20 are made to be the respective processing surfaces. This apparatus is the microreactor with the type of a forced thin film, wherein the first processing member 10 is provided with a first processing surface 1 and the second processing member 20 is provided with a second processing surface 2.

Each of the processing surfaces 1 and 2 is connected to a flow path d1 and a flow path d2 of the fluids to be processed, respectively, thereby constituting part of the flow paths of the fluids to be processed. Distance between these processing surfaces 1 and 2 is controlled so as to form a minute space usually in the range of 1 mm or less, for example, in the range of about 0.1 to 50 μm. With this, the fluids to be processed passing through between the processing surfaces 1 and 2 become a forced thin film fluid forced by the processing surfaces 1 and 2.

Then, this apparatus performs a fluid processing in which the first and second fluids to be processed are made to react with each other so as to separate the microparticles between the processing surfaces 1 and 2.

To more specifically explain, this apparatus is provided with a first holder 11 for holding the first processing member 10, a second holder 21 for holding the second processing member 20, a surface-approaching pressure imparting mechanism 43, a rotation drive mechanism (not shown in drawings), a first introduction part d1, a second introduction part d2, a fluid pressure imparting mechanism p1, and a fluid pressure imparting mechanism p2. The fluid pressure imparting mechanisms p1 and p2 can be compressors or other pumps.

In the above-mentioned embodiment, the first processing member 10 and the second processing member 20 are disks with ring forms. Material of the processing members 10 and 20 can be not only metal but also carbon, ceramics, sintered metal, abrasion-resistant steel, sapphire, and other metal subjected to hardening treatment, and rigid material subjected to lining, coating, plating, or the like. In the processing members 10 and 20 of the above-mentioned embodiment, the first and the second surfaces 1 and 2 arranged opposite to each other are mirror-polished, and an arithmetic average roughness thereof is in the range of 0.01 to 1.0 μm.

In the above-mentioned embodiment, the second holder 21 is fixed to the apparatus, wherein the first holder 11 attached to a rotary shaft of the rotation drive mechanism fixed to the same apparatus rotates, and thereby the first processing member 10 attached to this first holder 11 rotates relative to the second processing member 20. As a matter of course, the second processing member 20 may be made to rotate, or the both may be made to rotate. In the present invention, the rotation can be set to a speed of, for example, in the range of 350 to 3600 rpm.

In the above-mentioned embodiment, the second processing member 20 approaches to and separates from the first processing member 10 in the direction of the rotary shaft 50, wherein a side of the second processing member 20 opposite to the second processing surface 2 is accepted in an accepting part 41 arranged in the second holder 21 so as to be able to rise and set. However, in contrast to the above, the first processing member 10 may approach to and separate from the second processing member 20, or both the processing members 10 and 20 may approach to and separate from each other.

The above-mentioned accepting part 41 is a concave portion for accepting the side of the second processing member 20 opposite to the second processing surface 2, and this concave portion is a groove being formed into a ring. This accepting part 41 accepts the second processing member 20 with sufficient clearance so that the side of the second processing member 20 opposite to the second processing surface 2 may rise and set.

The surface-approaching pressure imparting mechanism is a mechanism to generate a force (hereinafter, surface-approaching pressure) to press the first processing surface 1 of the first processing member 10 and the second processing surface 2 of the second processing member 20 in the direction to make them approach each other. The mechanism generates a thin film fluid having minute thickness in a level of nanometer or micrometer while keeping the distance between the processing surfaces 1 and 2 in a predetermined minute distance by the balance between the surface-approaching pressure and the force due to the fluid pressure to separate the processing surfaces 1 and 2 from each other. In the above-mentioned embodiment, the surface-approaching pressure imparting mechanism supplies the surface-approaching pressure by biasing the second processing member 20 toward the first processing member 10 by a spring 43 arranged in the second holder 21. In addition, the first fluid to be processed which is pressurized with the fluid pressure imparting mechanism p1 is introduced from the first introduction part d1 into the space inside the processing members 10 and 20.

On the other hand, the second fluid to be processed which is pressurized with the fluid pressure imparting mechanism p2 is introduced from the second introduction part d2 via a path arranged inside the second processing member 20 to the space inside the processing members 10 and 20 through an opening d20 famed in the second processing surface.

At the opening d20, the first fluid to be processed and the second fluid to be processed converge and mix with each other. At this time, the mixed fluid to be processed becomes a forced thin film fluid by the processing surfaces 1 and 2 that keep the minute space therebetween, whereby the fluid is forced to move out from the circular, processing surfaces 1 and 2. The first processing member 10 is rotating; and thus, the mixed fluid to be processed does not move linearly from inside the circular, processing surfaces 1 and 2 to outside thereof, but does move spirally from the inside to the outside thereof by a resultant vector acting on the fluid to be processed, the vector being composed of a moving vector toward the radius direction of the circle and a moving vector toward the circumferential direction.

Figure 3:
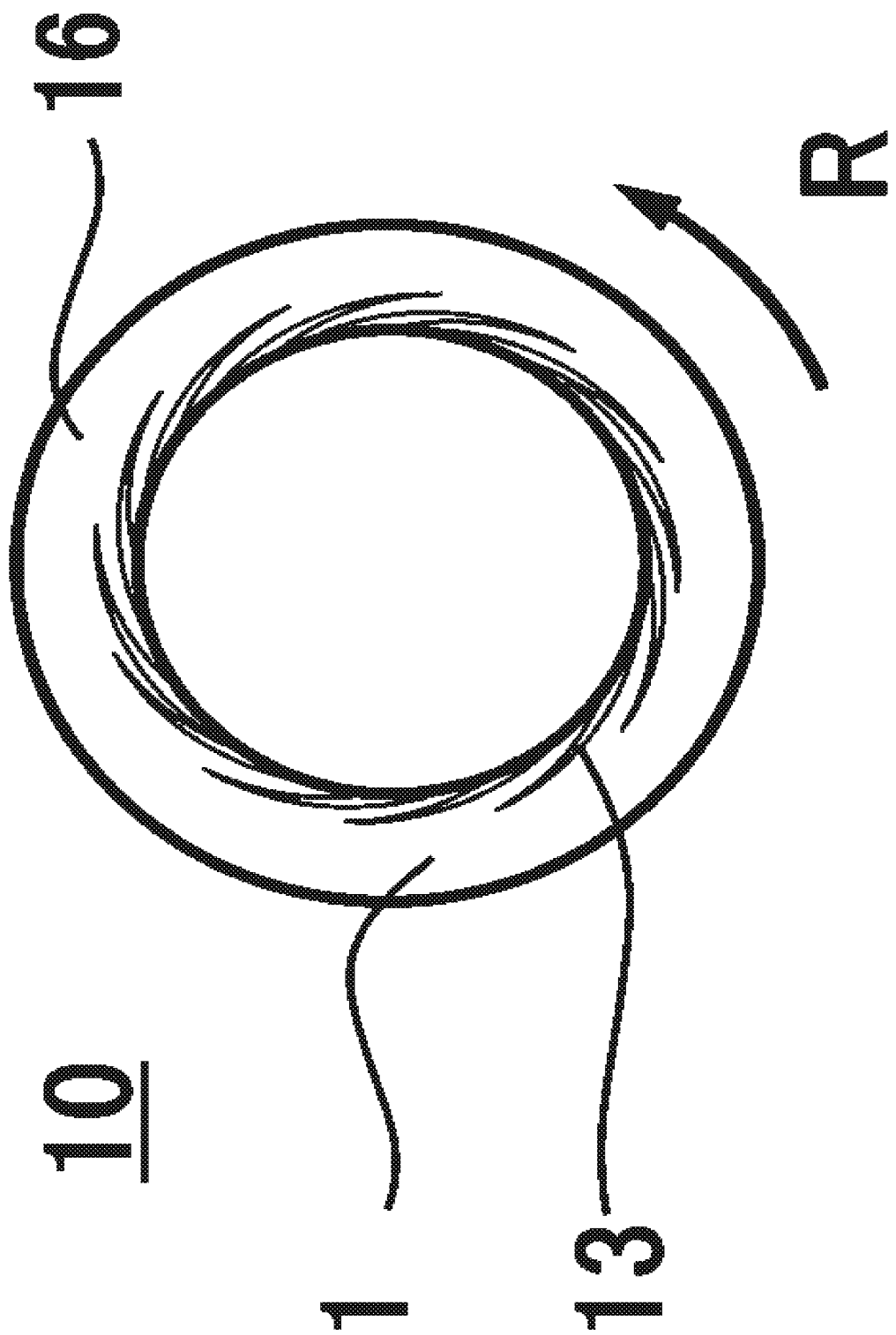
FIG. 3 This shows a rough plan view of the first processing surface of the microreactor with the type of a forced thin film shown in FIG. 2 (A) and FIG. 2 (B).

Here, as shown in FIG. 3, in the first processing surface 1 of the first processing member 10, a groove-like depression 13 extended toward an outer side from the central part of the first processing member 10, namely in a radius direction, may be formed. The depression 13 may be, as a plane view, curved or spirally extended on the first processing surface 1, or, though not shown in the drawing, may be extended straight radially, or bent at a right angle, or jogged; and the concave portion may be continuous, intermittent, or branched. In addition, this depression 13 may be formed also on the second processing surface 2, or on both the first and second processing surfaces 1 and 2. By forming the depression 13 in the manner as mentioned above, the micro-pump effect can be obtained so that the fluid to be processed may be sucked into between the first and second processing surfaces 1 and 2.

It is preferable that the base edge of the depression 13 reach the inner periphery of the first processing member 10. The front edge of the depression 13 is extended to the direction of the outer periphery of the first processing surface 1; the depth thereof is made gradually shallower (smaller) from the base edge to the front edge. Between the front edge of the depression 13 and the outer peripheral of the first processing surface 1 is formed a flat plane not having the depression 13.

The opening d20 described above is arranged preferably in a position opposite to the flat surface of the first processing surface 1. By so doing, mixing of a plurality of fluids to be processed and separation of the microparticles therefrom can be effected under the condition of a laminar flow.

In addition, the fluid discharged to outside the processing members 10 and 20 is collected via a vessel v into a beaker b as a discharged solution. In the embodiment of the present invention, the discharged solution contains the organic material microparticles, as to be described later.

In example A shown in FIG. 2 (A), although kinds of the fluid to be processed and numbers of the flow path are set two respectively, they may be three or more. The opening for introduction arranged in each processing member is not particularly restricted in its form, size, and number; and these may be changed as appropriate. The opening for introduction may be arranged just before the first and second processing surfaces 1 and 2 or in the side of further upstream thereof.

In the present invention, it is good enough only if the processing could be effected between the processing surfaces 1 and 2, and an embodiment may also be employed wherein the second fluid to be processed is introduced from the first introduction part d1 and the first fluid to be processed is introduced from the second introduction part d2. For example, the expression "first" or "second" for each fluid has a meaning for merely discriminating an $n^{th}$ fluid among a plurality of the fluids present; and therefore, a third or more fluids can also exist as described before.

In the production process of the organic material microparticle by using the microreactor (step 0 to step 2), the step 1 and the step (2) may be continuously conducted by using the microreactor. Specifically, as shown in FIG. 2 (B), besides the first introduction part d1 and the second introduction part d2, the third introduction part d3 is arranged in the microreactor; and for example, the raw material solution of the organic material microparticle is introduced as the first fluid from the first introduction part d1, the separating solvent of the organic material microparticle is introduced as the second fluid from the second introduction part d2, and the particle property control solution is introduced as the third fluid from the third introduction part d3; the respective fluids being separately introduced into the microreactor. In this case, the third introduction part d3 through which the particle property control solution is introduced is arranged in the downstream side of the first introduction part d1 and the second introduction part d2; and to be more specific, by arranging the opening d30 of the third introduction part d3 in the downstream side of the opening d20 of the second introduction part d2, the particle property control solution can act to the organic material microparticle separated between the processing surfaces 1 and 2. The microreactor provided with the three openings (d10, d20, and d30) is suitable when the step 1 and the step 2 are continuously conducted.

However, in execution of the present invention, in the case that the step 1 is conducted in the microreactor and the steps after the step 1 are conducted outside the microreactor, at least two openings (d10 and d20) are enough, as shown in FIG. 1 (A). However, in the case that the surface treatment is conducted in the thin film fluid onto the organic material microparticles separated between the processing surfaces 1 and 2, though not limited to this case, it does not preclude to conduct the step 1 by using the microreactor provided with three or more openings.

Especially when the above-mentioned microreactor is used, the organic material of the present invention can be produced as the microparticle, wherein the particle diameter thereof can be made in the range of 1000 nm or less, while preferably in the range of 500 nm or less, before and after the treatment with the solvent which has a partial dissolvability to the organic material microparticle and the surfactant capable of suppressing the growth of the organic material microparticle. In addition, when the above-mentioned microreactor is used, control of the crystallinity of the separated microparticle is comparatively easy; and thus, by separating the microparticle in the state of a low crystallinity containing the amorphous portion, the crystal type, the degree of crystallinity, and the like of the microparticles in the step 2 can be controlled more precisely. As the specific example of the microreactor like this, ULREA (manufactured by M. Technique Co., Ltd.) may be mentioned. However, the method for producing the organic material microparticle of the present invention is not limited to those using the microreactor.

EXAMPLES

Hereinafter, the present invention will be explained more specifically by means of Examples. However, the present invention is not limited to the following Examples. In the following Examples, the A solution is the first fluid to be processed that is introduced from the first introduction part d1 of the apparatus shown in FIG. 2 (A) and FIG. 2 (B); and the B solution is the second fluid to be processed that is introduced from the second introduction part d2 of the same apparatus.

In the present invention, all the Examples are separated into three groups of Examples A, Examples B, and Examples C, and they are shown together with respective Comparative Examples.

Examples A relate to the group of biologically ingestible substances and resins.
Examples B relate to the group of red organic pigments.
Examples C relate to the group of blue organic pigments.
Meanwhile, in the main body of the specification, the alphabetical group symbols of A, B, and C are tagged after respective Examples. However, in Tables and drawings, the alphabetical group symbols A, B, and C are omitted.

Group of Examples A

As examples of the method for producing the organic material microparticle of the present invention, explanation will be given by taking the microparticles of indomethacin in Examples A1 to A4, curcumin in Examples A5 and A6, polypropylene in Example A7, and pirenoxine in Example A8, respectively.

In Examples A, for the X-ray diffraction measurement (XRD measurement), the powder X-ray diffraction measurement apparatus (product name: X'Pert PRO MPD, manufactured by PANalytical B. V.) was used. The measurement conditions were as follows: measurement range of 10 to 60°, Cu anticathode, tube voltage of 45 kV, tube current of 40 mA, and scanning speed of 16°/min.

For the TEM observation, the transmission electron microscope JEM-2100 (manufactured by JEOL Ltd.) was used. The observation condition with the acceleration voltage of 80 kV was employed.

For the SEM observation, the scanning electron microscope JFM-7500F (manufactured by JEOL Ltd.) was used. The observation condition with the acceleration voltage of 1 kV was employed.

Evaluation of the particle diameter was made with the average value of 50 particles in the picture of the TEM observation or the SEM observation with the magnification of 25000 in the both observations.

Meanwhile, the degree of crystallinity mentioned here is defined as the ratio of the crystallized portion relative to the total of the crystallized portion and the amorphous portion.

Example A1: Indomethacin Microparticle

<Step 0: Preparation of the Separating Solvent of the Organic Material Microparticle (A Solution) and the Raw Material Solution of the Organic Material Microparticle (B Solution)>
<Preparation of the Separating Solvent of the Organic Material Microparticle (A Solution)>

By using a magnetic stirrer, a 0.1 mol/L aqueous hydrochloric acid solution was prepared as the separating solvent of indomethacin, the separating solvent of the organic material microparticle (A solution).
<Preparation of the Raw Material Solution of the Organic Material Microparticle (B Solution)>

Into a 0.35 mol/L aqueous sodium hydrogen carbonate solution were added indomethacin (gamma-type crystal) and polyvinyl pyrrolidone (Kollidon 12 PF; manufactured by BASF GmbH) so as to give the concentration of 0.2% by weight and 0.2% by weight, respectively, thereby the raw material indomethacin solution was prepared as the raw material solution of the organic material microparticle (B solution). The resulting mixture was stirred by using Clearmix (product name: CLM-2.2S, manufactured by M. Technique Co., Ltd.), a high-speed rotation type dispersing emulsifier, with the rotor's rotation number of 15000 rpm and the temperature of about 35° C. for the period of 30 minutes so as to prepare the uniform raw material indomethacin solution. In such a case that plural components are mixed or dissolved, it is preferable to use Clearmix (product name: CLM-2.2S, manufactured by M. Technique Co., Ltd.) which is a high-speed rotation type dispersing emulsifier.
<Step 1: Mixing and Separation>

Next, the prepared separating solvent of the organic material microparticle and the prepared raw material solution of the organic material microparticle were mixed by using the microreactor ULREA shown in FIG. 2 (A). Specifically, from the first introduction part d1 of the microreactor ULREA shown in FIG. 2 (A), the prepared separating solvent of the organic material microparticle (here, the 0.1 mol/L aqueous hydrochloric acid solution) was introduced as the first fluid to be processed (A solution) into between the processing surfaces with the supply rate of 200 mL/min and the temperature of 5° C. With operating the processing member 10 with the rotation number of 1700 rpm, the prepared raw material indomethacin solution was introduced as the second fluid to be processed (B solution) into between the processing surfaces 1 and 2 with the supply rate of 30 mL/min and the temperature of 25° C. so as to mix them in a thin film fluid. Then, the solution containing the indomethacin microparticles was discharged from the processing surfaces 1 and 2.
<Step c: Recovery and Washing>

Figure 4:
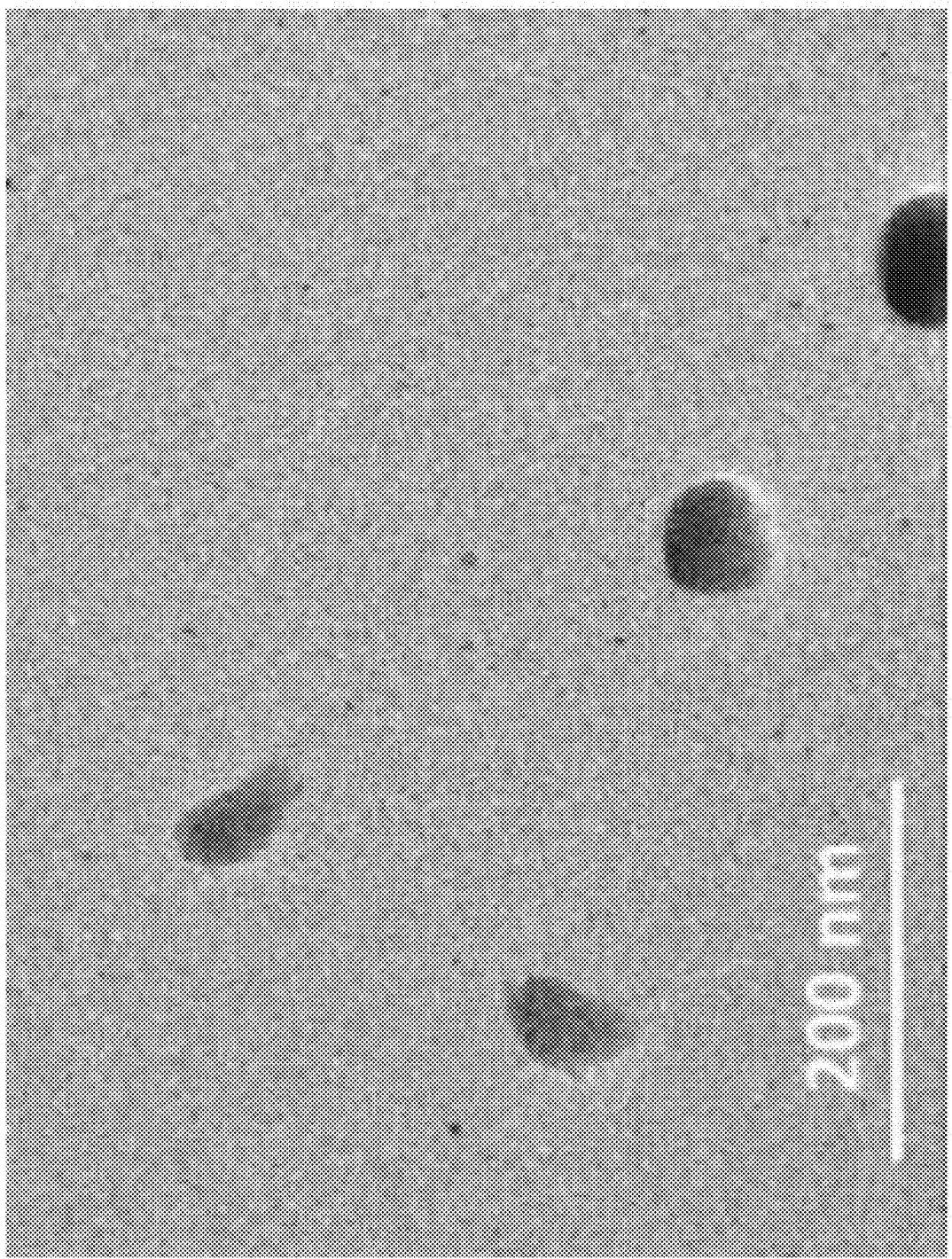
FIG. 4 This is the TEM picture of the indomethacin microparticles obtained in the step c in Example A1 of the present invention.

The above-mentioned discharged solution was filtrated to recover the indomethacin microparticles. Then, the indomethacin microparticles were washed repeatedly with the washing solvent (pure water) to obtain a wet cake of the indomethacin microparticles. The wet cake was diluted with pure water, and this diluted solution was dropped onto a collodion film and dried at room temperature to obtain the sample for observation, with which the TEM observation was conducted. The TEM observation result is shown in FIG. 4. Separately, the wet cake was vacuum-dried at −0.095 MPaG for 16 hours to obtain the dried powder. The X-ray diffraction measurement result of the obtained dry powder is shown in the upper column of FIG. 5.

From the TEM observation result, it was confirmed that the average primary particle diameter of the indomethacin microparticles was about 76 nm. From the X-ray diffraction measurement result, it was confirmed that the obtained particles were of amorphous.

<Step 2: Control of the Particle Properties>

In the step 2 for control of the particle properties, pure water was used as the solvent which has a partial dissolvability to the organic material microparticle, and hydroxyethyl cellulose (HEC) was used as the surfactant capable of suppressing the growth of the organic material microparticle. Pure water added with hydroxyethyl cellulose was stirred by using Clearmix Dissolver (product name: CLM-2.2S, manufactured by M. Technique Co., Ltd.), a high-speed rotation type dispersing emulsifier, with the rotor's rotation number of 15000 rpm for the period of 30 minutes to obtain a uniformly mixed hydroxyethyl cellulose aqueous solution (particle property control solution). The wet cake of the indomethacin microparticles obtained in the step c was introduced into this particle property control solution, and then, the dispersion treatment thereof was conducted.

Figure 6:
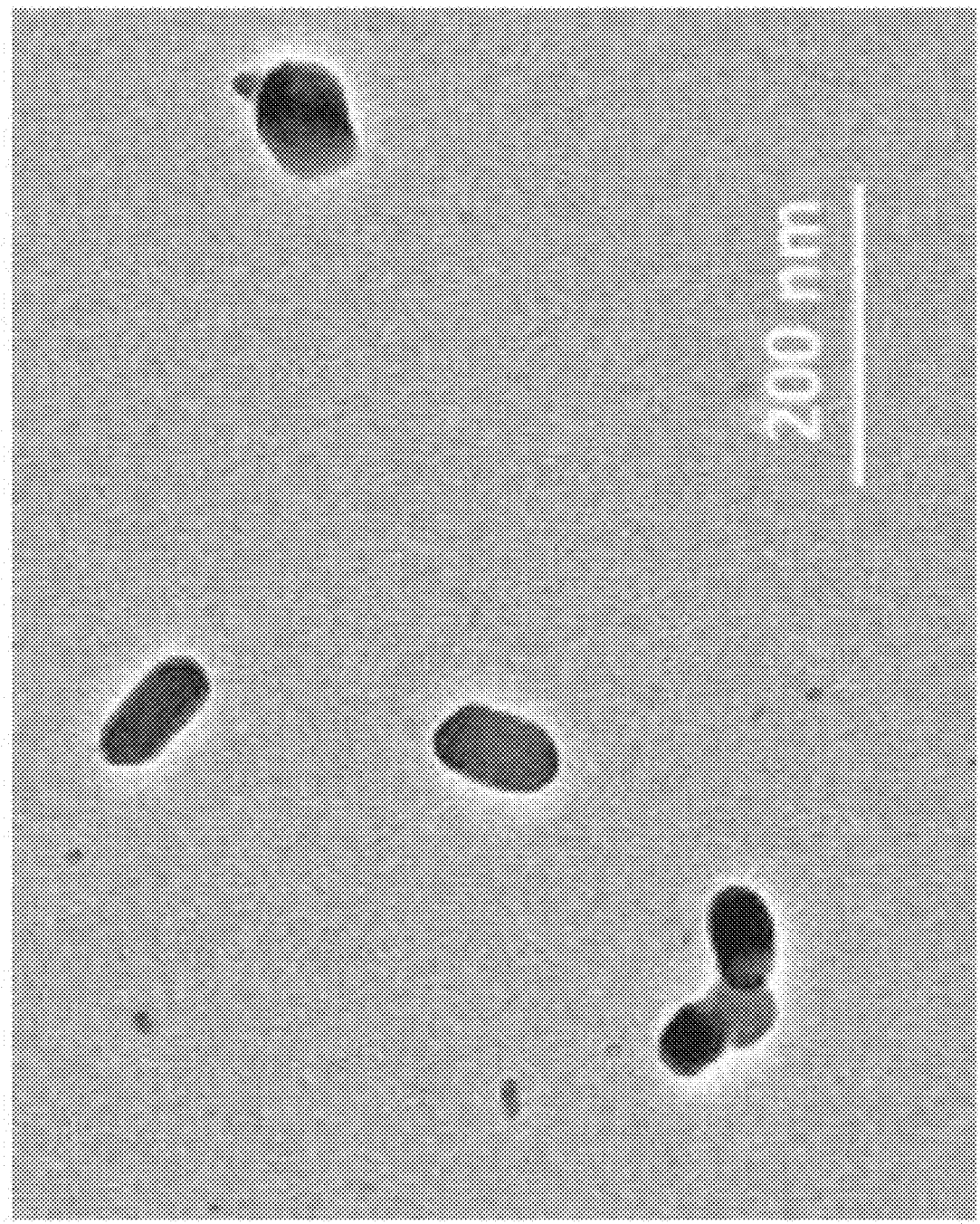
FIG. 6. This is the TEM picture of the indomethacin microparticles obtained in the step 2 in Example A1 of the present invention.

Specifically, the indomethacin microparticles obtained in the step c was added into the aqueous solution containing 0.1% by weight of hydroxyethyl cellulose (viscosity: 200 to 300 mPa·s, 2% in water at 20° C., manufactured by Tokyo Chemical Industry Co., Ltd. (TCI)) so as to give its concentration of 0.2% by weight. Then, the resulting mixture was subjected to the dispersion treatment by using the ultrasonic disperser (UP 200S; manufactured by Heilscher Ultrasonics GmbH) with 0.5% output and 0.5 cycle for the period of 15 minutes and with the treatment temperature of 37±3° C. to obtain the dispersion solution of the indomethacin microparticles. For the TEM observation, the obtained dispersion solution of the indomethacin microparticles was dropped onto a collodion film, and then, it was dried at room temperature to obtain the sample for the observation. The TEM observation result thereof is shown in FIG. 6.

From the TEM observation result, it was confirmed that the average primary particle diameter of the indomethacin microparticles after having been acted by the aqueous solution containing 0.1% by weight of hydroxyethyl cellulose was about 98 nm. Further, the indomethacin microparticles were recovered from the dispersion solution by filtration; and after the microparticles were washed with pure water, they were vacuum-dried at −0.095 MPaG and the temperature of 25° C. for 16 hours to obtain the dried powder. The X-ray diffraction measurement result of the obtained dry powder is shown in the lower column of FIG. 5.

Figure 5:
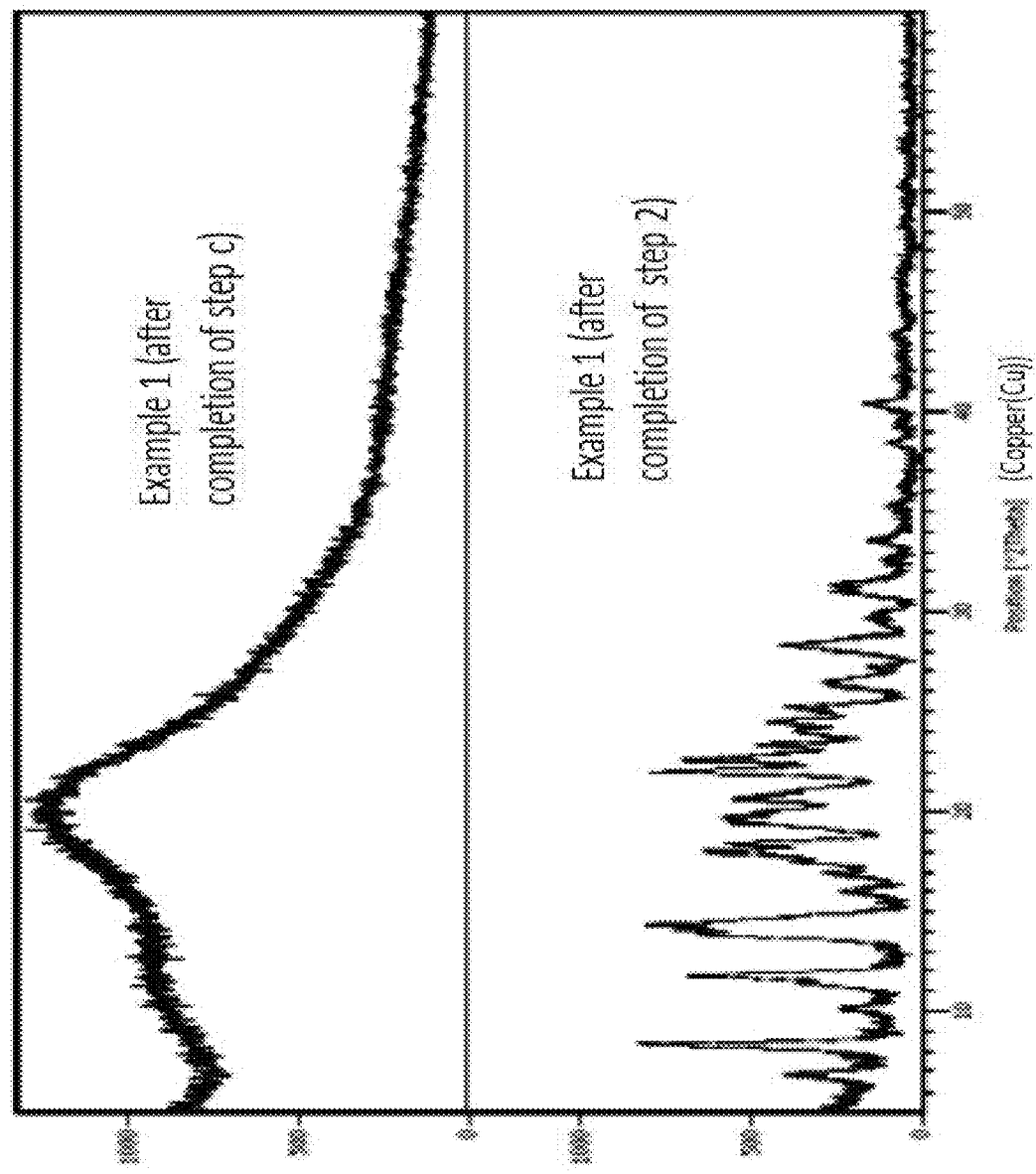
FIG. 5. These are the X-ray diffraction measurement results of the indomethacin microparticles obtained in the step c and the step 2 in Example A1 of the present invention.

From the X-ray diffraction measurement result, it was confirmed that the indomethacin microparticles after having been acted by the 0.1% by weight hydroxyethyl cellulose aqueous solution in the step 2 underwent the crystal transition to the alpha-type crystal. Meanwhile, for comparison purpose, the X-ray diffraction measurement result of the indomethacin microparticles recovered and washed in the step c (before the treatment in the step 2) is also shown in FIG. 5.

Example A2

Figure 7:
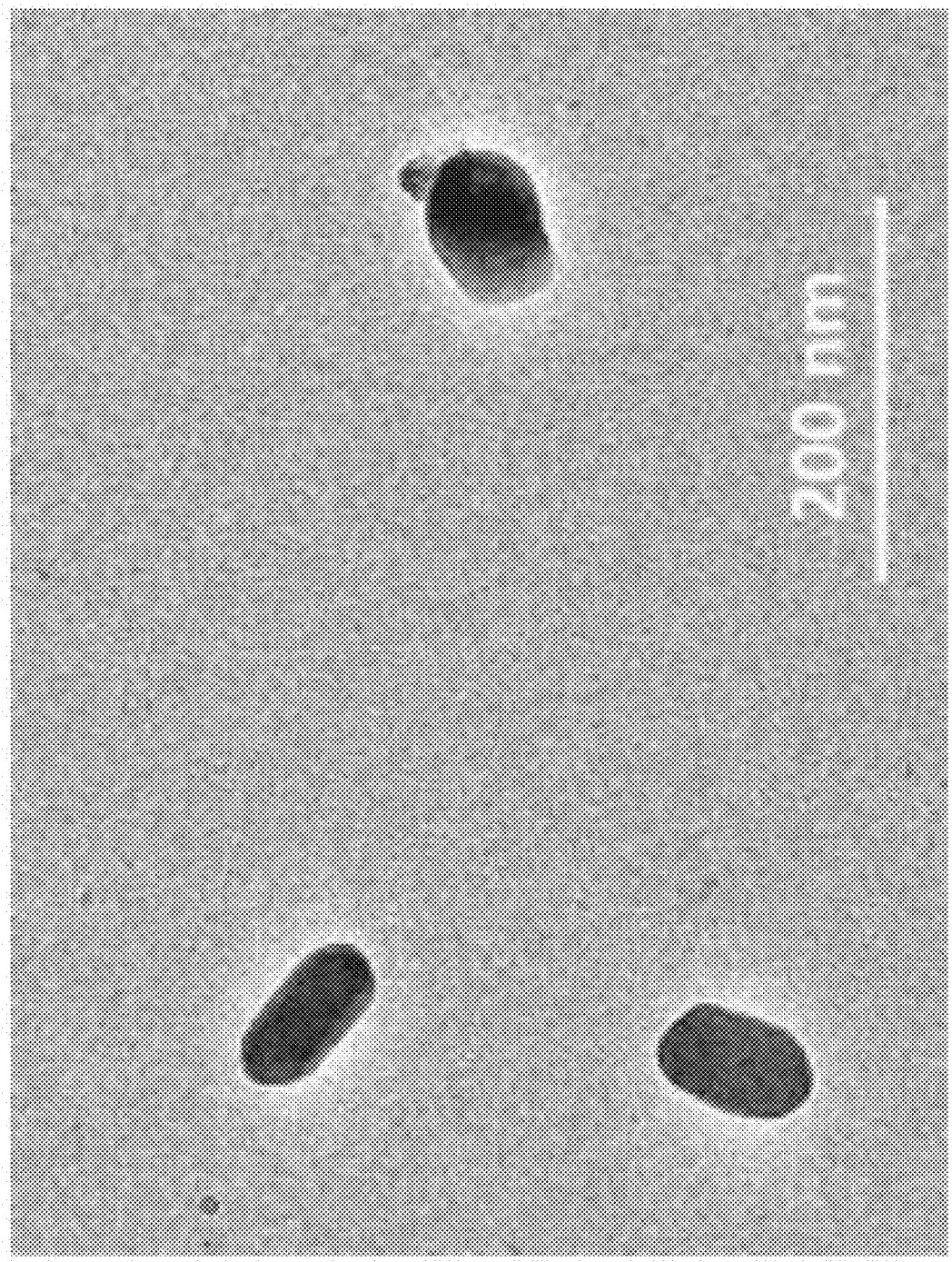
FIG. 7. This is the TEM picture of the indomethacin microparticles obtained in the step 2 in Example A2 of the present invention.

The indomethacin microparticles were produced with the same condition as that of Example A1 except that the concentration of hydroxyethyl cellulose in the step 2 of Example A1 was changed from 0.1% by weight to 0.05% by weight. The TEM picture of the indomethacin microparticles obtained in the step 2 of Example A2 is shown in FIG. 7. As can be seen in FIG. 7, it was confirmed that the average primary particle diameter of the indomethacin microparticles was about 126 nm.

Comparative Example A1

As the solvent for control of the particle properties in the step 2 of Example A1, only pure water which is the solvent having a partial dissolvability to indomethacin was used without being added with the surfactant. Then, the indomethacin microparticles were produced with the same conditions in the rest of the conditions as those of Example A1.

The TEM observation result of the indomethacin microparticles obtained in the step 2 of Comparative Example A1 is shown in FIG. 8. From the TEM observation result, it was confirmed that the particle was coarsened to about 850 nm.

Example A3: Indomethacin Microparticle

The indomethacin microparticles were produced with the same conditions from the step 0 to the step c as those of Example A1, though the solvent which has a partial dissolvability to the organic material microparticle in the step 2 was changed from pure water in Example A1 to hexane, and the surfactant capable of suppressing the growth of the organic material microparticle was changed to Span 80 from hydroxyethyl cellulose in Example A1.

Figure 9:
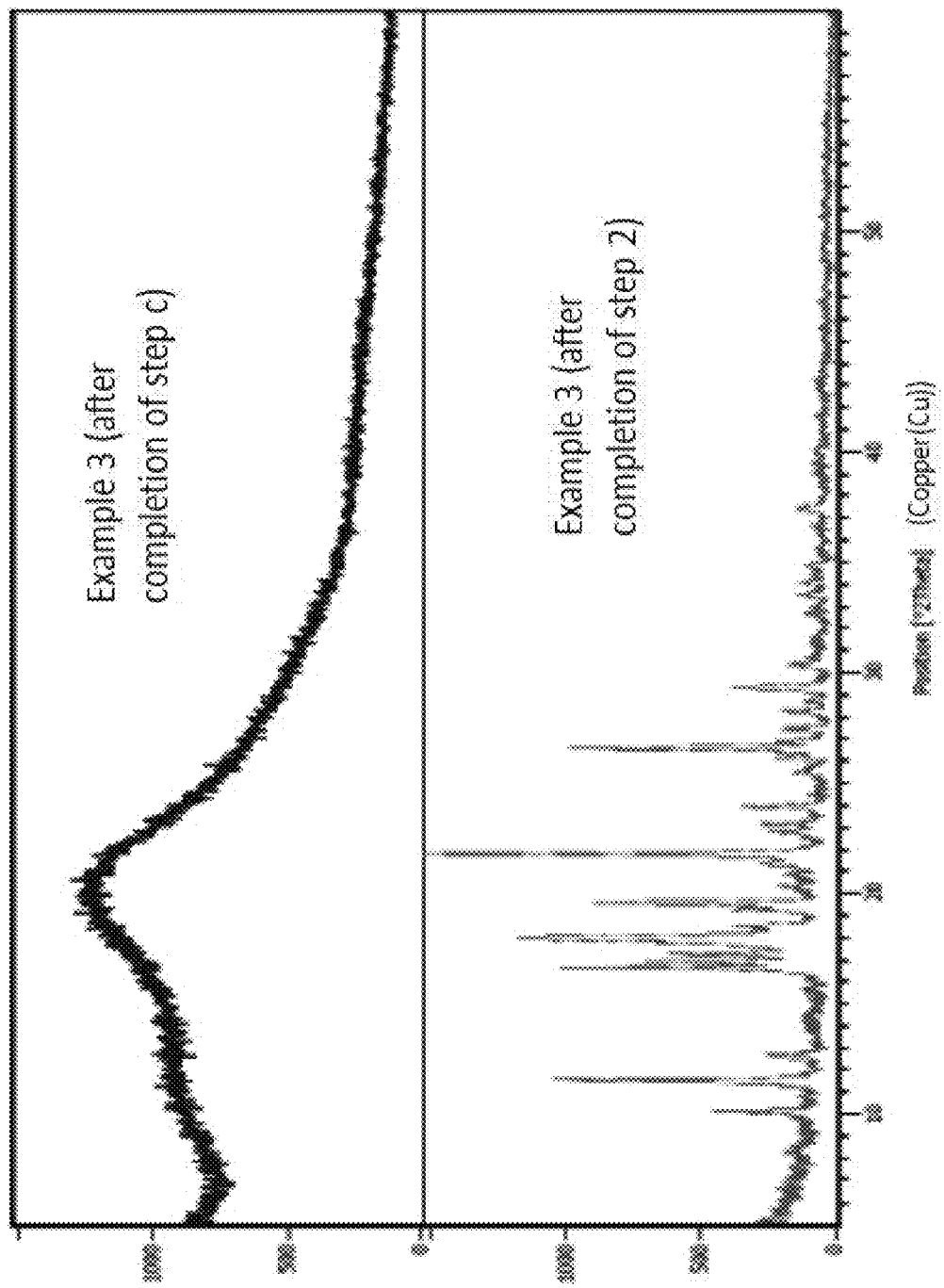
FIG. 9. These are the X-ray diffraction measurement results of the indomethacin microparticles obtained in the step c and the step 2 in Example A3 of the present invention.

Specifically, the uniformly mixed hexane solution containing 0.01% by weight of Span 80 (manufactured by Wako Pure Chemical Industries, Ltd.) (particle property control solution) was prepared by stirring this solution with Clearmix Dissolver (product name: CLM-2.2S, manufactured by M. Technique Co., Ltd.), a high-speed rotation type dispersing emulsifier, with the rotor's rotation number of 15000 rpm for the period of 30 minutes. After the indomethacin microparticles obtained in the step c was added to the particle property control solution so as to give its concentration of 0.2% by weight, the resulting mixture was subjected to the dispersion treatment by stirring by means of a magnetic stirrer at 150 rpm and the temperature of 27° C. for 16 hours to obtain the dispersion solution of the indomethacin microparticles. From the dispersion solution thereby obtained, the indomethacin microparticles were recovered by filtration, and then vacuum-dried at −0.095 MPaG and the temperature of 25° C. for 16 hours to obtain the dried powder for the X-ray diffraction measurement. The X-ray diffraction measurement result thereof is shown in the lower column of FIG. 9. Meanwhile, in the upper column of FIG. 9, the X-ray diffraction measurement result of the indomethacin microparticles obtained in the step c of Example A3 is shown.

From the X-ray diffraction measurement result, it was confirmed that the indomethacin microparticles after having been acted by the hexane solution containing 0.01% by weight of Span 80 was transformed to the gamma-type crystal.

Figure 10:
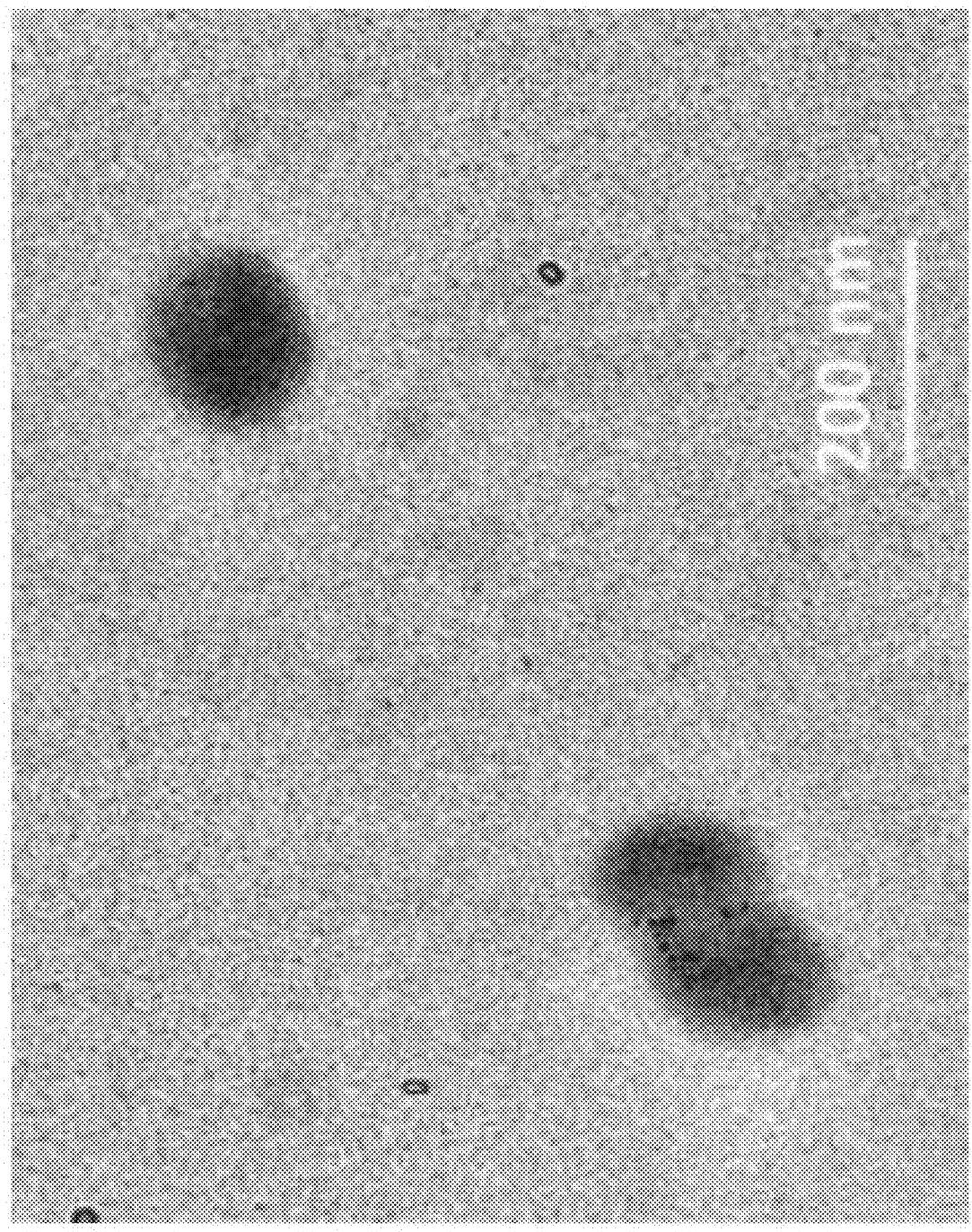
FIG. 10. This is the TEM picture of the indomethacin microparticles obtained in the step 2 in Example A3 of the present invention.

Thereafter, the dried powder was dispersed into the aqueous solution containing 0.1% by weight of hydroxyethyl cellulose (viscosity: 200 to 300 mPa·s, 2% in water at 20° C., manufactured by Tokyo Chemical Industry Co., Ltd. (TCI)) to obtain the sample for the TEM observation. The TEM observation result thereof is shown in FIG. 10.

From the TEM observation result, it was confirmed that the average primary particle diameter of the indomethacin microparticles after having been acted by the hexane solution containing 0.01% by weight of Span 80 (particle property control solution) in the step 2 of Example A3 was about 138 nm.

Comparative Example A2: Indomethacin Microparticle

As the solvent for control of the particle properties in the step 2 of Example A3, only hexane which is the solvent having a partial dissolvability to indomethacin was used without being added with the surfactant. Then, the indomethacin microparticles were produced with the same conditions in the rest of the conditions as those of Example A3.

The TEM observation result of the indomethacin microparticles obtained in the step 2 of Comparative Example A2 is shown in FIG. 11. From the TEM observation result, it was confirmed that the particles were coarsened to about 1000 nm.

Example A4: Indomethacin Microparticle

In Example A4, the separating solvent of indomethacin and the raw material indomethacin solution in the step 0 of Examples A1 to A3 were changed; then the alpha-type indomethacin microparticle was separated in the step 1. In addition, the surfactant capable of suppressing the growth of the organic material microparticle in the step 2 of Example A1 was changed.

In the step 0, pure water was used as the separating solvent of the organic microparticle (A solution). This solvent was not prepared because only pure water was used for it. Into ethanol were added indomethacin having the gamma-type crystal and polyvinyl pyrrolidone (Kollidon 12 PF; manufactured by BASF GmbH) so as to give the concentration of 1.0% by weight and 1.0% by weight, respectively, thereby the raw material indomethacin solution was prepared as the raw material solution of the organic material microparticle (B solution). Similarly to Examples A1 to A3, the resulting mixture was stirred by using Clearmix (product name: CLM-2.2S, manufactured by M. Technique Co., Ltd.), a high-speed rotation type dispersing emulsifier, with the rotor's rotation number of 15000 rpm and the temperature of about 35° C. for the period of 30 minutes so as to prepare the uniform raw material indomethacin solution.

Figure 12:
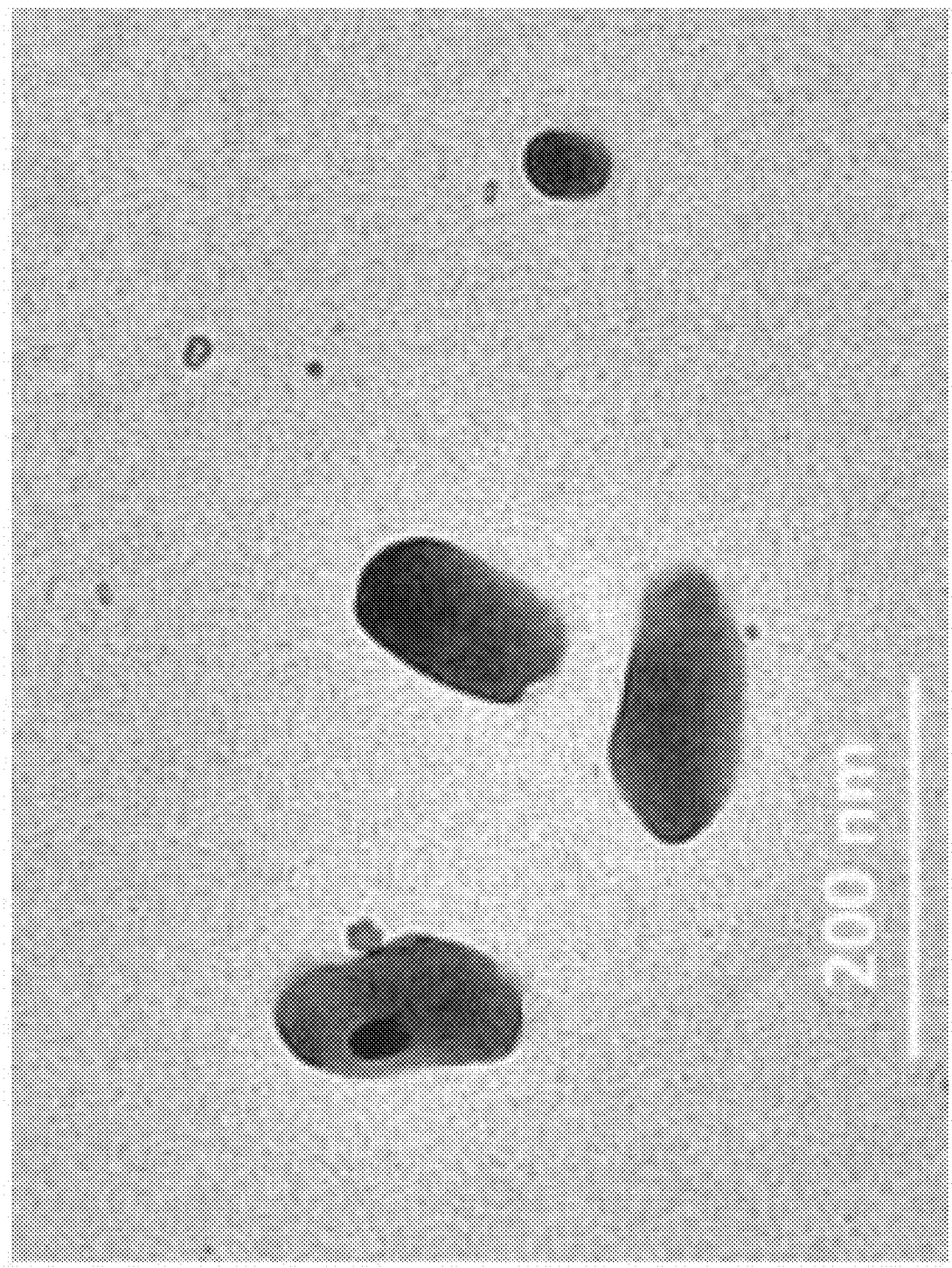
FIG. 12. This is the TEM picture of the indomethacin microparticles obtained in the step c in Example A4 of the present invention.
Figure 13:
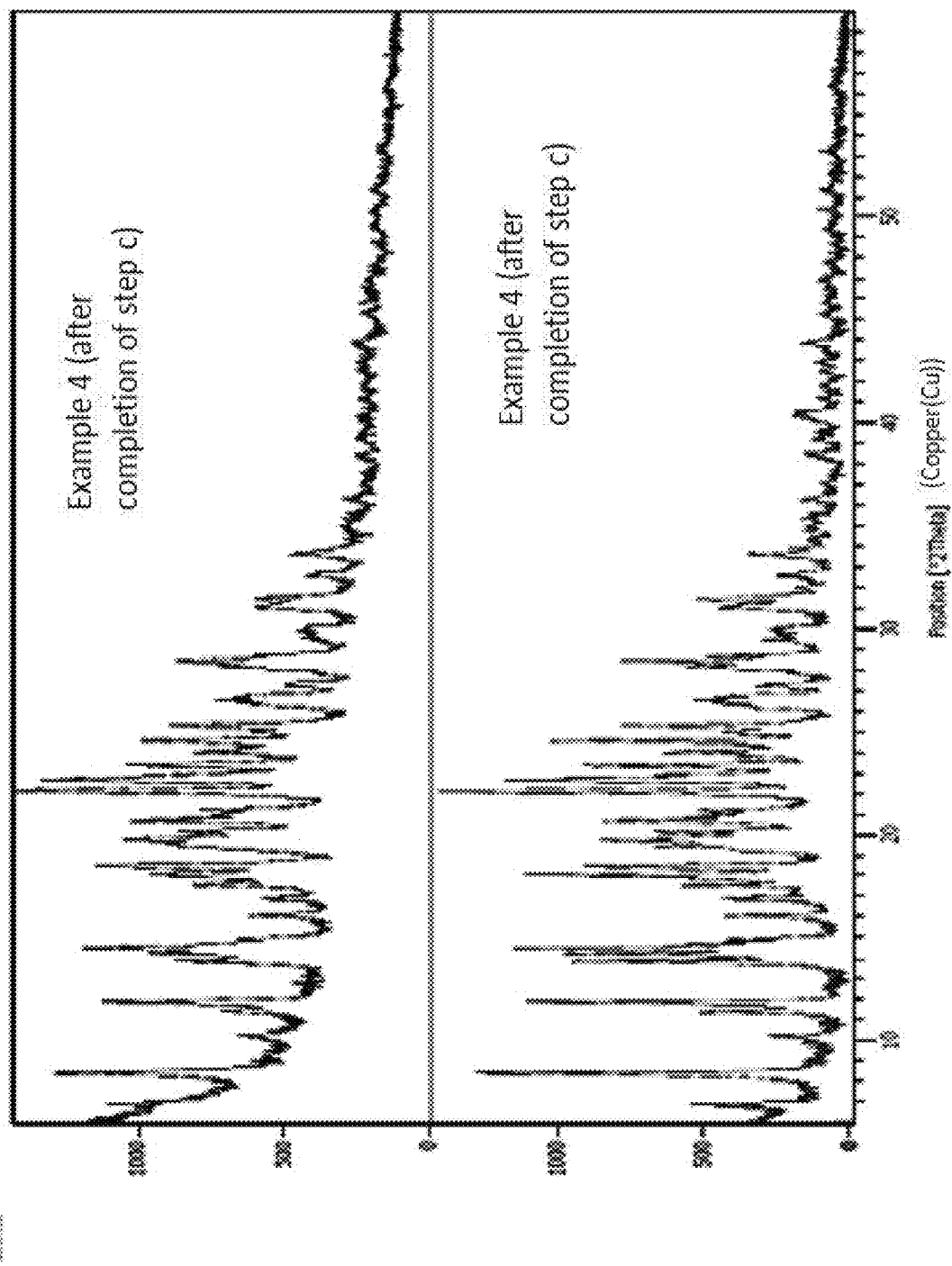
FIG. 13. These are the X-ray diffraction measurement results of the indomethacin microparticles obtained in the step c and the step 2 in Example A4 of the present invention.

Procedures of the step 1 (mixing and separation) and the step c (recovery and washing) were the same as Examples A1 to A3. Similarly to Examples A1 to A3, the indomethacin microparticles were separated in the step 1; and by using the wet cake obtained in the step c, the sample for the TEM observation and the dried powder for the X-ray diffraction measurement were obtained. The TEM observation result is shown in FIG. 12, and the X-ray diffraction measurement result is shown in the upper column of FIG. 13.

From the TEM observation result, it was confirmed that the average primary particle diameter of the indomethacin microparticles after having been subjected to the washing treatment was about 146 nm. From the X-ray diffraction measurement result, it was confirmed that the crystal type of the indomethacin microparticles was the alpha-type. Meanwhile, the degree of crystallinity thereof was 50%.
<Step 2: Control of the Particle Properties>

In the step 2 for control of the particle properties, pure water was used as the solvent which has a partial dissolvability to the organic material microparticle, and Lutrol F127 (manufactured by BASF GmbH) was used as the surfactant capable of suppressing the growth of the organic material microparticle. Pure water added with Lutrol F127 was stirred by using Clearmix Dissolver (product name: CLM-2.2S, manufactured by M. Technique Co., Ltd.), a high-speed rotation type dispersing emulsifier, with the rotor's rotation number of 15000 rpm for the period of 30 minutes to obtain a uniformly mixed Lutrol F127 aqueous solution (particle property control solution). The wet cake of the indomethacin microparticles obtained in the step c was introduced into this particle property control solution, and then, the dispersion treatment thereof was conducted.

Figure 14:
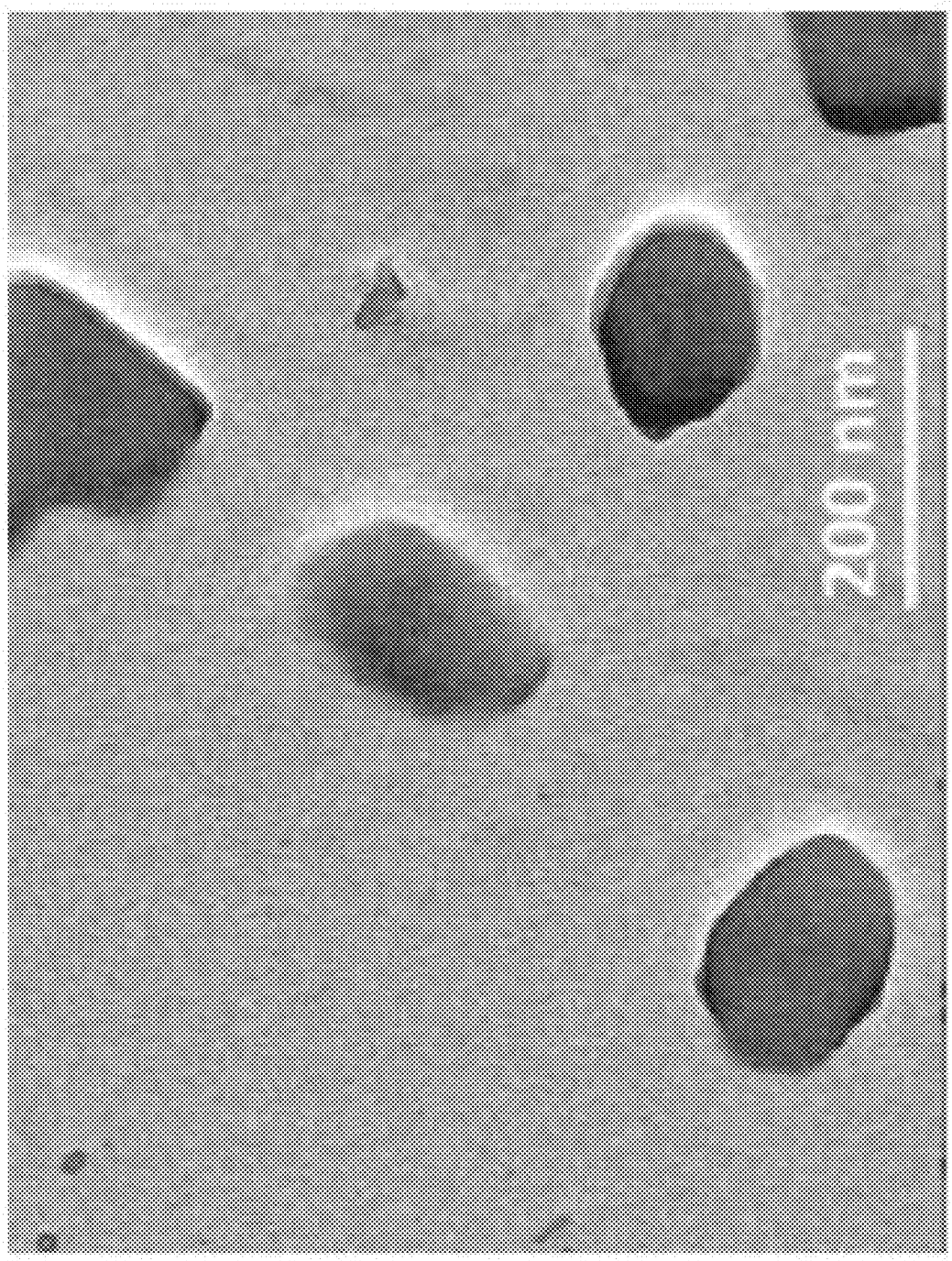
FIG. 14. This is the TEM picture of the indomethacin microparticles obtained in the step 2 in Example A4 of the present invention.

Specifically, the indomethacin microparticles obtained in the step c was added into the aqueous solution containing 0.1% by weight of Lutrol F127 so as to give its concentration of 0.2% by weight. Then, the resulting mixture was subjected to the dispersion treatment by using the ultrasonic disperser (UP 200S; manufactured by Heilscher Ultrasonics GmbH) with 0.5% output and 0.5 cycle for the period of 15 minutes and with the treatment temperature of 37±3° C. to obtain the indomethacin dispersion solution. The obtained indomethacin dispersion solution was dropped onto a collodion film, and then, it was dried at room temperature to obtain the sample for the TEM observation. The TEM observation result thereof is shown in FIG. 14.

From the TEM observation result, it was confirmed that the average primary particle diameter of the indomethacin microparticles after having been acted by the aqueous solution containing 0.1% by weight of Lutrol F127 was about 168 nm. Further, the indomethacin microparticles were recovered from the dispersion solution by filtration; and after the microparticles were washed with pure water, they were vacuum-dried at −0.095 MPaG and with the temperature of 25° C. for 16 hours to obtain the dried powder for the X-ray diffraction measurement. The X-ray diffraction measurement result thereof is shown in the lower column of FIG. 13.

From the X-ray diffraction measurement result, it was confirmed that the indomethacin microparticle after having been acted by the aqueous solution containing 0.1% by weight of Lutrol F127 was of the alpha-type crystal, the same as the indomethacin microparticle obtained in the step c. The degree of crystallinity thereof was 62.5%; and thus, it was confirmed that the degree of crystallinity was increased as compared with the indomethacin microparticle obtained in the step c. This is presumably because the amorphous portion contained in the indomethacin microparticles obtained in the step 1 and step 2 was crystallized.

Comparative Example A3: Indomethacin Microparticle

As the solvent for control of the particle properties in the step 2 of Example A4, only pure water which is the solvent having a partial dissolvability to indomethacin was used without being added with the surfactant. Then, the indomethacin microparticles were produced with the same conditions in the rest of the conditions as those of Example A4.

Figure 15:
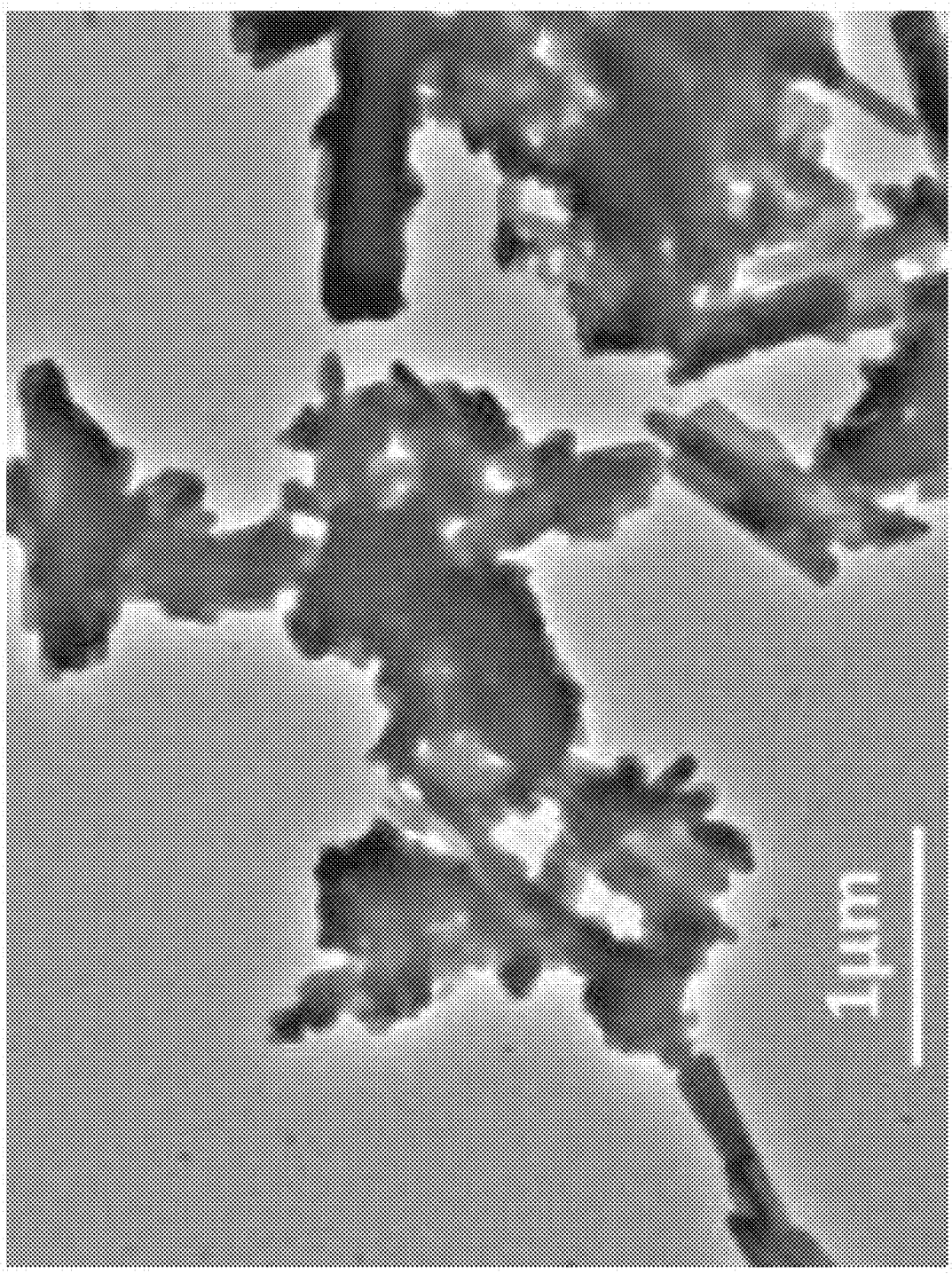
FIG. 15. This is the TEM picture of the indomethacin microparticles obtained in the step 2 in Comparative Example A3 of the present invention.

The TEM observation result thereof is shown in FIG. 15. From the TEM observation result, it was confirmed that the particles were coarsened to about 1160 nm.

Example A5: Curcumin Microparticle

<Step 0: Preparation of the Separating Solvent of the Organic Material Microparticle (A Solution) and the raw Material Solution of the Organic Material Microparticle (B Solution)>

In the step 0, pure water was used as the separating solvent of the organic microparticle (A solution). This solvent was not prepared because only pure water was used for it. Into ethanol were added curcumin having the 1-type crystal and polyvinyl pyrrolidone (Kollidon 12 PF; manufactured by BASF GmbH) so as to give the concentrations of 0.5% by weight and 0.5% by weight, respectively, thereby the raw material curcumin solution was prepared as the raw material solution of the organic material microparticle (B solution). Similarly to Examples A1 to A4, the resulting mixture was stirred by using Clearmix (product name: CLM-2.2S, manufactured by M. Technique Co., Ltd.), a high-speed rotation type dispersing emulsifier, with the rotor's rotation number of 15000 rpm and the temperature of about 35° C. for the period of 30 minutes so as to prepare the uniform raw material curcumin solution.

<Step 1: Mixing and Separation>

Next, the separating solvent of the organic material microparticle and the prepared raw material solution of the organic material microparticle were mixed by using the microreactor shown in FIG. 2 (A). Specifically, from the first introduction part d1 of the microreactor shown in FIG. 2 (A), the separating solvent of the organic material microparticle (here, pure water) was introduced as the first fluid to be processed (A solution) into between the processing surfaces with the supply rate of 500 mL/min and the temperature of 5° C.; and with operating the processing member 10 at the rotation number of 1700 rpm, the prepared raw material solution of the organic material microparticle was introduced as the second fluid to be processed (B solution) into between the processing surfaces 1 and 2 with the supply rate of 30 mL/min and the temperature of 25° C. so as to mix them in a thin film fluid. Then, the solution containing the curcumin microparticles was discharged from the processing surfaces 1 and 2.

<Step c: Recovery and Washing>

The above-mentioned discharged solution was filtrated to remove the supernatant liquid so as to recover the curcumin microparticles. Then, the curcumin microparticles were repeatedly washed for three times with the washing solvent (pure water) to obtain a wet cake of the curcumin microparticles. This wet cake was diluted with pure water, and the resulting diluted solution was dropped onto a collodion film and dried at room temperature to obtain the sample for observation, with which the TEM observation was conducted.

Figure 16:
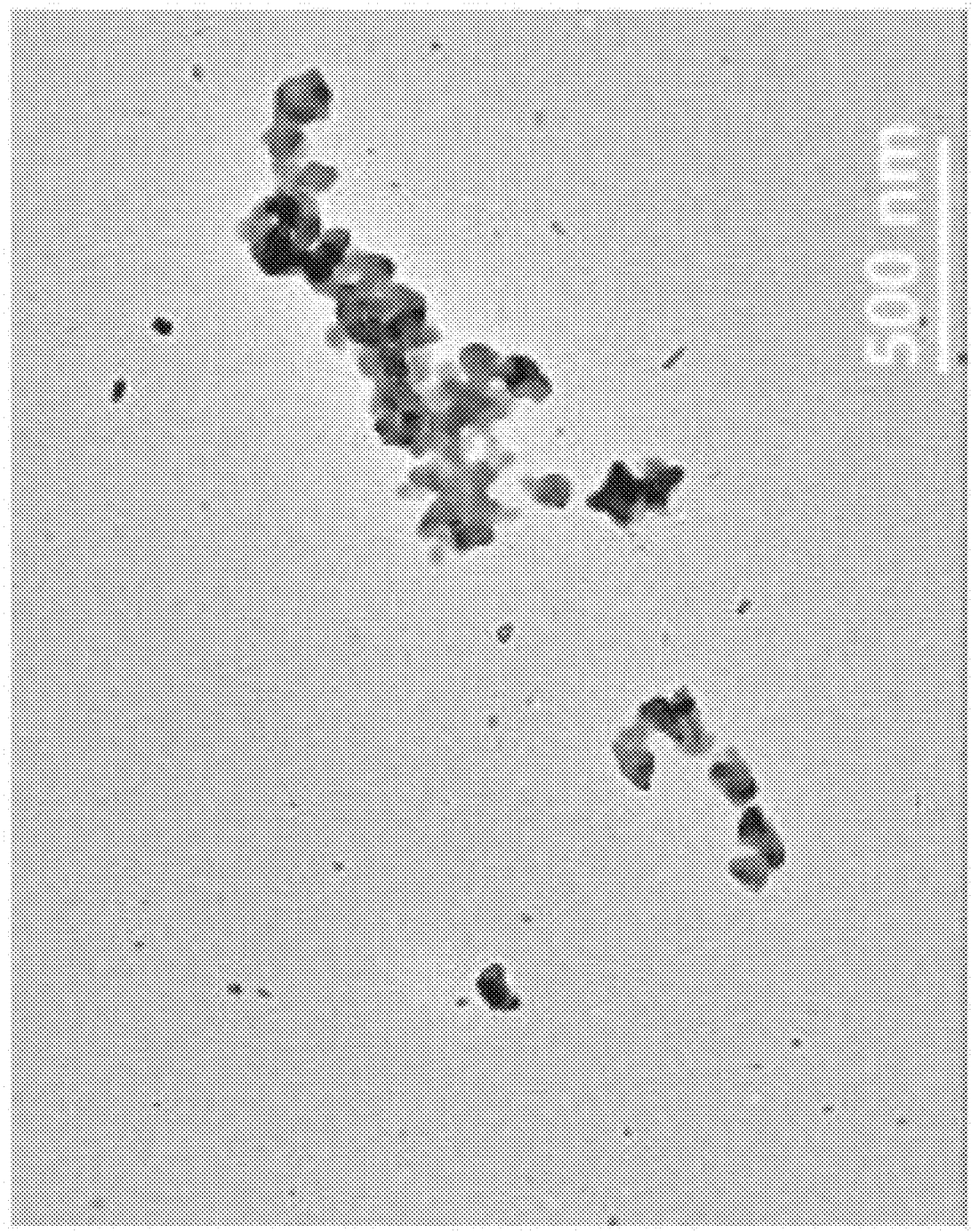
FIG. 16. This is the TEM picture of the curcumin microparticles obtained in the step c in Example A5 of the present invention.
Figure 17:
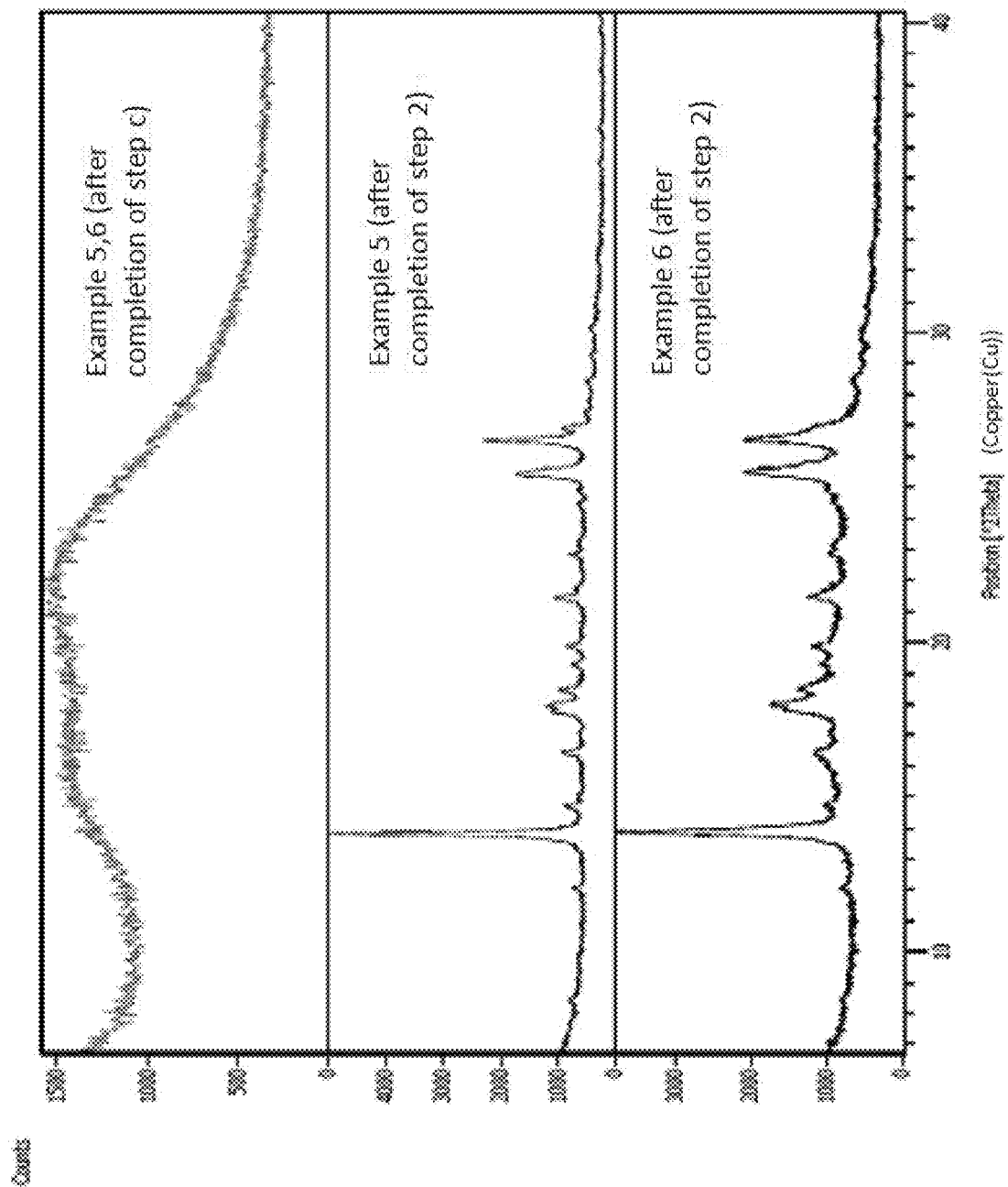
FIG. 17. These are the X-ray diffraction measurement results of the curcumin microparticles obtained in the step c and the step 2 in Example A5 and Example A6 of the present invention.

Separately, the foregoing wet cake was vacuum-dried at −0.095 MPaG for 16 hours to obtain the dried powder for the X-ray measurement. The TEM observation result is shown in FIG. 16, and the X-ray diffraction measurement result is shown in the upper column of FIG. 17.

From the TEM observation result, it was confirmed that the average primary particle diameter of the curcumin microparticles was about 88 nm. From the X-ray diffraction measurement result, it was confirmed that the obtained particles were of amorphous.

<Step 2: Control of the Particle Properties>

In the step 2 for control of the particle properties, pure water was used as the solvent which has a partial dissolvability to the organic material microparticle, and polyvinyl alcohol was used as the surfactant capable of suppressing the growth of the organic material microparticle. Pure water added with polyvinyl alcohol (PVA) was stirred by using Clearmix Dissolver (product name: CLM-2.2SD, manufactured by M. Technique Co., Ltd.), a high-speed rotation type dispersing emulsifier, with the rotor's rotation number of 15000 rpm for the period of 30 minutes to obtain a uniformly mixed polyvinyl alcohol aqueous solution (particle property control solution). The wet cake of the curcumin microparticles obtained in the step c was introduced into this particle property control solution, and then, the dispersion treatment thereof was conducted.

Figure 18:
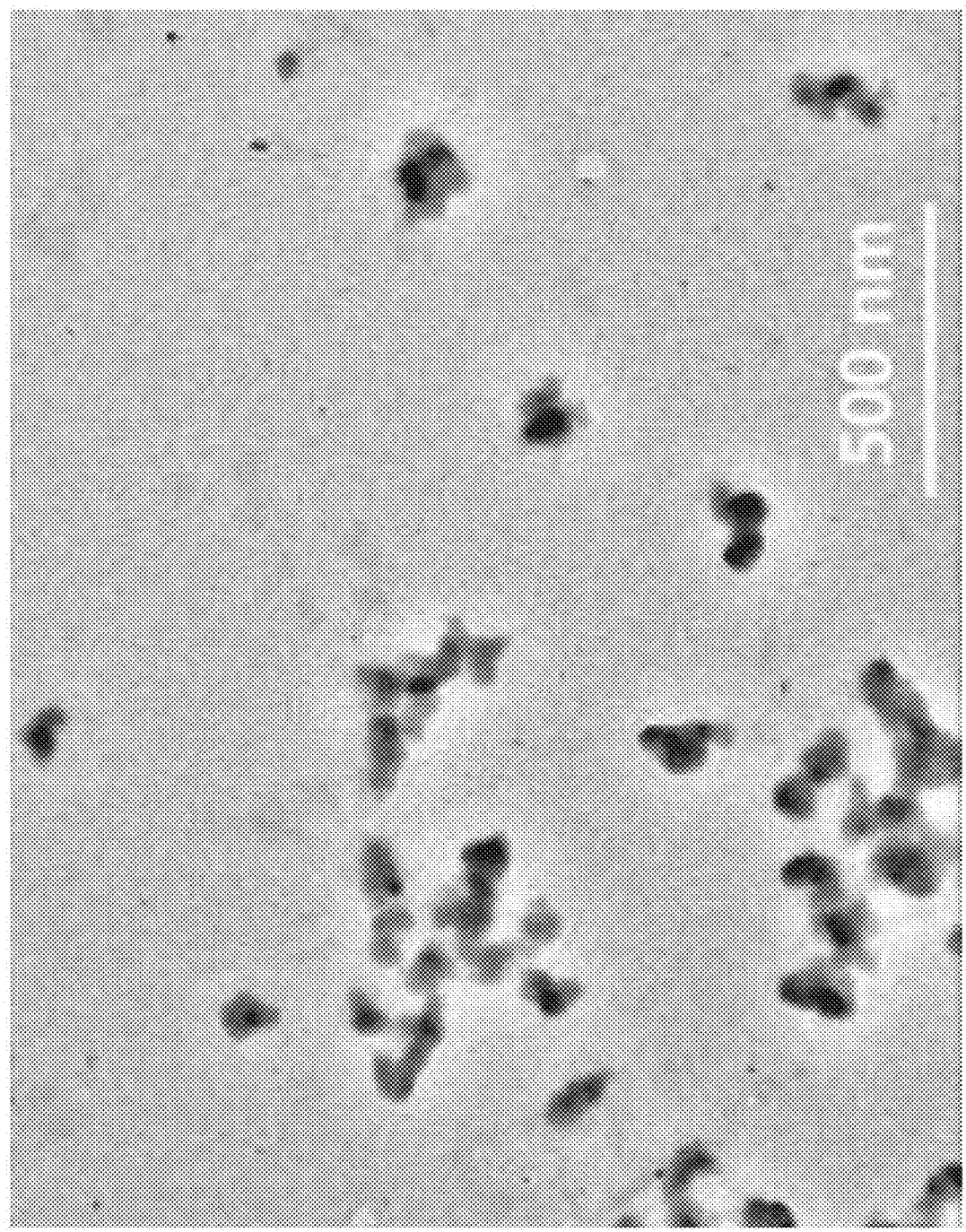
FIG. 18. This is the TEM picture of the curcumin microparticles obtained in the step 2 in Example A5 of the present invention.

Specifically, the curcumin microparticles obtained in the step c was added into the aqueous solution containing 0.2% by weight of polyvinyl alcohol 500 (completely saponified type) so as to give its concentration of 0.2% by weight. Then, the resulting mixture was subjected to the dispersion treatment by using the ultrasonic disperser (UP 200S; manufactured by Heilscher Ultrasonics GmbH) with 0.5% output and 0.5 cycle and with the treatment temperature of 30±3° C. for the period of 30 minutes to obtain the dispersion solution of the curcumin microparticles. The obtained dispersion solution was dropped onto a collodion film, and then, it was dried at room temperature to obtain the sample for the TEM observation. The TEM observation result thereof is shown in FIG. 18.

From the TEM observation result, it was confirmed that the average primary particle diameter of the curcumin microparticles after having been acted by the aqueous solution containing 0.2% by weight of polyvinyl alcohol 500 (completely saponified type) was about 108 nm. Further, the curcumin microparticles were recovered from the dispersion solution by filtration; and after the microparticles were washed with pure water, they were vacuum-dried at −0.095 MPaG with the temperature of 25° C. for 12 hours to obtain the dried powder for the X-ray diffraction measurement. The X-ray diffraction measurement result thereof is shown in the middle column of FIG. 17.

From the X-ray diffraction measurement result, it was confirmed that the curcumin microparticle after having been acted by the aqueous solution containing 0.2% by weight of polyvinyl alcohol 500 (completely saponified type) was transformed from amorphous to the 3-type crystal.

Comparative Example A4

As the solvent for control of the particle properties in the step 2 of Example A5, only pure water which is the solvent having a partial dissolvability to curcumin was used without being added with the surfactant. Then, the curcumin microparticles were produced with the same conditions in the rest of the conditions as those of Example A5.

Figure 19:
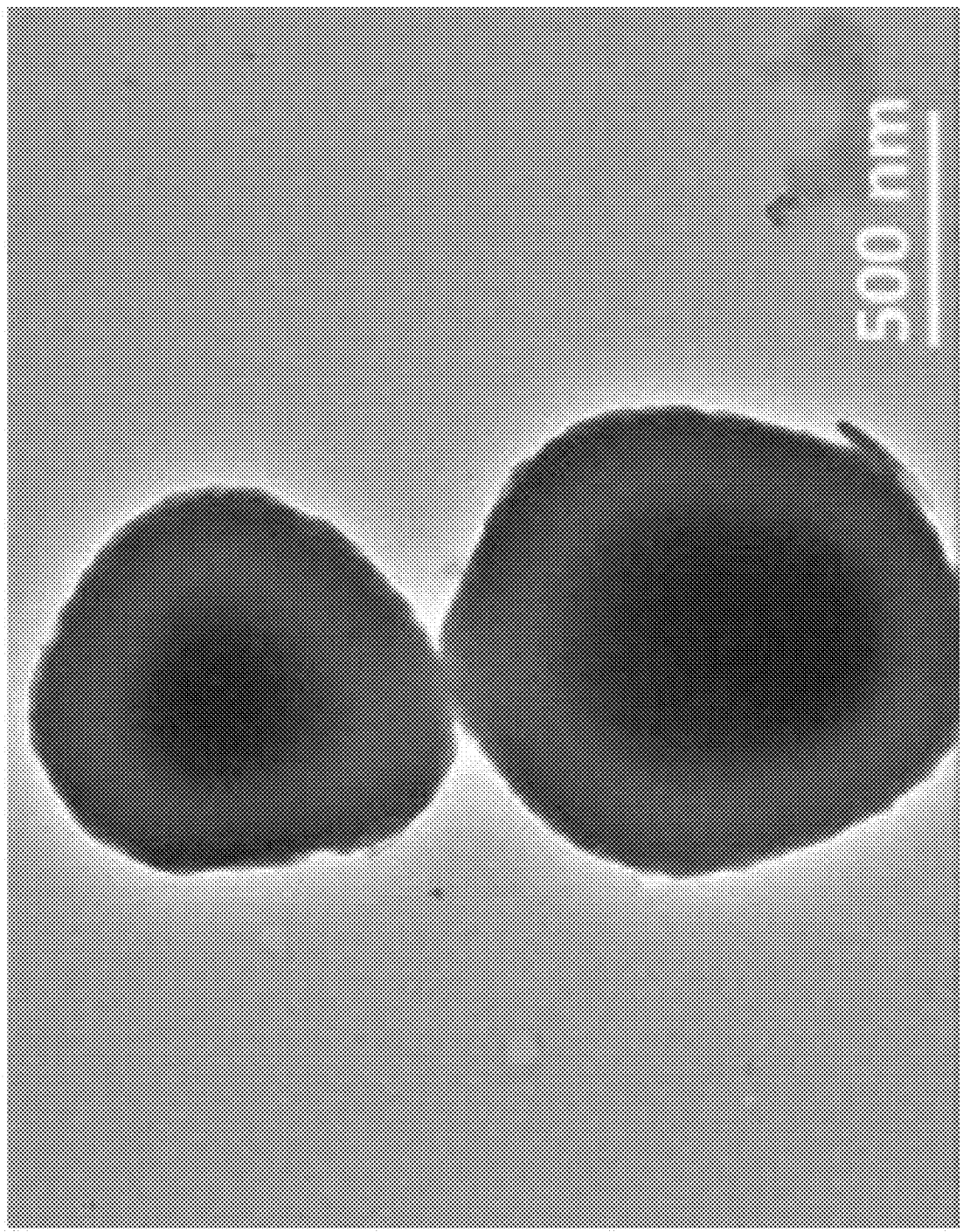
FIG. 19. This is the TEM picture of the curcumin microparticles obtained in the step 2 in Comparative Example A4 of the present invention.

The TEM observation result thereof is shown in FIG. 19. From the TEM observation result, it was confirmed that, although the crystal was transformed to the 3-type crystal, the average particle diameter of the curcumin microparticles was about 980 nm, thereby showing that the particles thereof were coarsened.

Example A6

The curcumin microparticles were produced with the same conditions from the step 0 to the step c as those of Example A5, though the solvent which has a partial dissolvability to the organic material microparticle in the step 2 was changed from pure water in Example A5 to hexane.

Span 80 (manufactured by Wako Pure Chemical Industries, Ltd.) was used as the surfactant capable of suppressing the growth of the organic material microparticle. Hexane added with Span 80 was stirred by using Clearmix Dissolver (product name: CLM-2.2SD, manufactured by M. Technique Co., Ltd.), a high-speed rotation type dispersing emulsifier, with the rotor's rotation number of 15000 rpm for the period of 30 minutes to obtain a uniformly mixed solution (particle property control solution). The dried powder of the curcumin microparticles obtained in the step c was introduced into this particle property control solution, and then, the dispersion treatment thereof was conducted.

Specifically, the curcumin microparticles obtained in the step c were added into the hexane solution containing 0.01% by weight of Span 80 so as to give its concentration of 0.2% by weight. Then, the resulting mixture was subjected to the dispersion treatment with the same condition as that of Example A5 to obtain the curcumin microparticles. From the obtained dispersion solution, the curcumin microparticles were recovered by filtration, which was followed by vacuum-drying at −0.095 MPaG with the temperature of 25° C. for 16 hours to obtain the dried powder for the X-ray diffraction measurement. The X-ray diffraction measurement result thereof is shown in the lower column of FIG. 17.

From the X-ray diffraction measurement result, it was confirmed that the curcumin microparticle after having been acted by the hexane solution containing 0.1% by weight of Span 80 was transformed from amorphous to the 2-type crystal.

Figure 20:
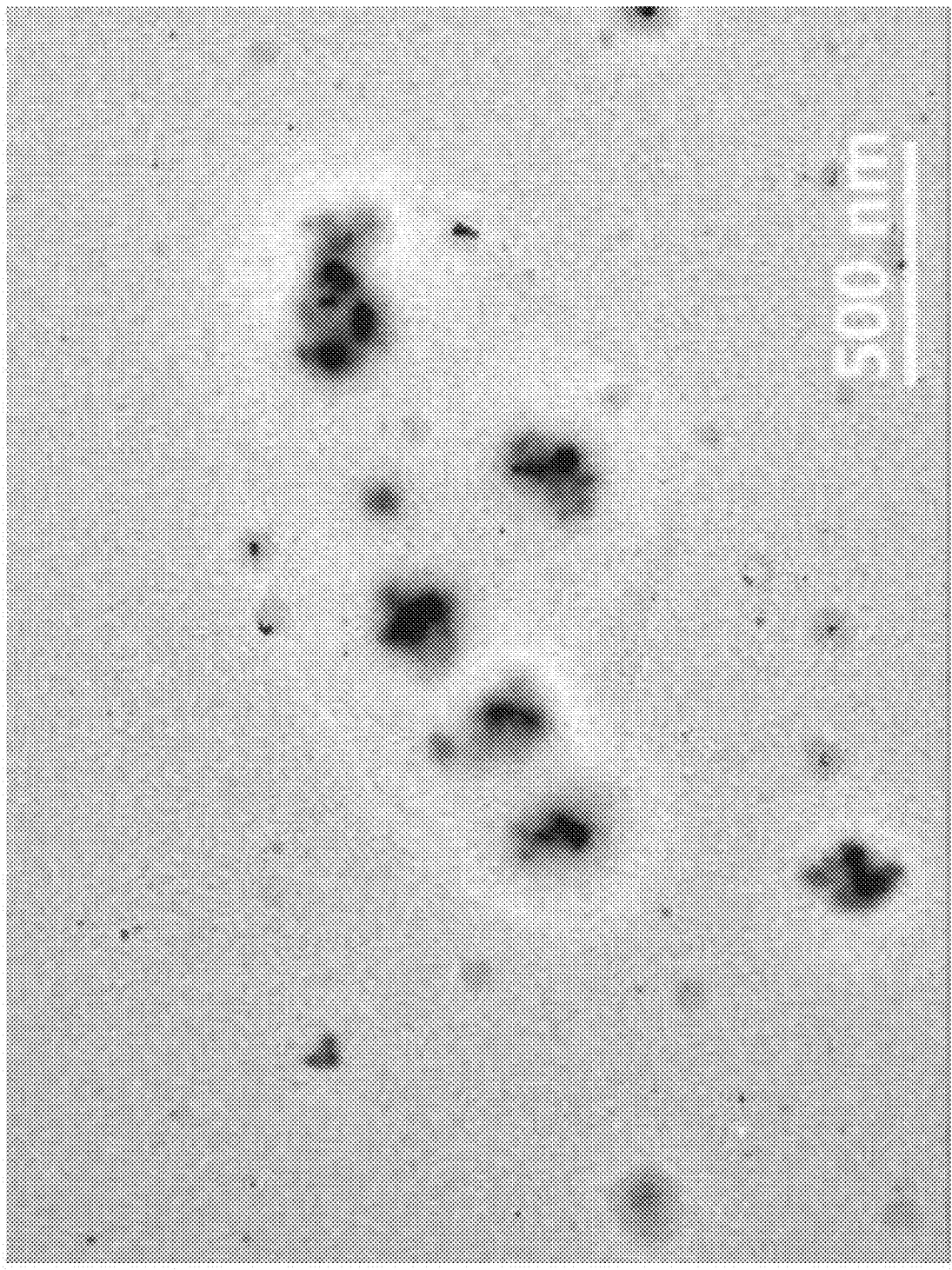
FIG. 20. This is the TEM picture of the curcumin microparticles obtained in the step 2 in Example A6 of the present invention.

Thereafter, the dried powder was dispersed into the aqueous solution containing 0.1% by weight of hydroxyethyl cellulose (viscosity: 200 to 300 mPa-s, 2% in water at 20° C., manufactured by Tokyo Chemical Industry Co., Ltd. (TCI)) to obtain the sample for the TEM observation. The TEM observation result thereof is shown in FIG. 20. From the TEM observation result, it was confirmed that the average primary particle diameter of the curcumin microparticles after having been acted by the hexane solution containing 0.1% by weight of Span 80 was about 97 nm.

Comparative Example A5

As the solvent for control of the particle properties in the step 2 of Example A6, only hexane which is the solvent having a partial dissolvability to curcumin was used without being added with the surfactant. Then, the curcumin microparticles were produced with the same conditions in the rest of the conditions as those of Example A6.

Figure 21:
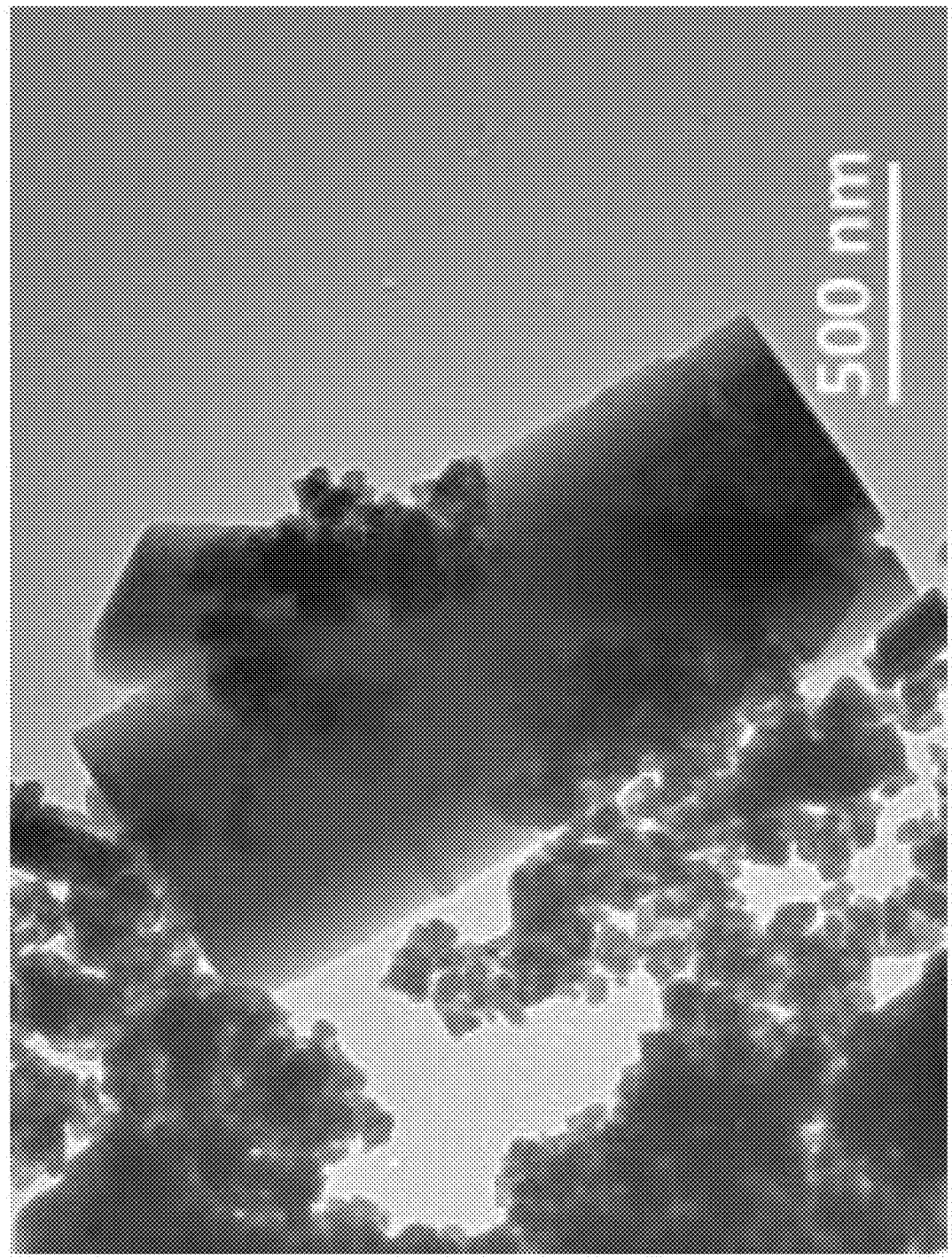
FIG. 21. This is the TEM picture of the curcumin microparticles obtained in the step 2 in Comparative Example A5 of the present invention.

The TEM observation result of the curcumin microparticles obtained in the step 2 of Comparative Example A5 is shown in FIG. 21. From the TEM observation result, it was confirmed that, although the crystal thereof was transformed to the 3-type crystal, the particles were coarsened to 1000 nm or more.

Example A7: Polypropylene Microparticle

<Step 0: Preparation of the Separating Solvent of the Organic Material Microparticle (A Solution) and the Raw Material Solution of the Organic Material Microparticle (B Solution)>

In the step 0, acetone was used as the separating solvent of the organic microparticle (A solution). This solvent was not prepared because only acetone was used for it. Polypropylene having the alpha-type crystal was added into toluene so as to give the raw material polypropylene solution with the concentration of 1% by weight as the raw material solution of the organic material microparticle (B solution). Similarly to Examples A1 to A6, the resulting mixture was stirred by using Clearmix (product name: CLM-2.2S, manufactured by M. Technique Co., Ltd.), a high-speed rotation type dispersing emulsifier, with the rotor's rotation number of 15000 rpm and the temperature of about 85° C. for the period of 30 minutes so as to prepare the uniform raw material polypropylene solution.

<Step 1: Mixing and Separation>

In Example A7, as the step 1 of a batch method in Example A, the separating solvent of the organic material microparticle and the raw material solution of the organic material microparticle were mixed by using Clearmix. Specifically, 30 mL of the prepared raw material solution of the organic material microparticle (B solution) with the temperature of 80° C. was slowly dropped into 500 mL of acetone (A solution) cooled to 5° C. with stirring the acetone solution at 15000 rpm. Then, the solution containing the polypropylene microparticles was recovered from Clearmix.

<Step c: Recovery and Washing>

The above-mentioned solution containing the polypropylene microparticles was filtrated to remove the supernatant so as to recover the polypropylene microparticles. After having been repeatedly washed with the washing solvent (acetone), a wet cake of the polypropylene microparticles was obtained.

Figure 22:
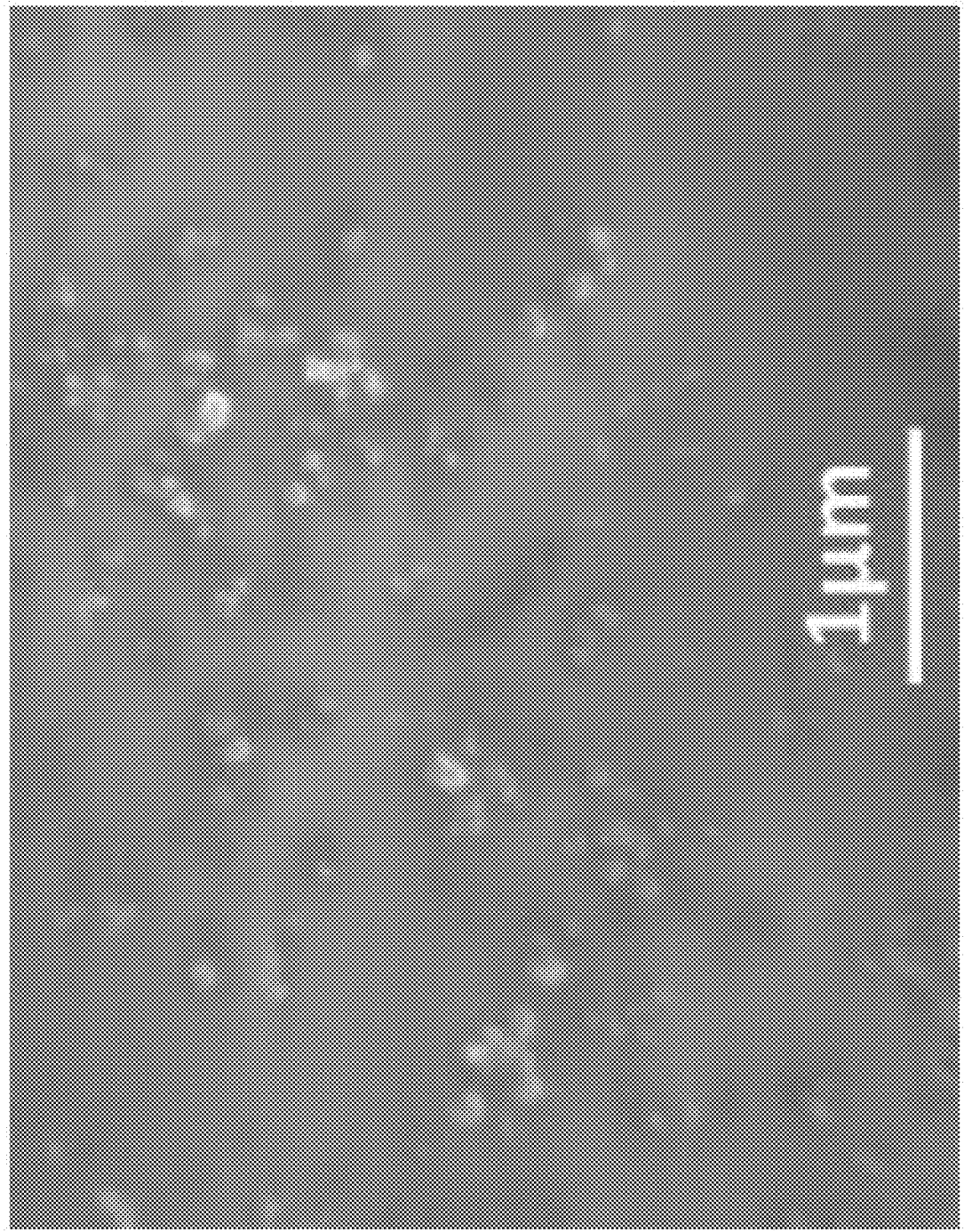
FIG. 22. This is the SEM picture of the polypropylene microparticles obtained in the step c in Example A7 of the present invention.
Figure 23:
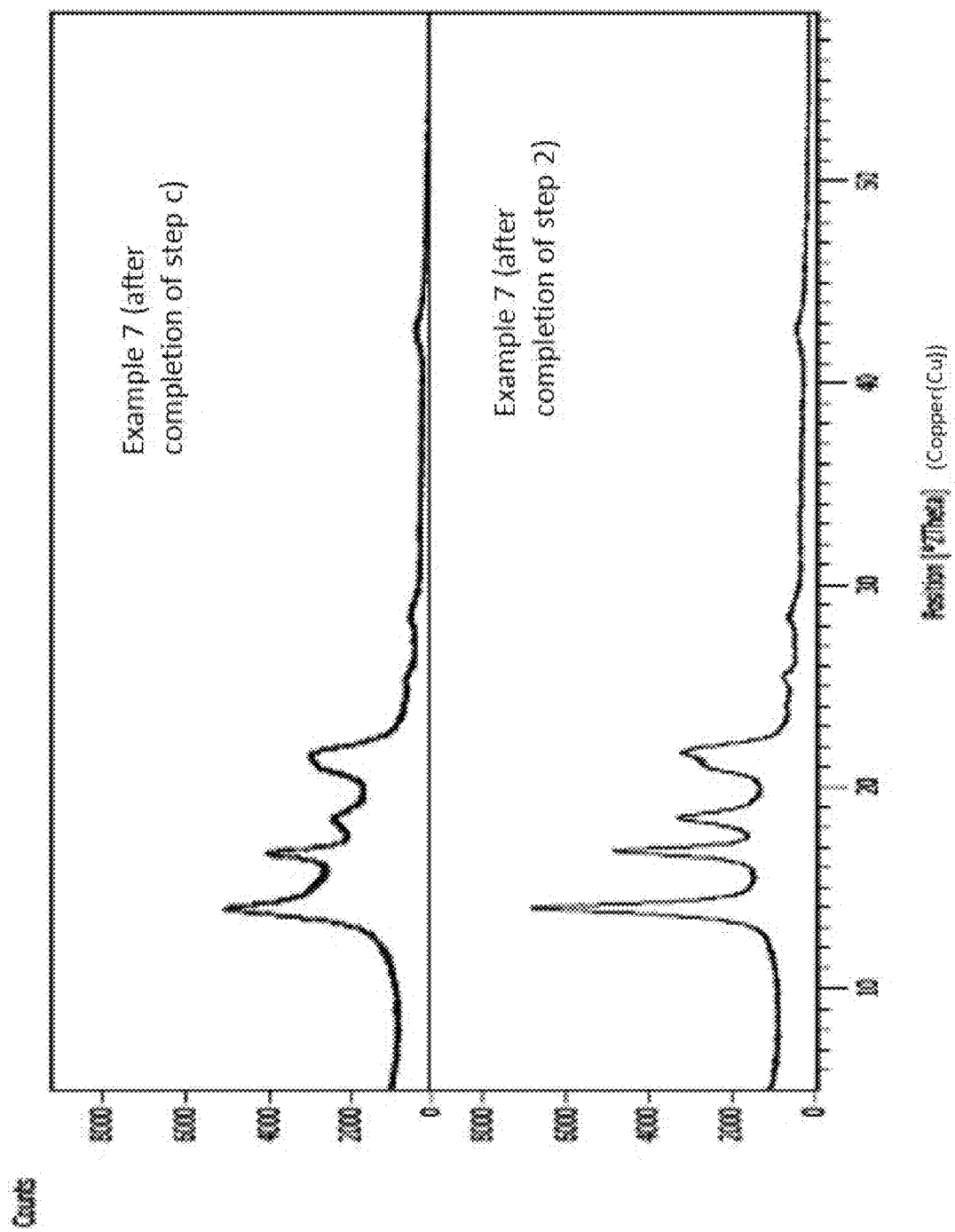
FIG. 23. These are the X-ray diffraction measurement results of the polypropylene microparticles obtained in the step c and the step 2 in Example A7 of the present invention.

The wet cake thus obtained was vacuum-dried at −0.095 MPaG for 16 hours to obtain the dried powder for the SEM observation and for the X-ray diffraction measurement. The SEM observation result is shown in FIG. 22, and the X-ray diffraction measurement result is shown in the upper column of FIG. 23.

From the SEM observation result, it was confirmed that the average primary particle diameter of the polypropylene microparticles was about 124 nm. From the X-ray diffraction measurement result, it was confirmed that the particles thus obtained were of the alpha-type crystal. Meanwhile, the degree of crystallinity thereof was 85.6%.

<Step 2: Control of the Particle Properties>

In the step 2 for control of the particle properties, an aqueous isopropanol solution (IPA+pure water) was used as the solvent which has a partial dissolvability to the organic material microparticle, and Tween 80 (manufactured by Wako Pure Chemical Industries, Ltd.) was used as the surfactant capable of suppressing the growth of the organic material microparticle. The aqueous isopropanol solution added with Tween 80 was stirred by using Clearmix Dissolver (product name: CLM-2.2SD, manufactured by M. Technique Co., Ltd.), a high-speed rotation type dispersing emulsifier, with the rotor's rotation number of 15000 rpm for the period of 30 minutes to obtain a uniformly mixed aqueous solution (particle property control solution). The wet cake of the polypropylene microparticles obtained in the step c was introduced into this particle property control solution, and then, the dispersion treatment thereof was conducted.

Figure 24:
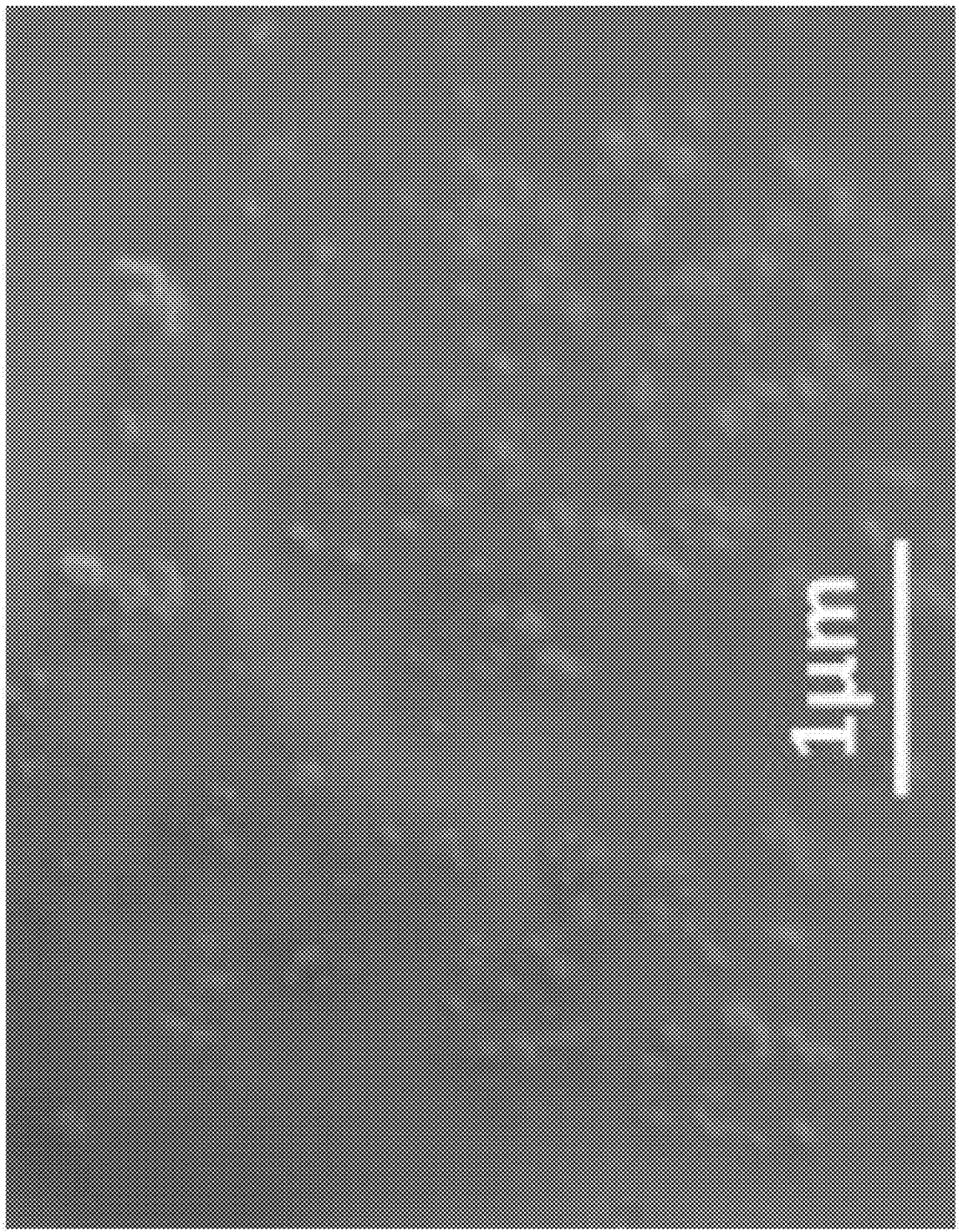
FIG. 24. This is the SEM picture of the polypropylene microparticles obtained in the step 2 in Example A7 of the present invention.

Specifically, the polypropylene microparticles obtained in the step c was added into the aqueous solution comprising 0.1% by weight of Tween 80, 2.0% by weight of isopropyl alcohol, and 97.9% by weight of water so as to give the concentration of the polypropylene microparticles of 0.2% by weight. Then, the resulting mixture was subjected to the dispersion treatment by using the ultrasonic disperser (UP 200S; manufactured by Heilscher Ultrasonics GmbH) with 0.5% output and 0.5 cycle and with the treatment temperature of 70±3° C. for the period of 15 minutes to obtain the dispersion solution of the polypropylene microparticles. From the obtained dispersion solution, the polypropylene microparticles were recovered by filtration, which was followed by vacuum-drying at −0.095 MPaG and with the temperature of 25° C. for 16 hours to obtain the dried powder for the SEM observation and for the X-ray diffraction measurement. The SEM observation result is shown in FIG. 24, and the X-ray diffraction measurement result is shown in the lower column of FIG. 23.

From the SEM observation result, it was confirmed that the average primary particle diameter of the polypropylene microparticles was about 197 nm. From the X-ray diffraction measurement result, it was confirmed that the crystal type of the obtained particle was of the alpha-type, the same as that of the polypropylene microparticle obtained in the step c. Meanwhile, the degree of crystallinity thereof was 93.5%; and thus, it was confirmed that the degree of crystallinity was higher than that of the polypropylene microparticle obtained in the step c. This is presumably because the amorphous portion contained in the polypropylene microparticles obtained in the steps 1 and 2 was crystallized.

Comparative Example A6

As the solvent for control of the particle properties in the step 2 of Example A7, only an isopropanol aqueous solution (2.0% by weight isopropyl alcohol/98.0% by weight water) was used as the solvent having a partial dissolvability to polypropylene without adding the surfactant. Then, the polypropylene microparticles were produced with the same conditions in the rest of the conditions as those of Example A7.

Figure 25:
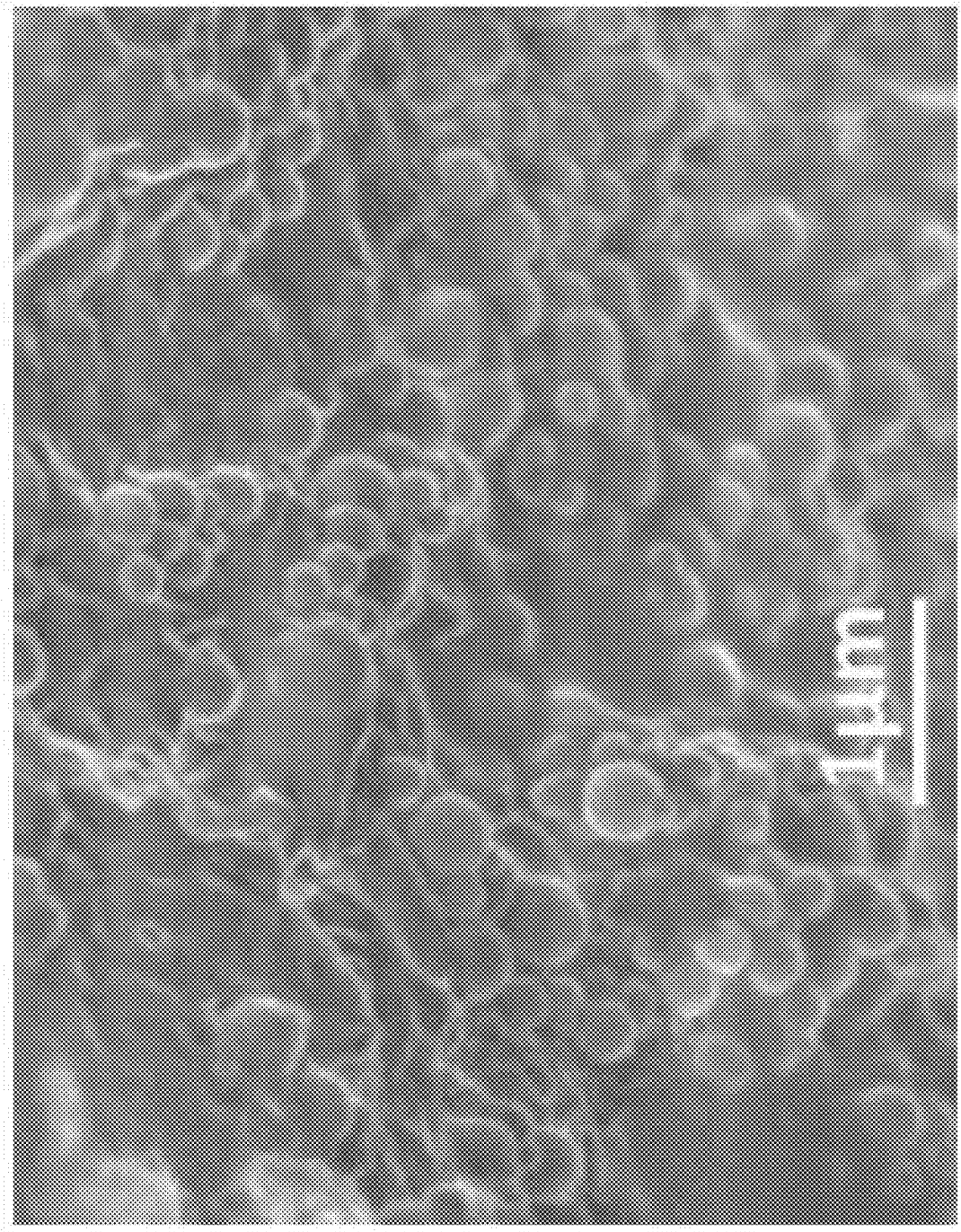
FIG. 25. This is the SEM picture of the polypropylene microparticles obtained in the step 2 in Comparative Example A6 of the present invention.

The SEM observation result thereof is shown in FIG. 25. From the SEM observation result, it was confirmed that the average primary particle diameter thereof was about 512 nm.

Example A8: Pirenoxine Microparticle

<Step 0: Preparation of the Separating Solvent of the Organic Material Microparticle (A Solution) and the Raw Material Solution of the Organic Material Microparticle (B Solution)>
<Preparation of the Separating Solvent of the Organic Material Microparticle (A Solution)>

The separating solvent of pirenoxine as the separating solvent of the organic material microparticle (A solution) was prepared by mixing citric acid with pure water so as to give its concentration of 1.9% by weight. The resulting mixture was stirred by using Clearmix (product name: CLM-2.2S, manufactured by M. Technique Co., Ltd.), a high-speed rotation type dispersing emulsifier, with the rotor's rotation number of 15000 rpm and the temperature of about 35° C. for the period of 30 minutes so as to prepare the uniform pirenoxine separating solvent. The pH of the pirenoxine separating solvent thus prepared was 2.1
<Preparation of the Raw Material Solution of the Organic Material Microparticle (B Solution)>

Pirenoxine was added into a 0.01 mol/L aqueous sodium hydroxide solution so as to give its concentration of 0.2% by weight, thereby the raw material pirenoxine solution was prepared as the raw material solution of the organic material microparticle (B solution). The resulting mixture was stirred by using Clearmix (product name: CLM-2.2S, manufactured by M. Technique Co., Ltd.), a high-speed rotation type dispersing emulsifier, with the rotor's rotation number of 15000 rpm and the temperature of about 35° C. for the period of 30 minutes so as to prepare the uniform raw material pirenoxine solution. The pH of the raw material pirenoxine solution thus prepared was 12.0.

<Step 1: Mixing and Separation>

Next, the prepared separating solvent of the organic material microparticle and the prepared raw material solution of the organic material microparticle were mixed by using the microreactor shown in FIG. 2 (A). Specifically, from the first introduction part d1 of the microreactor shown in FIG. 2 (A), the prepared pirenoxine separating solvent (here, 1.9% by weight of aqueous citric acid solution) was introduced as the first fluid to be processed (A solution) into between the processing surfaces with the supply rate of 300 mL/min and the temperature of 25° C.; and with operating the processing member 10 at the rotation number of 1700 rpm, the prepared raw material pirenoxine solution was introduced as the second fluid to be processed (B solution) into between the processing surfaces 1 and 2 with the supply rate of 20 mL/min and the temperature of 25° C. so as to mix them in a thin film fluid. Then, the solution containing the pirenoxine microparticles was discharged from the processing surfaces 1 and 2. The pH of the discharged solution containing the pirenoxine microparticles was 2.48.

Figure 26:
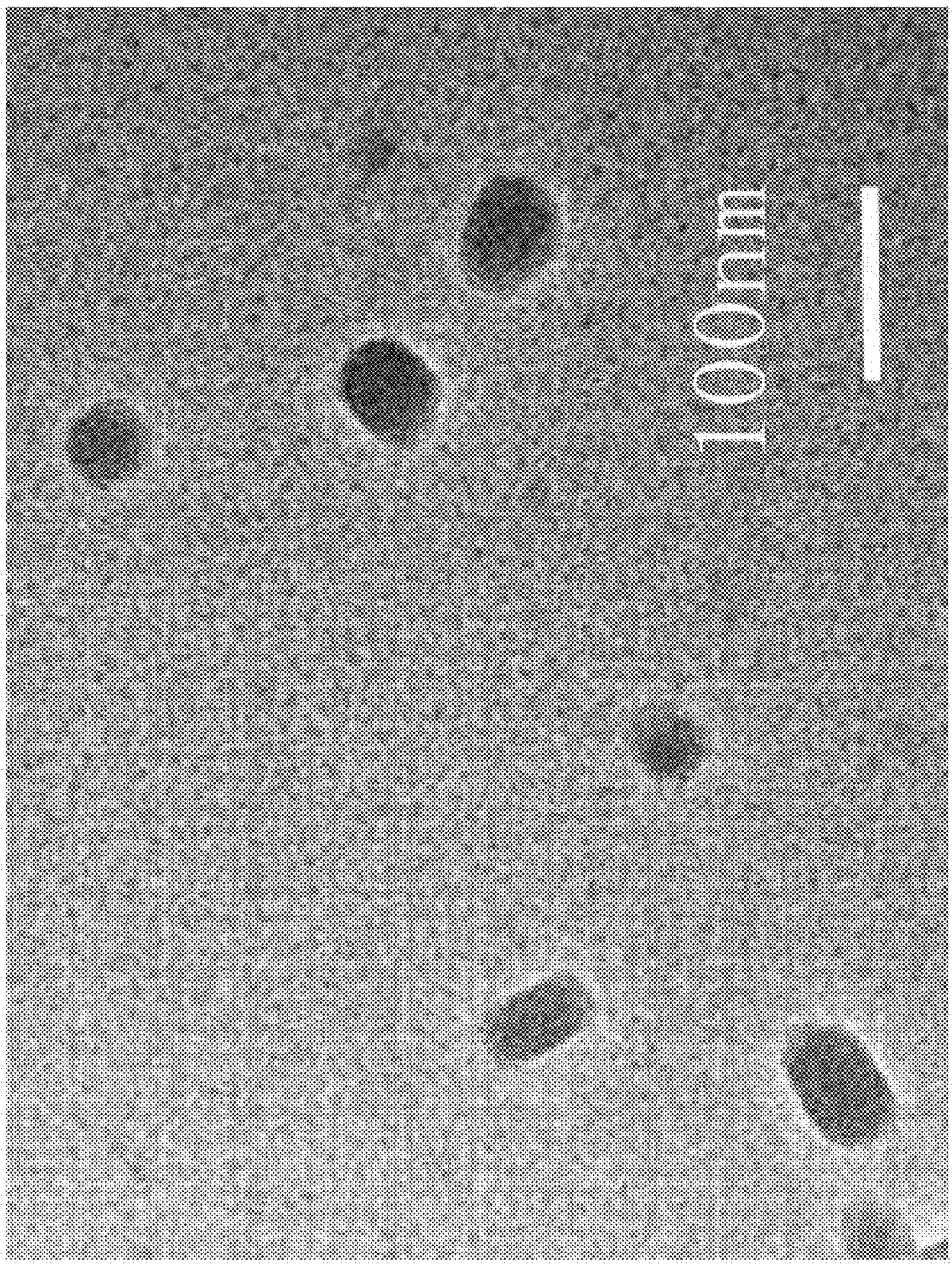
FIG. 26. This is the TEM picture of the pirenoxine microparticles obtained in the step 1 in Example A8 of the present invention.

The discharged solution containing the pirenoxine microparticles was dropped onto a collodion film and dried at room temperature to obtain the sample for observation, with which the TEM observation was conducted. From the TEM observation result, it was confirmed that the average primary particle diameter of the pirenoxine microparticles was about 42 nm. The TEM observation result is shown in FIG. 26.
<Step 2: Control of the Particle Properties>

In the step 2 for control of the particle properties, pure water was used as the solvent which has a partial dissolvability to the organic material microparticle, and Tween 80 and benzalkonium chloride were used as the surfactants capable of suppressing the growth of the organic material microparticle. Pure water added with Tween 80 and benzalkonium chloride was stirred by using Clearmix Dissolver (product name: CLM-2.2SD, manufactured by M. Technique Co., Ltd.), a high-speed rotation type dispersing emulsifier, with the rotor's rotation number of 15000 rpm for the period of 15 minutes to obtain a uniformly mixed aqueous solution of Tween 80 and benzalkonium chloride (particle property control solution). The dispersion solution of the pirenoxine microparticles obtained in the step 1 was introduced into this particle property control solution, and then, the dispersion treatment thereof was conducted.

Figure 27:
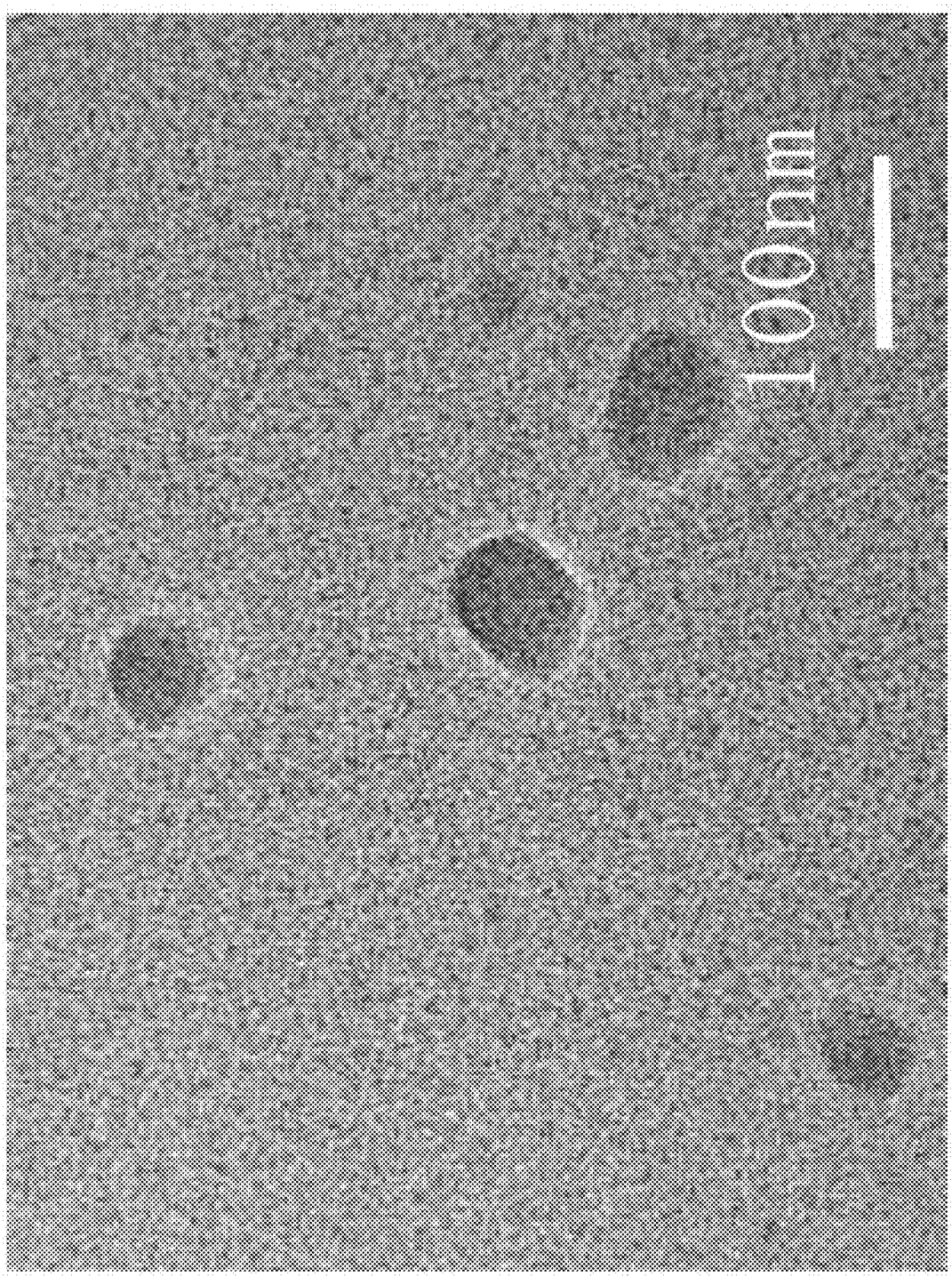
FIG. 27. This is the TEM picture of the pirenoxine microparticles obtained in the step 2 in Example A8 of the present invention.

Specifically, 500 g of the dispersion solution of the pirenoxine microparticles obtained in the step 1 was added into 500 g of the mixture solution comprising 0.03% by weight of Tween 80, 0.01% by weight of benzalkonium chloride, and 99.96% by weight of pure water. Then, the resulting mixture was subjected to the dispersion treatment by using Clearmix Double Motion (CLM-2.2/3.7W; manufactured by M. Technique Co., Ltd.) with the rotor's rotation number of 20000 rpm and the screen's rotation number of 18000 rpm and with the treatment temperature of 42±3° C. for the period of 30 minutes to obtain the dispersion solution of the pirenoxine microparticles. For the TEM observation, the obtained dispersion solution of the pirenoxine microparticles was dropped onto a collodion film, and then, it was dried at room temperature to obtain the sample for the observation. The TEM observation result thereof is shown in FIG. 27.

Figure 28:
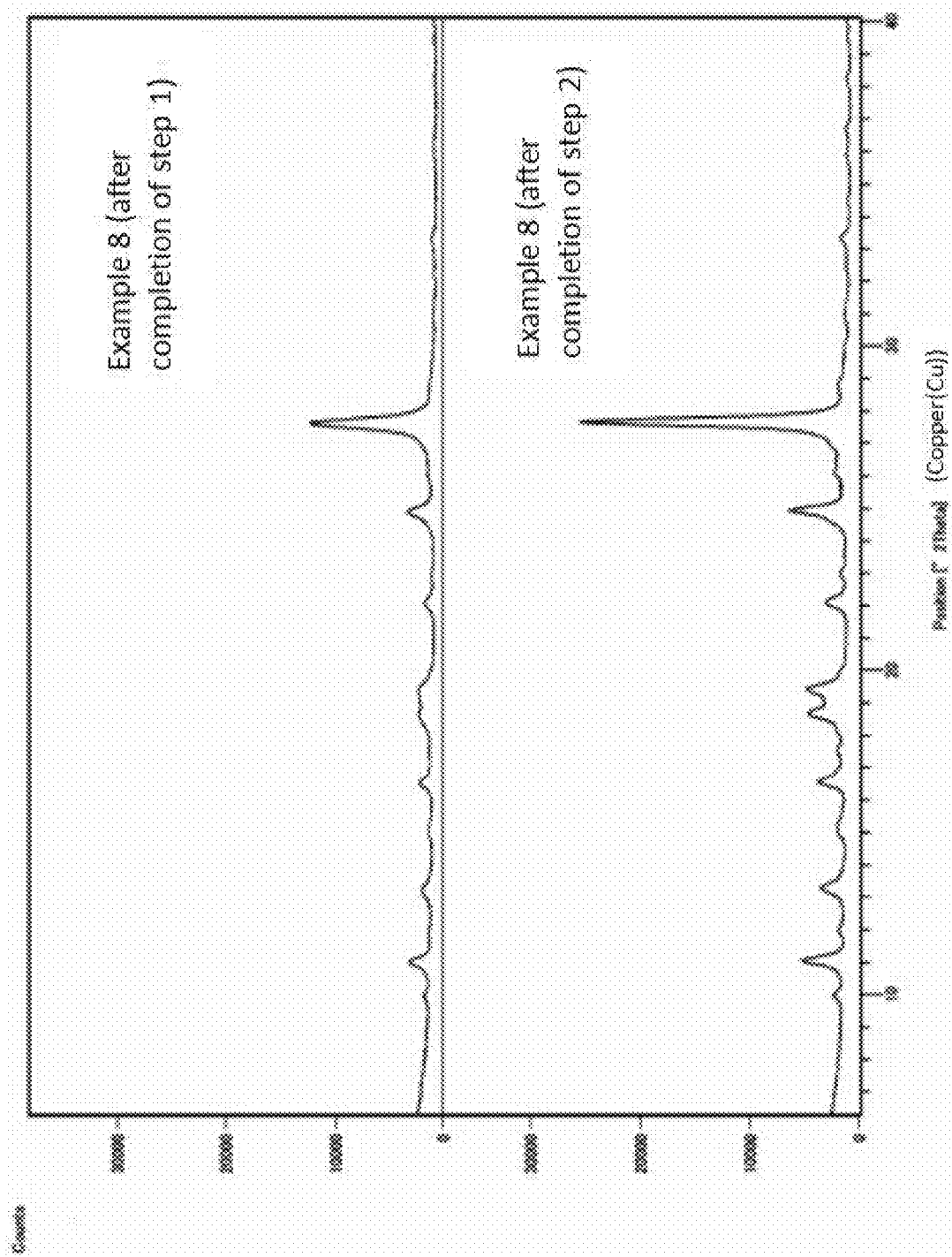
FIG. 28. These are the X-ray diffraction measurement results of the pirenoxine microparticles obtained in the step 1 (before the treatment in the step 2) and in the step 2 in Example A8 of the present invention.

From the TEM observation result, it was confirmed that the average primary particle diameter of the pirenoxine microparticles after having been subjected to the treatment with the aqueous solution containing Tween 80 was about 48 nm. Further, the pirenoxine microparticles were recovered from the dispersion solution by filtration; and after the microparticles were washed with pure water, they were vacuum-dried at −0.095 MPaG with the temperature of 25° C. for 16 hours to obtain the dried powder. The X-ray diffraction measurement result of the obtained dry powder is shown in the lower column of FIG. 28. Meanwhile, for a comparison purpose, the dispersion solution of the pirenoxine microparticles before being subjected to the dispersion treatment in the step 2 (discharged solution of the step 1) was recovered by filtration in the same way as before; and after the pirenoxine microparticles were washed with pure water, they were dried with the same condition as before. Then, the XRD diffraction measurement of the dry powder thus obtained was conducted. The result thereof is shown in the upper column of FIG. 28. From the XRD diffraction measurement result, it was confirmed that the degree of crystallinity after the dispersion treatment in the step 2 was 63.2%, which was increased from 58.1% as the degree of crystallinity, the value before the dispersion treatment in the step 2. In addition, from the XRD diffraction measurement thereof, it was confirmed that there was no change in the crystal type of the obtained particles before and after the treatment.

The results of Example A1 to A8 and Comparative Examples A1 to A6 are summarized in Table 1.

primary particle diameter after the treatment in the step 2 relative to the value (Xb) of the average primary particle diameter before the treatment in the step 2, namely after completion of the treatment in the step c (after the treatment in the step 1 only in Example A8). With regard to pirenoxine, because generally the name of crystal type is not used, the column of the crystal type of Example A8 in Table 1 is shown by the symbol "x", with which it is indicated that there was no change in the crystal type before and after the treatment of the step 2.

From the results of Examples A1 and A2 and Comparative Example A1, it can be seen that in pure water, the solvent which has a partial dissolvability to indomethacin, the indomethacin microparticle becomes coarse, but when the particle property control is conducted in the step 2 in which the surfactant capable of suppressing the growth of the organic material microparticle is added to the said solvent, the particle diameter of the indomethacin microparticle does not substantially change, thereby the coarsening of the particle can be suppressed. In addition, it can be seen that when the particle property control of the step 2 is conducted, the crystal transition from the amorphous to the alpha-type can take place.

In addition, from the results of Examples A1 and A2 and Example A3, it was confirmed that even if the solvent which

TABLE 1

| | | After step c (after step 1 only in Example 8) | | | After step 2 | | | | | |
|---|---|---|---|---|---|---|---|---|---|---|
| | Organic microparticle | Xb: Average primary particle diameter (nm) | Degree of crystallinity | Crystal type | Step 2 Solvent | Surfactant | Xa: Average primary particle diameter (nm) | Degree of crystallinity | Crystal type | Rate of change in average primary particle diameter | Xa/Xb: Rate of change in degree of crystallinity |
| Example 1 | Indomethacin | 76 | — | — | Pure water | HEC | 98 | 42.45 | α | 1.29 | Crystallized |
| Example 2 | Indomethacin | 76 | — | — | Pure water | HEC | 126 | 38.18 | α | 1.66 | Crystallized |
| Comparative Example 1 | Indomethacin | 76 | — | — | Pure water | None | 850 | 45.50 | α | 11.18 | Crystallized |
| Example 3 | Indomethacin | 76 | — | — | Hexane | Span 80 | 138 | 39.76 | γ | 1.82 | Crystallized |
| Comparative Example 2 | Indomethacin | 76 | — | — | Hexane | None | 1000 | 45.04 | γ | 13.16 | Crystallized |
| Example 4 | Indomethacin | 146 | 50.0 | α | Pure water | Lutrol F127 | 168 | 62.5 | α | 1.15 | 1.25 |
| Comparative Example 3 | Indomethacin | 146 | 50.0 | α | Pure water | None | 1160 | 65.0 | α | 7.95 | 1.30 |
| Example 5 | Curcumin | 88 | — | — | Pure water | PVA 500 (completely saponified) | 108 | 39.36 | 3 | 1.23 | Crystallized |
| Comparative Example 4 | Curcumin | 88 | — | — | Pure water | None | 980 | 35.64 | 3 | 11.14 | Crystallized |
| Example 6 | Curcumin | 88 | — | — | Hexane | Span 80 | 97 | 36.65 | 2 | 1.10 | Crystallized |
| Comparative Example 5 | Curcumin | 88 | — | — | Hexane | None | 1000 | 35.94 | 3 | 11.36 | Crystallized |
| Example 7 | Polypropylene | 124 | 85.6 | α | IPA + Pure water | Tween 80 | 197 | 93.5 | α | 1.59 | 1.09 |
| Comparative Example 6 | Polypropylene | 124 | 85.6 | α | IPA + Pure water | None | 512 | 91.2 | α | 4.12 | 1.07 |
| Example 8 | Pirenoxine | 42 | 58.1 | x | Pure water | Tween 80 + benzalkonium chloride | 48 | 63.2 | x | 1.14 | 1.08 |

Meanwhile, the symbol "-" shown in the column of "Degree of crystallinity" in Table 1 indicates that the crystallinity is amorphous. The degree of crystallinity is measured with XRD as mentioned before; and the rate of change in the degree of crystallinity is defined as the rate (Xa/Xb), that is, with regard to before and after the treatment with the particle property control solution of the organic material microparticle in the step 2, the value (Xa) of the average has a partial dissolvability to indomethacin and the surfactant capable of suppressing the growth of indomethacin are changed, the effects of the particle property control of the step 2 can be obtained.

From the results of Examples A1 to A4, it can be seen that the effects of the particle property control in the step 2 is not dependent on the crystal type of indomethacin. Further, it can be seen that when the particle property control of the step 2 was conducted, not only the crystal transition took place but also the degree of crystallinity increased.

As shown in Examples A5 to A8 and Comparative Examples A4 to A6, it is shown that the above-mentioned effects can be expressed not only in indomethacin in Examples A1 to A4 but also in other organic material microparticles.

Further, from the result of Example A8, it was confirmed that even if the step c in which washing and/or solvent substitution is conducted to the organic material microparticle obtained in the step 1 is omitted, the effects of the particle property control of the step 2 can be obtained.

Group of Examples B

Hereunder, the group of Examples B (red organic pigments) will be explained.

For the XRD measurement of Examples B, the powder X-ray diffraction measurement apparatus (product name: X'Pert PRO MPD, manufactured by PANalytical B. V.) was used. The measurement conditions were as follows: measurement range of 6 to 60°, Cu anticathode, tube voltage of 45 kV, tube current of 40 mA, and scanning speed of 16°/min.

For the TEM observation, the transmission electron microscope JEM-2100 (manufactured by JEOL Ltd.) was used. The observation conditions with the acceleration voltage of 80 kV and the observation magnification of 25000 were employed.

(Case of the Batch Method)

Similarly to Examples A, the pigment microparticles were produced according to the step 0 to step 2 as illustrated in FIG. 1.

(Step 0)

Preparation of the separating solvent of the pigment microparticle (A solution) and the raw material solution of the pigment microparticle (B solution) shown in Table 2 below: both the A and B solutions were prepared by stirring the respective solutions by means of a magnetic stirrer and a stirring bar at the rotation number of 300 rpm for the period of 30 minutes with the temperature of 40° C.

(Step 1)

Mixing of the A and B solutions: as shown in Table 2 below, the B solution was introduced into the A solution with stirring the A solution by means of a magnetic stirrer and a stirring bar at the rotation number of 300 rpm, resulting in separation of the organic pigment microparticles. Meanwhile, after the slurry containing the organic pigment microparticles obtained in the step 1 were filtrated, the organic pigment microparticles were washed with pure water (step c), thereby a wet cake of the organic pigment microparticles was obtained. Alternatively, by conducting the drying treatment of the organic pigment microparticles with the method such as a vacuum-drying method, the dried powder thereof was obtained.

(Step 2)

The wet cake or the dry powder of the organic pigment microparticles mentioned above was introduced into a solvent having a partial dissolvability to the organic material microparticle (particle property control solution) and having a surfactant or a dispersant added therein. The resulting mixture was subjected to the stirring treatment for a prescribed time by using the Clearmix CLM-2.2S stirrer equipped with a rotating and stirring blade.

TABLE 2

| Experiment No. | A solution | Amount of A solution (mL) | Temperature of A solution (° C.) | B solution | Charge rate of B solution (mL/min) | Charge time of B solution (min) | Temperature of B solution introduced (° C.) |
|---|---|---|---|---|---|---|---|
| a-1 to a-11 | 20 wt % acetic acid/pure water | 500 | 5.2 | DMSO/40 wt % BTMA MeOH soln/PR 254 63/28/9 (weight ratio) | 50 | 1 | 40.2 |
| b-1 to b-3 | 20 wt % acetic acid/pure water | 800 | 5.3 | DMSO/40 wt % BTMA MeOH soln/PR 122 63/28/9 (weight ratio) | 30 | 1 | 40.6 |

The abbreviations used are as follows; DMSO: dimethyl sulfoxide, BTMA: benzyl trimethyl ammonium hydroxide, MeOH: methanol, soln: solution, PR 254: C. I. Pigment Red 254, PR 122: C. I. Pigment Red 122.

After washing in the step c, with regard to each of the pigment microparticles after stirring in the step 2, the average primary particle diameter was calculated with the TEM observation, and the degree of crystallinity was measured with the XRD measurement; and they were compared to each other (see, Table 3 shown below). Here, the degree of crystallinity is defined as the ratio of the crystallized portion relative to the total of the crystallized portion and the amorphous portion, wherein when the degree of crystallinity of the pigment is higher, durability to light, heat, humidity, or the like becomes higher. Meanwhile, definitions of the symbols ⊚, ○, Δ, and X are as follows.

When Da is defined as the average primary particle diameter of the particles after the action of the step 2, and Db is defined as the average primary particle diameter before the step 2 and after the washing, the symbol ⊚ is defined as follows:

Da/Db is in the range of 1.0 and 4.0, and when Xa designates the degree of crystallinity of the particles after the action of the step 2 and Xb designates the degree of crystallinity before the step 2 and after the washing, Xa/Xb is in the range of 1.05 or more, and Da is in the range of 80 nm or less, and in view of uniformity of the microparticles, at the time of TEM observation of three view fields with 25000 magnification, the particles having the size of more than 8.0 times relative to Db are not found at all among the individual pigment microparticles after the step 2 (after the action).

The symbol ○ is defined as follows:
Da/Db is in the range of 1.0 and 4.0, and
Xa/Xb is in the range of 1.05 or more, and
Da is in the range of more than 80 nm, and
in view of uniformity of the microparticles, at the time of TEM observation of three view fields with 25000 magnification, the particles having the size of more than 8.0 times relative to Db are not found at all among the individual pigment microparticles after the step 2 (after the action).

The symbol Δ is defined as follows:
Da/Db is in the range of 1.0 and 4.0, and
Xa/Xb is in the range of 1.05 or more, and
in view of uniformity of the microparticles, at the time of TEM observation of three view fields with 25000 magnification, a maximum of one particle having the size of more than 8.0 times relative to Db is found among the individual pigment microparticles after the step 2 (after the action).

The symbol X is defined when any of ⊚, ○, and Δ is not applicable.

Meanwhile, the average particle diameter was obtained with the measurement of total 100 microparticles observed in plural view fields at the time of TEM observation with 25000 magnifications.

The solutions A and B were mixed in the microreactor with the operation, the condition of which are shown in Table 4 below; and similarly to Examples A, pigment microparticles were produced according to the step 0 to the step 2 shown in FIG. 1.

(Step 0)

Preparation of the separating solvent for the pigment microparticle (A solution) and the raw material solution of the pigment microparticle solution (B solution) described in Table 5: both the A and B solutions were prepared by using the above-mentioned Clearmix CLM-2.2S for 30 minutes with the liquid temperature of 40° C., while the rotation numbers thereof were 10000 rpm for the A solution and 20000 rpm for the B solution.

(Step 1)

The dissolved solution of the organic pigment (B solution) was mixed with the poor solvent (A solution) by using the microreactor shown in FIG. 1 to separate the organic pigment microparticles. The slurry containing the organic pigment microparticles obtained in the step 1 was filtrated; and the microparticles thus recovered were washed with pure water (step c) to obtain a wet cake of the organic pigment microparticles, or the dried powder of the organic pigment microparticles by conducting the drying treatment thereof with a vacuum-drying or the like.

TABLE 3

| Experiment No. | Step c washing | | | Step 2 Stirring | | | | | | | |
|---|---|---|---|---|---|---|---|---|---|---|---|
| | Separation method | Average primary particle diameter (nm) | Crystal type | Solvent | Surfactant/ dispersant | Ratio of surfactant/ dispersant to pigment (% by weight) | Average primary particle diameter (nm) | Crystal type | Step c → 2 Change in particle diameter [Da/Db] | Step c → 2 Change in degree of crystallinity [Xa/Xb] | Judgement | Example/ Comparative Example |
| a-1 | Batch | 124.1 | β | PGMEA | — | — | 999.6 | α | 8.05 | 1.97 | X | C. Example |
| a-2 | Batch | 124.1 | β | PGMEA | BYK-2000 | 100 | 197.8 | α | 1.59 | 2.31 | ○ | Example |
| a-3 | Batch | 124.1 | β | PGMEA | BYK-108 | 100 | 213.4 | α | 1.72 | 2.16 | ○ | Example |
| a-4 | Batch | 124.1 | β | PGMEA | Pelex TR | 100 | 312.1 | α | 2.51 | 3.16 | ○ | Example |
| a-5 | Batch | 124.1 | β | PGMEA | BYK-2164 | 100 | 249.6 | α | 2.01 | 1.36 | Δ | Example |
| a-6 | Batch | 124.1 | β | MeOH | — | — | 1012.3 | α | 8.16 | 4.16 | X | C. Example |
| a-7 | Batch | 124.1 | β | PGME | — | — | 1006.6 | α | 8.11 | 2.13 | X | C. Example |
| a-8 | Batch | 124.1 | β | Toluene | — | — | 1111.1 | β | 8.95 | 1.02 | X | C. Example |
| a-9 | Batch | 124.1 | β | MEK | — | — | 1213.4 | α | 9.78 | 1.39 | X | C. Example |
| a-10 | Batch | 124.1 | β | MeOH | BYK-2000 | 100 | 146.30 | α | 1.18 | 2.13 | ○ | Example |
| a-11 | Batch | 124.1 | β | Toluene | BYK-2000 | 100 | 159.4 | β | 1.28 | 2.39 | ○ | Example |
| b-1 | Batch | 136.9 | α | IPA | — | — | 1634.6 | β | 11.94 | 2.36 | X | C. Example |
| b-2 | Batch | 136.9 | α | IPA | BYK-2000 | 100 | 412.3 | β | 3.01 | 3.49 | ○ | Example |
| b-3 | Batch | 136.9 | α | IPA | BYK-2164 | 100 | 463.1 | β | 3.38 | 1.69 | ○ | Example |

(Case of Using the Microreactor)

In Examples B, the A solution corresponds to the first fluid to be processed which is introduced from the first introduction part d1 of the microreactor shown in FIG. 2 (A), and the B solution corresponds to the second fluid to be processed which is introduced from the second introduction part d2 of the same. Both the solutions are interchangeable with each other. Meanwhile, in Examples B, ULREA (manufactured by M. Technique Co., Ltd.) was used as the microreactor.

(Step 2)

The wet cake of the organic pigment microparticles or the dry powder thereof was introduced into the solvent having a partial dissolvability to the organic pigment microparticle and having a surfactant or a dispersant added therein (particle property control solution); and then, the resulting mixture was subjected to the stirring treatment for a prescribed time by using the above-mentioned Clearmix CLM-2.2S.

TABLE 4

| Experiment No. | Disk rotation number (rpm) | A solution supply condition | | B solution supply condition | | Discharged solution | |
|---|---|---|---|---|---|---|---|
| | | Flow rate (mL/min) | Temperature (° C.) | Flow rate (mL/min) | Temperature (° C.) | pH | Measured temperature (° C.) |
| 1-1 to 1-11 | 1700 | 500 | 5.1 | 50 | 40.1 | 2.45 | 26.4 |
| 2-1 to 2-3 | 1700 | 800 | 5.2 | 30 | 40.2 | 2.08 | 21.4 |

TABLE 5

| Experiment No. | A solution | B solution |
|---|---|---|
| 1-1 to 1-11 | 20 wt % acetic acid/pure water | DMSO/40 wt % BTMA MeOH soln/PR254 63/28/9 (weight ratio) |
| 2-1 to 2-3 | 20 wt % acetic acid/pure water | DMSO/40 wt % BTMA MeOH soln/PR122 63/28/9 (weight ratio) |

Next, similarly to the batch method, the pigment microparticles obtained in the steps 1 and 2 were compared with each other by calculating the average primary particle diameters with the TEM observation and measuring the degrees of crystallinity with the XRD measurement of them (see, Table 6 below). Meanings of the symbols and abbreviations are as same as those of the batch method. Also, definitions of the symbols ⊚, ○, Δ, and X are the same as those of the batch method.

Group of Examples C

Next, the group of Examples C (blue organic pigment) will be explained.

For the XRD measurement of Examples C, the powder X-ray diffraction measurement apparatus (product name: X'Pert PRO MPD, manufactured by PANalytical B. V.) was used. The measurement conditions were as follows: measurement range of 6 to 60°, Cu anticathode, tube voltage of 45 kV, tube current of 40 mA, and scanning speed of 16°/min.

For the TEM observation, the transmission electron microscope JEM-2100 (manufactured by JEOL Ltd.) was used. The observation conditions with the acceleration voltage of 80 kV and the observation magnification of 25000 were employed.

TABLE 6

| Experiment No. | Step c washing | | | Step 2 Stirring | | | | Step c → 2 Change in particle diameter [Da/Db] | Step c → 2 Change in degree of crystallinity [Xa/Xb] | Judgement | Example/ Comparative Example |
|---|---|---|---|---|---|---|---|---|---|---|---|
| | Separation method | Average primary particle diameter (nm) | Crystal type | Solvent | Surfactant/ dispersant | Ratio of surfactant/ dispersant to pigment (% by weight) | Average primary particle diameter (nm) | Crystal type | | | | |
| 1-1 | ULREA | 11.1 | β | PGMEA | — | — | 101.1 | α | 9.11 | 1.46 | X | C. Example |
| 1-2 | ULREA | 11.1 | β | PGMEA | BYK-2000 | 100 | 16.4 | α | 1.48 | 2.31 | ⊚ | Example |
| 1-3 | ULREA | 11.1 | β | PGMEA | BYK-108 | 100 | 26.3 | α | 2.37 | 2.16 | ⊚ | Example |
| 1-4 | ULREA | 11.1 | β | PGMEA | Pelex TR | 100 | 24.9 | α | 2.24 | 3.16 | ⊚ | Example |
| 1-5 | ULREA | 11.1 | β | MeOH | — | — | 41.1 | α | 3.70 | 4.16 | Δ | C. Example |
| 1-6 | ULREA | 11.1 | β | Acetone | — | — | 24.1 | α | 2.17 | 3.16 | Δ | C. Example |
| 1-7 | ULREA | 11.1 | β | PGME | — | — | 18.1 | α | 1.63 | 2.13 | Δ | C. Example |
| 1-8 | ULREA | 11.1 | β | Toluene | — | — | 134.6 | β | 12.13 | 1.02 | X | C. Example |
| 1-9 | ULREA | 11.1 | β | MEK | — | — | 19.6 | α | 1.77 | 1.39 | Δ | C. Example |
| 1-10 | ULREA | 11.1 | β | MeOH | BYK-2000 | 100 | 12.1 | α | 1.09 | 2.13 | ⊚ | Example |
| 1-11 | ULREA | 11.1 | β | Toluene | BYK-2000 | 100 | 16.9 | β | 1.52 | 1.97 | ⊚ | Example |
| 2-1 | ULREA | 13.4 | α | IPA | — | — | 34.1 | β | 2.54 | 2.36 | X | C. Example |
| 2-2 | ULREA | 13.4 | α | IPA | BYK-2000 | 100 | 15.6 | β | 1.16 | 3.49 | ⊚ | Example |
| 2-3 | ULREA | 13.4 | α | IPA | BYK-2164 | 100 | 29.6 | β | 2.21 | 1.69 | ⊚ | Example |

Figure 30:
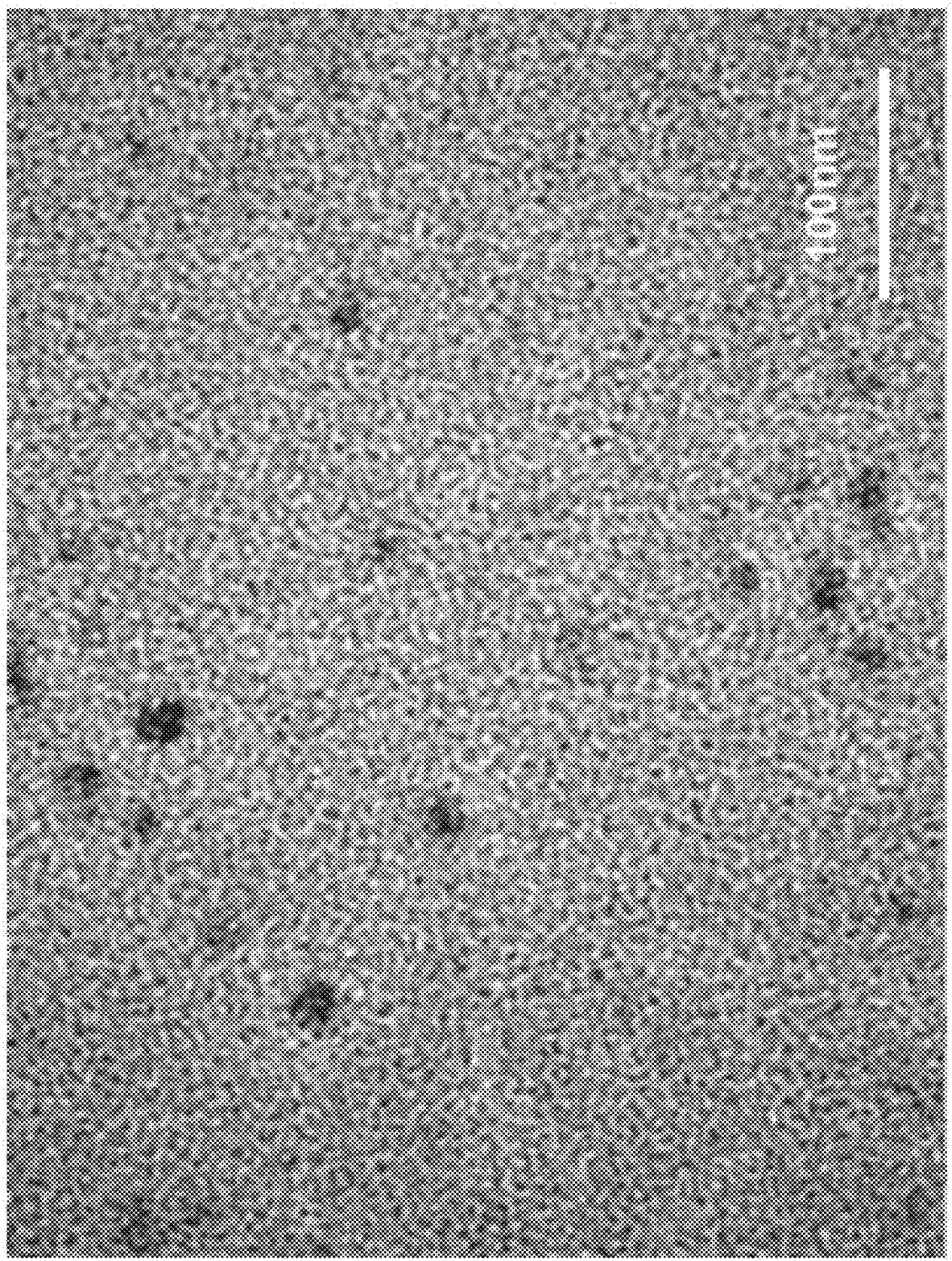
FIG. 30. This is the picture observed with the transmission electron microscope (TEM) of the red pigment nanoparticles of the present invention produced in the step 2 of Experiment No. 1-2 of Examples B.

From the TEM picture of the red pigment nanoparticles of the present invention obtained in Experiment No. 1-2 of Examples B (FIG. 30), it became clear that when the production method of the present invention is applied to Examples B, owing to the action of the particle property control solution, the necking and growth in the obtained red organic pigment microparticles can be suppressed.

Meanwhile, Experiment No. 2-1 is regarded as Comparative Example, because at the time of the above-mentioned TEM observation, two or more of the particle having the size of more than 8.0 times relative to Db were confirmed among the individual pigment microparticles in the step 2 (after the action).

(Case of Using the Microreactor)

The A solution and the B solution were mixed with the condition shown below, and by following the procedure shown below, the blue organic pigment microparticles were produced.

Meanwhile, in Examples C, ULREA (manufactured by M. Technique Co., Ltd.) was used as the microreactor. In this case, the A solution corresponds to the first fluid to be processed which is introduced from the first introduction part d1 of the microreactor shown in FIG. 2 (A), and the B solution corresponds to the second fluid to be processed which is introduced from the second introduction part d2 of the same. The first introduction part d1 and the second introduction part d2 are interchangeable with each other.

The experimental prescriptions of Examples C are shown in Table 7.

TABLE 7

| Experiment No. | A solution | | | B solution | | |
|---|---|---|---|---|---|---|
| | Prescription | pH | Measured temperature (° C.) | Prescription | pH | Measured temperature (° C.) |
| 1 | Pure water | 6.9 | 13.9 | CuPc/TiOPc/CoPc/$H_2SO_4$ = 2.1/0.6/0.3/97 (weight ratio) | <1 | — |
| 2 | Pure water | 6.9 | 13.9 | CuPc/TiOPc/CoPc/$H_2SO_4$ = 2.1/0.45/0.45/97 (weight ratio) | <1 | — |
| 3 | Pure water | 6.9 | 13.9 | CuPc/$H_2SO_4$ = 3/97 (weight ratio) | <1 | — |

Meanwhile, the abbreviations used in the above are as follows; CuPc: copper phthalocyanine, TiOPc: titanyl phthalocyanine, CoPc: cobalt phthalocyanine, and $H_2S_4O$: concentrated sulfuric acid.

In Examples C, too, similarly to Examples A, the pigment microparticles were produced according to the steps 0 to 2 shown in FIG. 1.

(Step 0)

For mixing and separation with the experimental prescriptions described above by using ULREA, the A solution and the B solution were prepared in the way as described below.
Preparation Condition of the Separating Solvent of the Organic Pigment Particles (A Solution):

As described in the experimental prescriptions above, in the case of a single solvent, preparation thereof is not necessary; however, for example, in the case that the experimental prescription described in Patent Document 8 is used, it is preferable to stir by using Clearmix. For example, in Examples C, stirring is conducted by using CLM-2.2S with the rotation number of 10000 rpm for the period of 30 minutes.
Preparation Condition of the Raw Material Solution of the Organic Pigment Particles (B Solution):

Stirring was conducted by using Clearmix CLM-2.2S with the rotation number of 20000 rpm for the period of 30 minutes. The preparation temperatures of both the A solution and the B solution were made 40° C.

(Step 1)

With the operation conditions described in Table 8 shown below, by using ULREA, the separating solvent of the organic pigment particles (A solution) and the raw material solution of the organic pigment particles (B solution) were mixed to separate the blue organic pigment microparticles.

The slurry containing the blue organic pigment microparticles obtained in the step 1 was filtrated; and the blue organic pigment microparticles thus recovered were washed with pure water (step c) to obtain a wet cake of the blue organic pigment microparticles (or the dried powder of the blue organic pigment microparticles obtained by conducting the drying treatment thereof with a vacuum-drying or the like).

(Step 2)

The wet cake of the blue organic pigment microparticles (or the dry powder thereof) obtained in the step 1 was introduced into the solvent which has a partial dissolvability to the organic pigment microparticle solely, or into the said solvent added with a surfactant and/or a dispersant (particle property control solvent); and then, the resulting mixture was subjected to the stirring treatment for a prescribed time by using Clearmix.

TABLE 8

| Experiment No. | Disk rotation number (rpm) | Supply condition of A solution | | Supply condition of B solution | | Discharged solution | |
|---|---|---|---|---|---|---|---|
| | | Flow rate (mL/min) | Temperature (° C.) | Flow rate (mL/min) | Temperature (° C.) | pH | Measured temperature (° C.) |
| 1 | 1700 | 600 | 10.1 | 30 | 40.6 | <1 | 23.1 |
| 2 | 1700 | 600 | 10.2 | 30 | 40.1 | <1 | 22.9 |
| 3 | 1700 | 600 | 10.4 | 30 | 41.2 | <1 | 22.9 |

The changes in the particle diameter and degree of crystallinity of the blue organic pigment microparticles before and after the stirring treatment in the case of using the microreactor are shown in Table 9 below.

TABLE 9

| Experiment No. | Pigment | Separation apparatus | Particle properties after step c (washing) | | Step 2 (action) | | | Particle properties after step 2 (action) | | Change of particle diameter before and after the action (Da/Db) | Change of degree of crystallinity before and after the action (Xa/Xb) | Judgement | Example/ Comparative Example |
|---|---|---|---|---|---|---|---|---|---|---|---|---|---|
| | | | Average primary particle diameter: Db (nm) | Crystal type | Solvent | Surfactant/ dispersant | Ratio of surfactant/ dispersant to pigment (wt %) | Average primary particle diameter: Da (nm) | Crystal type | | | | |
| 1-1 | Plural | ULREA | 9.8 | α | Styrene | — | | 54.9 | α | 5.60 | 2.31 | X | Comparative Example |
| 1-2 | Plural | ULREA | 9.8 | α | Toluene | — | | 61.9 | α | 6.32 | 1.65 | X | Comparative Example |
| 1-3 | Plural | ULREA | 9.8 | α | Xylene | — | | 46.9 | α | 4.79 | 1.39 | X | Comparative Example |
| 1-4 | Plural | ULREA | 9.8 | α | THF | — | | 40.9 | α | 4.17 | 1.36 | X | Comparative Example |
| 1-5 | Plural | ULREA | 9.8 | α | IPA | — | | 41.2 | α | 4.20 | 1.01 | X | Comparative Example |
| 1-6 | Plural | ULREA | 9.8 | α | Styrene | Pelex TR | 100 | 19.3 | α | 1.97 | 1.19 | ◎ | Example |
| 1-7 | Plural | ULREA | 9.8 | α | Styrene | BYK-2164 | 100 | 11.2 | α | 1.14 | 2.31 | ◎ | Example |
| 1-8 | Plural | ULREA | 9.8 | α | Styrene | BYK-2000 | 100 | 33.1 | α | 3.38 | 2.64 | ◎ | Example |
| 1-9 | Plural | ULREA | 9.8 | α | Styrene | BYK-108 | 100 | 24.1 | α | 2.46 | 2.39 | ◎ | Example |
| 1-10 | Plural | ULREA | 9.8 | α | THF | BYK-2164 | 100 | 21.4 | α | 2.18 | 2.46 | △ | Example |
| 1-11 | Plural | ULREA | 9.8 | α | IPA | BYK-2001 | 100 | 18.9 | α | 1.93 | 1.49 | ◎ | Example |
| 2-1 | Plural | ULREA | 8.6 | α | Styrene | — | | 49.8 | α | 5.79 | 3.12 | X | Comparative Example |
| 2-2 | Plural | ULREA | 8.6 | α | Toluene | — | | 46.9 | α | 5.45 | 3.23 | X | Comparative Example |
| 2-3 | Plural | ULREA | 8.6 | α | Xylene | — | | 47.8 | α | 5.56 | 2.16 | X | Comparative Example |
| 2-4 | Plural | ULREA | 8.6 | α | THF | — | | 49.6 | α | 5.77 | 1.69 | X | Comparative Example |
| 2-5 | Plural | ULREA | 8.6 | α | IPA | — | | 43.9 | α | 5.10 | 1.03 | X | Comparative Example |
| 2-6 | Plural | ULREA | 8.6 | α | Styrene | Pelex TR | 100 | 14.5 | α | 1.69 | 1.46 | ◎ | Example |
| 2-7 | Plural | ULREA | 8.6 | α | Styrene | BYK-2164 | 100 | 16.3 | α | 1.90 | 1.65 | ◎ | Example |
| 2-8 | Plural | ULREA | 8.6 | α | Styrene | BYK-2000 | 100 | 13.2 | α | 1.53 | 1.89 | △ | Example |
| 2-9 | Plural | ULREA | 8.6 | α | Styrene | BYK-108 | 100 | 10.1 | α | 1.17 | 1.34 | ◎ | Example |
| 2-10 | Plural | ULREA | 8.6 | α | THF | BYK-2164 | 100 | 10.9 | α | 1.27 | 1.39 | ◎ | Example |
| 2-11 | Plural | ULREA | 8.6 | α | IPA | BYK-2001 | 100 | 16.3 | α | 1.90 | 1.41 | ◎ | Example |
| 3-1 | Single | ULREA | 8.7 | α | 1 wt % aq. $H_2SO_4$ | — | | 74.9 | α | 8.61 | 1.06 | X | Comparative Example |
| 3-2 | Single | ULREA | 8.7 | α | 0.1 wt % aq. $H_2SO_4$ | — | | 79.6 | α | 9.15 | 1.09 | X | Comparative Example |
| 3-3 | Single | ULREA | 8.7 | α | 0.01 wt % aq. $H_2SO_4$ | — | | 73.6 | α | 8.46 | 1.64 | X | Comparative Example |
| 3-4 | Single | ULREA | 8.7 | α | 1 wt % aq. $H_2SO_4$ | SDBS | 100 | 32.1 | α | 3.69 | 2.31 | △ | Example |
| 3-5 | Single | ULREA | 8.7 | α | 0.1 wt % aq. $H_2SO_4$ | SDBS | 100 | 33.1 | α | 3.80 | 2.46 | ◎ | Example |

Meanwhile, the abbreviations and definitions of the terms in Examples C above are summarized in Table 10 below.

TABLE 10

| Abbreviation/Term | Definition |
|---|---|
| THF | Tetrahydrofuran |
| IPA | Isopropyl alcohol |
| $H_2SO_4$ | Sulfuric acid |
| CuPc | Copper phthalocyanine (blue organic pigment) |
| TiOPc | Titanyl phthalocyanine (blue organic pigment) |
| CoPc | Cobalt phthalocyanine (blue organic pigment) |
| SDBS | Sodium dodecylbenzenesulfonate |
| Measurement method of average primary particle diameter | Average particle diameter of 100 particles observed in plural view fields at the time of TEM observation with 25000 magnifications. |
| Degree of crystallinity | The ratio of the crystalized component relative to the total of the crystalized and amorphous components obtained by the XRD measurement. Durability to light, heat, humidity, or the like is higher when the pigment's degree of crystallinity is higher. |

Meanwhile, definitions of the evaluation in Table 9 are the same as those of Examples B relating to the red organic pigments.

Figure 37:
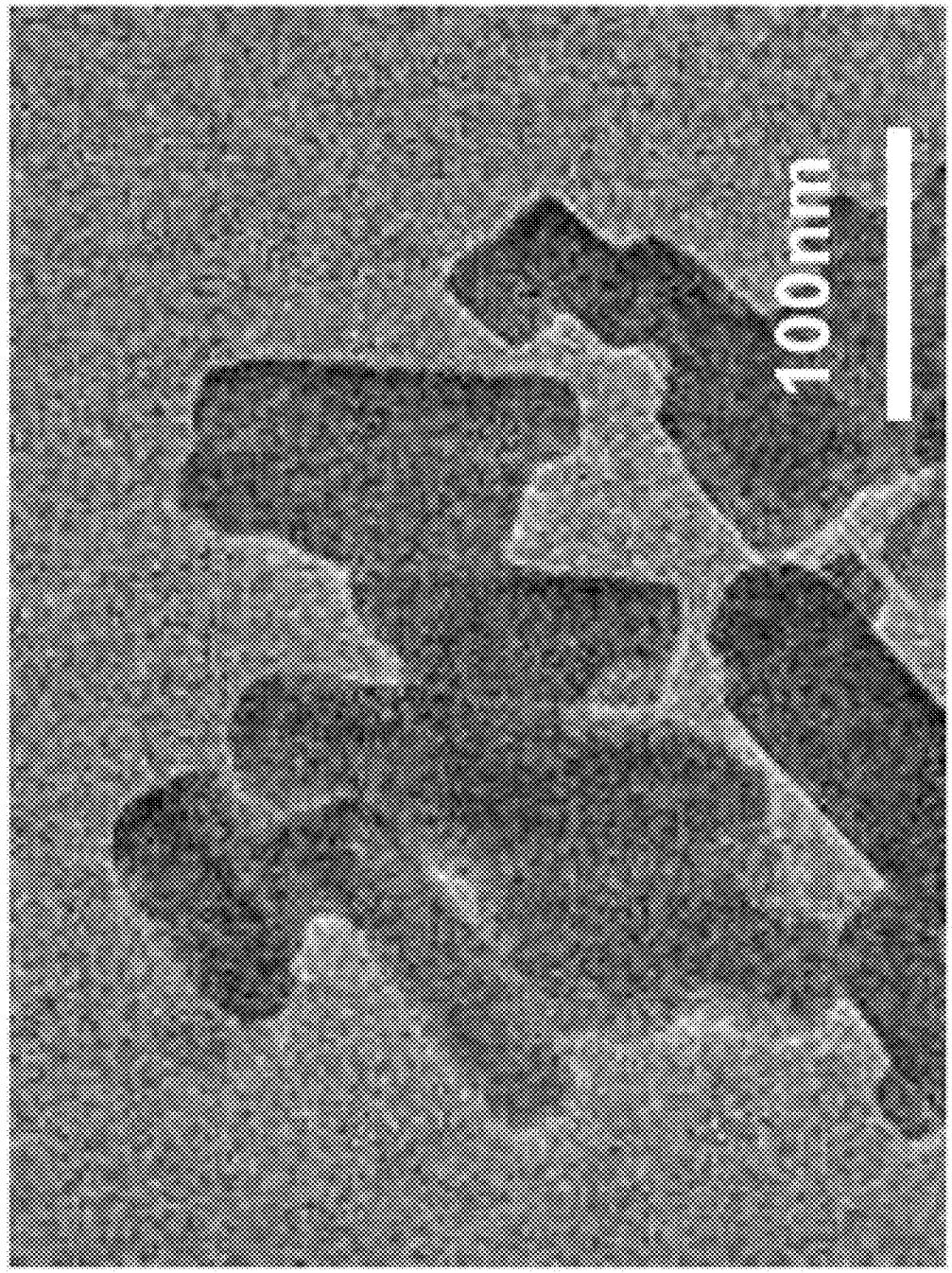
FIG. 37. This is the picture observed with the transmission electron microscope (TEM) of the blue organic pigment microparticles produced in Experiment No. 3-1 of Examples C.

The average primary particle diameter of the blue organic pigment microparticles after the step c (washing) and after the step 2 (action) each was calculated by way of the TEM observation, and the degree of crystallinity of the same was measured by way of the XRD measurement; and they were compared (Table 9). In addition, the TEM pictures obtained in Experiment No. 1 to 7 of Examples C are shown (FIG. 32 to FIG. 35). The TEM picture of Comparative Example obtained in Experiment No. 3-1 of Examples C is also shown (FIG. 37).

According to the experimental results above, in Comparative Examples wherein the solvent which has a partial dissolvability to the blue organic pigment microparticles (in Table 9, this solvent is simply shown as "Solvent"), containing neither a surfactant nor a dispersant, was used in the step 2, the necking and growth were resulted. FIG. 37 shows one example thereof. On the other hand, when the production method of the present invention was applied to Examples C, it became clear that the necking and growth could be suppressed in the obtained blue organic pigment microparticles.

(Case of the Batch Method)

Similarly to the case of using the microreactor, the blue organic pigment microparticles were produced by mixing the A solution and the B solution prepared in accordance with the prescriptions shown in Table 11 below.

Meanwhile, the abbreviations used in the above are as follows; CuPc: copper phthalocyanine, TiOPc: titanyl phthalocyanine, CoPc: cobalt phthalocyanine, and $H_2S_4O$: concentrated sulfuric acid.

The contents of the treatments in Examples C are as follows.

(Step 0)

For mixing and separation with the experimental prescriptions described above by using the batch method, the A solution and the B solution were prepared in the way as described below.

Preparation condition of the separating solvent of the organic pigment particle (A solution):

As described in the experimental prescriptions above, in the case of a single solvent, preparation thereof is not necessary; however, for example, in the case that the experimental prescription described in Patent Document 8 is used, it is preferable to stir by using Clearmix. For example, in Examples C, stirring is conducted by using CLM-2.2S with the rotation number of 10000 rpm for the period of 30 minutes.

Preparation condition of the raw material solution of the organic pigment particle (B solution):

Stirring was conducted by using Clearmix CLM-2.2S with the rotation number of 20000 rpm for the period of 30 minutes.

The preparation temperatures of both the A solution and the B solution were made 40° C.

(Step 1)

The raw material solution of the organic pigment particle (B solution) was introduced into the separating solvent of the organic pigment particle (A solution) in a beaker with stirring the A solution by means of a magnetic stirrer and a stirring bar at the rotation number of 300 rpm so as to effect the mixing of the A solution with the B solution to separate the blue organic pigment microparticles. After the slurry containing the blue organic pigment microparticles obtained in the step 1 were filtrated, the blue organic pigment microparticles were washed with pure water (step c) to obtain a wet cake of the blue organic pigment microparticles (or the dried powder of the blue organic pigment microparticles obtained by conducting the drying treatment thereof with a vacuum-drying or the like).

(Step 2)

The wet cake of the blue organic pigment microparticles (or the dry powder thereof) obtained in the step 1 was introduced into the solvent having a partial dissolvability to the organic pigment microparticle solely and having a surfactant and/or a dispersant added therein (particle property

TABLE 11

| | A solution | | | B solution | | |
|---|---|---|---|---|---|---|
| Experiment No. | Prescription | pH | Measured temperature (° C.) | Prescription | pH | Measured temperature (° C.) |
| 4 | Pure water | 6.9 | 13.9 | CuPc/TiOPc/CoPc/$H_2SO_4$ = 2.1/0.6/0.3/97 (weight ratio) | <1 | — |
| 5 | Pure water | 6.9 | 13.9 | CuPc/TiOPc/CoPc/$H_2SO_4$ = 2.1/0.45/0.45/97 (weight ratio) | <1 | — |
| 6 | Pure water | 6.9 | 13.9 | CuPc/$H_2SO_4$ = 3/97 (weight ratio) | <1 | — | control solvent); and then, the resulting mixture was subjected to the stirring treatment for a prescribed time by using Clearmix.

The changes in the particle diameter and degree of crystallinity of the blue organic pigment microparticles before and after the stirring treatment with the batch method are shown in Table 12 below.

TABLE 12

| Experiment No. | Pigment | Separation apparatus | Particle properties after step c (washing) Average primary particle dispersant diameter: Db (nm) | Crystal type | Step 2 (action) Solvent | Surfactant/ dispersant | Ratio of surfactant/ dispersant to pigment (wt %) | Particle properties after step 2 (action) Average primary particle diameter: Da (nm) | Crystal type | Change of particle diameter before and after the action (Da/Db) | Change of degree of crystallinity before and after the action (Xa/Xb) | Judgement | Example/ Comparative Example |
|---|---|---|---|---|---|---|---|---|---|---|---|---|---|
| 4-1 | Plural | Batch | 79.8 | α | Styrene | — | | 512.3 | α | 6.42 | 1.69 | X | Comparative Example |
| 4-2 | Plural | Batch | 79.8 | α | Toluene | — | | 498.6 | α | 6.25 | 1.69 | X | Comparative Example |
| 4-3 | Plural | Batch | 79.8 | α | Xylene | — | | 401.2 | α | 5.03 | 2.31 | X | Comparative Example |
| 4-4 | Plural | Batch | 79.8 | α | THF | — | | 394.6 | α | 4.94 | 2.65 | X | Comparative Example |
| 4-5 | Plural | Batch | 79.8 | α | IPA | — | | 379.8 | α | 4.76 | 1.97 | X | Comparative Example |
| 4-6 | Plural | Batch | 79.8 | α | Styrene | Pelex TR | 100 | 169.4 | α | 2.12 | 1.67 | ○ | Example |
| 4-7 | Plural | Batch | 79.8 | α | Styrene | BYK-2164 | 100 | 174.6 | α | 2.19 | 1.99 | ○ | Example |
| 4-8 | Plural | Batch | 79.8 | α | Styrene | BYK-2000 | 100 | 169.4 | α | 2.12 | 1.67 | ○ | Example |
| 4-9 | Plural | Batch | 79.8 | α | Styrene | BYK-108 | 100 | 131.6 | α | 1.65 | 2.31 | ○ | Example |
| 4-10 | Plural | Batch | 79.8 | α | TI-IF | BYK-2164 | 100 | 246.5 | α | 3.09 | 2.36 | △ | Example |
| 4-11 | Plural | Batch | 79.8 | α | IPA | BYK-2001 | 100 | 316.2 | α | 3.96 | 1.69 | ○ | Example |
| 5-1 | Plural | Batch | 69.7 | α | Styrene | — | | 600.3 | α | 8.61 | 1.97 | X | Comparative Example |
| 5-2 | Plural | Batch | 69.7 | α | Toluene | — | | 498.4 | α | 7.15 | 2.39 | X | Comparative Example |
| 5-3 | Plural | Batch | 69.7 | α | Xylene | — | | 394.6 | α | 5.66 | 1.64 | X | Comparative Example |
| 5-4 | Plural | Batch | 69.7 | α | TI-IF | — | | 466.3 | α | 6.69 | 1.69 | X | Comparative Example |
| 5-5 | Plural | Batch | 69.7 | α | IPA | — | | 399.9 | α | 5.74 | 1.65 | X | Comparative Example |
| 5-6 | Plural | Batch | 69.7 | α | Styrene | Pelex TR | 100 | 136.4 | α | 1.96 | 1.57 | ○ | Example |
| 5-7 | Plural | Batch | 69.7 | α | Styrene | BYK-2164 | 100 | 269.4 | α | 3.87 | 1.89 | ○ | Example |
| 5-8 | Plural | Batch | 69.7 | α | Styrene | BYK-2000 | 100 | 213.4 | α | 3.06 | 2.34 | ○ | Example |
| 5-9 | Plural | Batch | 69.7 | α | Styrene | BYK-108 | 100 | 276.4 | α | 3.97 | 2.69 | △ | Example |
| 5-10 | Plural | Batch | 69.7 | α | THF | BYK-2164 | 100 | 226.4 | α | 3.25 | 3.64 | ○ | Example |
| 5-11 | Plural | Batch | 69.7 | α | IPA | BYK-2001 | 100 | 276.1 | α | 3.96 | 1.41 | ○ | Example |
| 6-1 | Single | Batch | 71.4 | α | 1 wt % aq. H₂SO₄ | — | | 697.8 | α | 9.77 | 2.16 | X | Comparative Example |
| 6-2 | Single | Batch | 71.4 | α | 0.1 wt % aq. H₂SO₄ | — | | 794.5 | α | 11.13 | 2.54 | X | Comparative Example |
| 6-3 | Single | Batch | 71.4 | α | 0.01 wt % aq. H₂SO₄ | — | | 599.4 | α | 8.39 | 2.46 | X | Comparative Example |
| 6-4 | Single | Batch | 71.4 | α | 1 wt % aq. H₂SO₄ | SDBS | 100 | 241.6 | α | 3.38 | 2.36 | ○ | Example |

The blue organic pigment microparticles obtained after the step 0 (washing) and the step 2 (action) were compared with each other by calculating the average primary particle diameters by way of the TEM observation and measuring the degrees of crystallinity by way of the XRD measurement of them (Table 12). Meanings of the symbols, abbreviations, etc. are the same as those of the case of using the microreactor.

Figure 36:
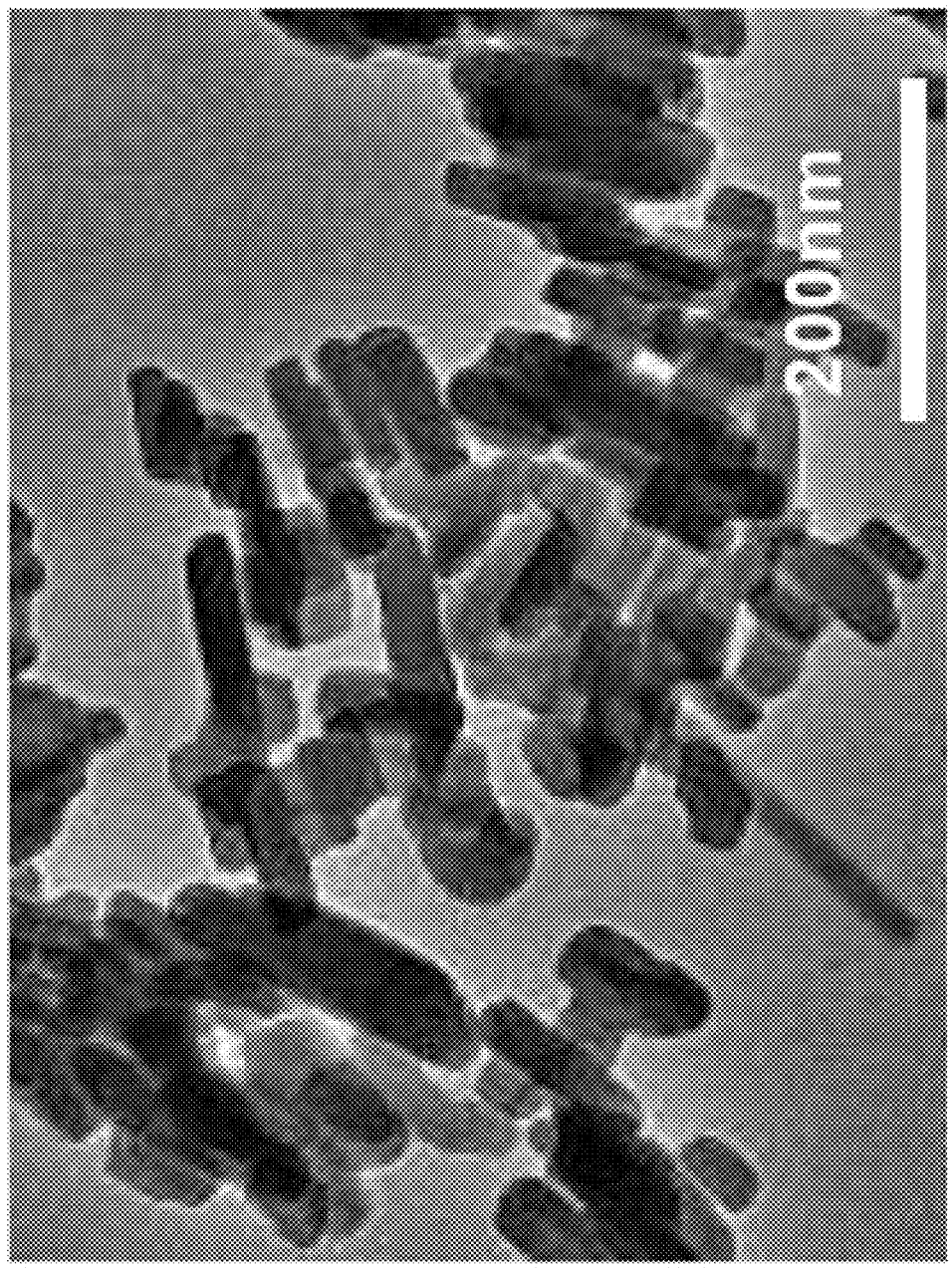
FIG. 36. This is the picture observed with the transmission electron microscope (TEM) of the blue organic pigment microparticles produced in Experiment No. 4-4 of Examples C.

According to the experimental results above, similarly to Examples C in which the microreactor was used, in the batch method, too, when the solvent which has a partial dissolvability to the blue organic pigment microparticles (in Table 12, this solvent is simply shown as "Solvent") containing neither a surfactant nor a dispersant was used in the step 2, the necking and growth were resulted. FIG. 36 shows the picture of the TEM observation of the copper-titanyl-cobalt phthalocyanine microparticles obtained in Experiment No. 4-4 as one example thereof. On the other hand, when the production method of the present invention was applied to Examples C, it became clear that owing to the action of the particle property control solution, the necking and growth could be suppressed in the obtained blue organic pigment microparticles.

As discussed above, from Examples A, Examples B, and Examples C, it is demonstrated that the present invention is effective to organic material microparticles in general.

EXPLANATION OF NUMERAL SYMBOLS

1 First processing surface
2 Second processing surface
10 First processing member
11 First holder
20 Second processing member
21 Second holder
d1 First introduction part
d2 Second introduction part
d10 Opening
d20 Opening

The invention claimed is:

1. A method for producing an organic material microparticle, wherein the method comprises:
step 1 in which the organic material microparticle, at least part of the organic material microparticle being composed of an amorphous portion, is separated; and
step 2 in which a particle property control solution having a surfactant added into a solvent, to which a solubility of the organic material microparticle is in the range of 1 to 1000 µg/g at room temperature and indicates such degree of dissolvability so as to cause some change in the properties of the microparticle, is prepared and said organic material microparticle is introduced into the particle property control solution, wherein
the step 2 is introduced into the organic material microparticle separated in the step 1, to enhance a degree of crystallinity of the organic material microparticle,
wherein, when a particle diameter of the organic material microparticle after the organic material microparticle is introduced into the particle property control solution is (A) and a particle diameter of the organic material microparticle before the organic material microparticle is introduced into the particle property control solution is (B), a ratio of the particle diameter of the organic material microparticle (A)/(B) is in a range of 1.09 to 4.

2. A method for producing an organic material microparticle, wherein the method comprises:
step 1 in which the organic material microparticle, at least part of the organic material microparticle being composed of an amorphous portion, is separated; and
step 2 in which a particle property control solution having a surfactant added into a solvent, to which a solubility of the organic material microparticle is in the range of 1 to 1000 µg/g at room temperature and indicates such degree of dissolvability so as to cause some change in the properties of the microparticle, is prepared and said organic material microparticle is introduced into the particle property control solution, wherein
the step 2 is introduced into the organic material microparticle separated in the step 1, to effect a crystal transition of the organic material microparticle,
wherein, when a particle diameter of the organic material microparticle after the organic material microparticle is introduced into the particle property control solution is (A) and a particle diameter of the organic material microparticle before the organic material microparticle is introduced into the particle property control solution is (B), a ratio of the particle diameter of the organic material microparticle (A)/(B) is in a range of 1.09 to 4.

3. A method for producing an organic material microparticle, wherein the method comprises:
step 1 in which a raw material solution of the organic material microparticle is mixed with a separating solvent L for separating at least one kind of the organic material particles from the raw material solution of the organic material microparticle thereby effecting separation of an organic material microparticle (P1); and
step 2 in which a particle property control solution having a surfactant, which is capable of suppressing growth of the organic material microparticle, added into a solvent to which a solubility of the organic material microparticle is in the range of 1 to 1000 µg/g at room temperature and indicates such degree of dissolvability so as to cause some change in the properties of the microparticle, is prepared and the said organic material microparticle (P1) is introduced into the particle property control solution, wherein
the step 2 is made to act so as to control particle properties of the organic material microparticle (P1) separated in the step 1,
wherein, when a particle diameter of the organic material microparticle after the organic material microparticle is introduced into the particle property control solution is (A) and a particle diameter of the organic material microparticle before the organic material microparticle is introduced into the particle property control solution is (B), a ratio of the particle diameter of the organic material microparticle (A)/(B) is in a range of 1.09 to 4.

4. The method for producing the organic material microparticle according to claim 3, wherein the step 2 is made to act so as to change at least any one of degree of crystallinity, crystal type, and crystal diameter of the organic material microparticle (P1).

5. The method for producing the organic material microparticle according to claim 3, wherein the method comprises step c in which the organic material microparticle (P1) obtained in the step 1 is subjected to washing and/or solvent substitution, and an organic material microparticle (P2) obtained in the step c is introduced into the particle property control solution.

6. The method for producing the organic material microparticle according to claim 3, wherein the organic material microparticle contains an amorphous portion at least in part thereof.

7. The method for producing the organic material microparticle according to claim 1, wherein at a time when the organic material microparticle is introduced into the particle property control solution, a stirring treatment is conducted so as to control properties of the organic material microparticle by means of a stirring energy.

8. The method for producing the organic material microparticle according to claim 1, wherein the organic material microparticle is of a biologically ingestible substance.

9. The method for producing the organic material microparticle according to claim 1, wherein the organic material microparticle is of a resin.

10. The method for producing the organic material microparticle according to claim 1, wherein the organic material microparticle is of an organic pigment.

11. The method for producing the organic material microparticle according to claim 10, wherein the organic material microparticle is of a red organic pigment or of a blue organic pigment.

12. The method for producing the organic material microparticle according to claim 3, wherein the step 1 is conducted in a microreactor in which at least two fluids to be processed, comprising the raw material solution of the organic material microparticle and the separating solvent L, are introduced into between a first processing surface and a second processing surface which are disposed in a position they are faced with each other so as to be able to approach to and separate from each other, at least one of which rotates relative to the other;

a separating force which acts in a direction to separate the first processing surface and the second processing surface from each other is generated by an introduction pressure imparted to between the first processing surface and the second processing surface;

with keeping a distance of 1 mm or less between the first processing surface and the second processing surface by the separating force, the at least two fluids to be processed are caused to converge with each other between the first processing surface and the second processing surface that are kept at the distance of 1 mm or less thereby causing to pass the fluids to be processed through between the first processing surface and the second processing surface so as to form a thin film fluid; and the fluids to be processed are made to react with each other in the thin film fluid.

13. The method for producing the organic material microparticle according to claim 7, wherein the stirring is conducted by using a stirrer equipped with a rotating and stirring blade.

14. The method for producing the organic material microparticle according to claim 1, wherein particle diameters of the organic material microparticles measured before and after the organic material microparticle is introduced into the particle property control solution is in a range of 100 nm or less.

15. The method for producing the organic material microparticle according to claim 3, wherein the particle diameter of the organic material microparticle (P1) is in a range of 30 nm or less.

16. The method for producing the organic material microparticle according to claim 10, wherein the particle property control solution does not substantially contain a pigment derivative.

* * * * *